US012643955B2

(12) United States Patent
Naka et al.

(10) Patent No.: US 12,643,955 B2
(45) Date of Patent: Jun. 2, 2026

(54) HUMANIZED ANTI-GPC-1 ANTIBODY

(71) Applicant: IWATE MEDICAL UNIVERSITY, Iwate (JP)

(72) Inventors: Tetsuji Naka, Shiwa-gun (JP); Satoshi Serada, Shiwa-gun (JP)

(73) Assignee: IWATE MEDICAL UNIVERSITY, Iwate (JP)

( * ) Notice: Subject to any disclaimer, the term of this patent is extended or adjusted under 35 U.S.C. 154(b) by 699 days.

(21) Appl. No.: 18/009,024

(22) PCT Filed: Jun. 10, 2021

(86) PCT No.: PCT/JP2021/022085
§ 371 (c)(1),
(2) Date: Dec. 8, 2022

(87) PCT Pub. No.: WO2021/251459
PCT Pub. Date: Dec. 16, 2021

(65) Prior Publication Data
US 2023/0250188 A1 Aug. 10, 2023

(30) Foreign Application Priority Data
Jun. 11, 2020 (JP) ................................. 2020-101856

(51) Int. Cl.
| | |
|---|---|
| C07K 16/30 | (2006.01) |
| A61K 39/00 | (2006.01) |
| A61K 47/68 | (2017.01) |
| A61P 1/18 | (2006.01) |
| A61P 35/00 | (2006.01) |
| C07K 16/28 | (2006.01) |

(52) U.S. Cl.
CPC ...... *C07K 16/303* (2013.01); *A61K 47/68031* (2023.08); *A61K 47/6859* (2017.08); *A61P 1/18* (2018.01); *A61P 35/00* (2018.01); *C07K 16/2818* (2013.01); *A61K 2039/505* (2013.01); *C07K 2317/24* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| | | |
|---|---|---|
| 2017/0066836 A1 | 3/2017 | Naka et al. |
| 2017/0166642 A1 | 6/2017 | Pantaleo et al. |
| 2018/0258177 A1 | 9/2018 | Kwon et al. |
| 2020/0308299 A1 | 10/2020 | Naka et al. |

FOREIGN PATENT DOCUMENTS

| | | |
|---|---|---|
| JP | 2019-513118 A | 5/2019 |
| JP | 2020-503245 A | 1/2020 |
| WO | 2015/098112 A1 | 7/2015 |
| WO | 2018/200496 A1 | 11/2018 |
| WO | WO-2018199318 A1 * | 11/2018 ............. A61P 35/00 |

OTHER PUBLICATIONS

Doronina et al. Nature Biotechnology. 21(7): 778-784; Published: Jul. 2003 (Year: 2003).*
Okeley et al. Clinical Cancer Research. 16(3): 888-897; Published: Feb. 1, 2010 (Year: 2010).*
Matsuzaki et al. International Journal of Cancer. 142: 1056-1066; Published Online: Oct. 21, 2017 (Year: 2017).*
Nishigaki et al. British Journal of Cancer. 122: 1333-1341; Published Online: Mar. 10, 2020 (Year: 2020).*
Chen et al. J. Mol. Bio. (1999) 293, 865-881 (Year: 1999).*
Padlan et al. PNAS 1989, 86:5938-5942 (Year: 1989).*
Lamminmaki et al. JBC 2001, 276:36687-36694 (Year: 2001).*
Murphy et al. Journal of Immunological Methods. 463: 127-133; Published: Oct. 12, 2018 (Year: 2018).*
Rudikoff et al. Proc Natl Acad Sci USA 1982 vol. 79 p. 1979 (Year: 1979).*
Matsuzaki et al., "Anti-glypican-1 antibody-drug conjugate exhibits potent preclinical antitumor activity against glypican-1 positive uterine cervical cancer," International Journal of Cancer, 142: 1056-1066 (2018).
Nishigaki et al., "Anti-glypican-1 antibody-drug conjugate is a potential therapy against pancreatic cancer," British Journal of Cancer, 122: 1333-1341 (2020).
Lund et al., "The Role of Glypican-1 in the Tumour Microenvironment," Tumor Microenvironment. Advances in Experimental Medicine and Biology,1245: 163-176 (2020).
International Search Report issued in corresponding International Patent Application No. PCT/JP2021/022085 dated Aug. 10, 2021.
Extended European Search Report issued in the corresponding Application No. 21823133.0, dated Nov. 7, 2023.
Munekage et al., "A glypican-I-targeted antibody-drug conjugate exhibits potent tumor growth inhibition in glypican-I-positive pancreatic cancer and esophageal squamous cell carcinoma", NEOPLASIA, 23(9): 939-950, XP93094629, Sep. 1, 2021.

* cited by examiner

*Primary Examiner* — Juliet C Switzer
*Assistant Examiner* — Katherine Ann Holtzman
(74) *Attorney, Agent, or Firm* — Morgan, Lewis & Bockius LLP

(57) ABSTRACT

The present disclosure provides a humanized antibody that specifically binds to Glypican-1 (GPC-1), and also provides technologies, methods, medicines, and the like related to the humanized antibody. In one aspect, the present disclosure provides a humanized anti-GPC-1 monoclonal antibody that has a high affinity for GPC-1 and has high internalization activity in GPC-1-positive cells. In another aspect, the present disclosure also provides a composition for preventing or treating Glypican-1-positive cancer that includes a complex of a humanized anti-GPC-1 monoclonal antibody and a medicine having cytotoxic activity.

18 Claims, 22 Drawing Sheets
Specification includes a Sequence Listing.

Figure 1

| Ligand chimeric mouse Ab (01a033) | ka (1/Ms) | kd (1/s) | Rmax (RU) | KD | Chi² |
|---|---|---|---|---|---|
|  | 3.02E+05 | 3.09E-03 | 74.6 | 1.02E-08 | 4.89E-01 |
| T1 | 2.38E+05 | 1.34E-03 | 58.9 | 5.62E-09 | 2.57E-01 |
| T2 | 2.40E+05 | 1.25E-03 | 60.3 | 5.20E-09 | 3.34E-01 |
| T3 | 2.29E+05 | 7.13E-04 | 62.9 | 3.11E-09 | 3.10E-01 |
| T7 | 3.43E+05 | 4.11E-03 | 64.5 | 1.20E-08 | 5.89E-01 |
| T8 | 2.34E+05 | 1.18E-03 | 62 | 5.07E-09 | 3.31E-01 |
| T10 | 1.99E+05 | 1.50E-03 | 56.7 | 7.55E-09 | 2.78E-01 |
| T11 | 1.86E+05 | 5.06E-02 | 79.6 | 2.72E-07 | 5.46E-01 |
| T22 | 2.32E+05 | 5.06E-02 | 73.4 | 2.18E-07 | 9.04E-02 |
| T26 | 1.78E+03 | 1.30E-01 | 13606.9 | 7.28E-05 | 3.98E-01 |
| T28 | 3.13E+05 | 6.79E-03 | 59 | 2.17E-08 | 4.44E-01 |
| T29 | 2.05E+05 | 6.64E-02 | 78.4 | 3.24E-07 | 8.95E-02 |
| T31 | 1.98E+05 | 5.39E-02 | 65.4 | 2.71E-07 | 2.37E-01 |
| T32 | 2.08E+05 | 6.03E-02 | 81.2 | 2.90E-07 | 6.64E-02 |
| T33 | 1.60E+05 | 7.38E-02 | 70.4 | 4.62E-07 | 4.14E-02 |
| T34 | 1.72E+05 | 3.93E-03 | 59.2 | 2.28E-08 | 4.28E-01 |
| T36 | 2.31E+05 | 2.27E-03 | 60.3 | 9.80E-09 | 1.84E-01 |
| T43 | 1.69E+05 | 1.06E-02 | 62.4 | 6.24E-08 | 1.99E-01 |
| T56 | 2.59E+05 | 1.80E-03 | 46.6 | 6.93E-09 | 3.65E-01 |
| T57 | 1.32E+05 | 1.35E-02 | 97 | 1.02E-07 | 1.36E-01 |
| T59 | 1.97E+05 | 5.93E-02 | 96.9 | 3.02E-07 | 9.81E-02 |
| Anti-GPC1 mAb 01a033 | 1.23E+05 | 3.88E-03 | 65.7 | 3.16E-08 | 1.15E+00 |

Cytotoxic drug: MMAF

Cleavable linker

2nd Ab Fab ADC

Anti-GPC1 mAb
Humanized antibody

GPC1

TE14 Cell

TE14Cell 2,000 cells/well, RPMI1640+10%FBS+1%PS, Culture time 144h
1st Ab: 0, 0.004, 0.0156, 0.0625, 0.25, 1.0, 4.0 nM
2nd Ab Fab ADC: Fab-αMFc-CL-MMAF Catalog No.:AH-202AF-50 lot:20180424-2,
Manufacturer Moradec, Concentration 2 μg/ml

| clone | IC50 (nM) |
|---|---|
| T2 | 0.0361 |
| T7 | 0.0365 |
| T8 | 0.0379 |
| T1 | 0.0399 |
| T36 | 0.0459 |
| T57 | 0.0459 |
| T10 | 0.0488 |
| T34 | 0.0501 |
| T56 | 0.0501 |
| T3 | 0.0526 |
| chimeric-mouse Ab (01a033) | 0.0710 |
| T11 | 0.1211 |
| T28 | 0.1527 |
| T43 | 0.3704 |
| T59 | 0.3704 |
| T31 | 0.6881 |
| T22 | 0.7453 |
| T26 | 0.8027 |
| T32 | 0.8876 |
| T33 | 1.8614 |
| T29 | 2.1824 |

SEQUENCE LISTING

<160> NUMBER OF SEQ ID NOS: 92

<210> SEQ ID NO 1
<211> LENGTH: 1677
<212> TYPE: DNA
<213> ORGANISM: Homo sapiens

<400> SEQUENCE: 1

```
atggagctcc gggcccgagg ctggtggctg ctatgtgcgg ccgcagcgct ggtcgcctgc       60
gcccgcgggg acccggccag caagagccgg agctgcggcg aggtccgcca gatctacgga      120
gccaagggct tcagcctgag cgacgtgccc caggcggaga tctcgggtga gcacctgcgg      180
atctgtcccc agggctacac ctgctgcacc agcgagatgg aggagaacct ggccaaccgc      240
agccatgccg agctggagac cgcgctccgg gacagcagcc gcgtcctgca ggccatgctt      300
gccacccagc tgcgcagctt cgatgaccac ttccagcacc tgctgaacga ctcggagcgg      360
acgctgcagg ccaccttccc cggcgccttc ggagagctgt acacgcagaa cgcgagggcc      420
ttccgggacc tgtactcaga gctgcgcctg tactaccgcg gtgccaacct gcacctggag      480
gagacgctgg ccgagttctg ggcccgcctg ctcgagcgcc tcttcaagca gctgcacccc      540
cagctgctgc tgcctgatga ctacctggac tgcctgggca gcaggccga ggcgctgcgg      600 cccttcgggg aggccccgag agagctgcgc ctgcgggcca cccgtgcctt cgtggctgct      660
cgctcctttg tgcagggcct gggcgtggcc agcgacgtg tccggaaagt ggctcaggtc      720
cccctgggcc cggagtgctc gagagctgtc atgaagctgg tctactgtgc tcactgcctg      780
ggagtccccg cgccaggcc ctgccctgac tattgccgaa atgtgctcaa gggctgcctt      840
gccaaccagg ccgacctgga cgccgagtgg aggaacctcc tggactccat ggtgctcatc      900
accgacaagt tctggggtac atcgggtgtg gagagtgtca tcggcagcgt gcacacgtgg      960
ctggcggagg ccatcaacgc cctccaggac aacagggaca cgctcacggc caaggtcatc     1020
cagggctgcg ggaaccccaa ggtcaacccc cagggccccg ggcctgagga gaagcggcgc     1080
cggggcaagc tggccccgcg ggagaggcca ccttcaggca cgctggagaa gctggtctcc     1140
gaagccaagg cccagctccg cgacgtccag gacttctgga tcagcctccc agggacactg     1200
tgcagtgaga agatggcccct gagcactgcc agtgatgacc gctgctggaa cgggatggcc     1260
agaggccggt acctccccga ggtcatgggt gacggcctgg ccaaccagat caacaacccc     1320
gaggtggagg tggacatcac caagccggac atgaccatcg gcagcagat catgcagctg     1380
```

-continued

```
aagatcatga ccaaccggct gcgcagcgcc tacaacggca acgacgtgga cttccaggac   1440
gccagtgacg acggcagcgg ctcgggcagc ggtgatggct gtctggatga cctctgcagc   1500
cggaaggtca gcaggaagag ctccagctcc cggacgccct tgacccatgc cctcccaggc   1560
ctgtcagagc aggaaggaca gaagacctcg gctgccagct gccccagcc cccgaccttc    1620 ctcctgcccc tcctcctctt cctggcccctt acagtagcca ggccccggtg gcggtaa     1677
```

<210> SEQ ID NO 2
<211> LENGTH: 558
<212> TYPE: PRT
<213> ORGANISM: Homo sapiens

<400> SEQUENCE: 2

```
Met Glu Leu Arg Ala Arg Gly Trp Trp Leu Leu Cys Ala Ala Ala Ala
1               5                   10                  15

Leu Val Ala Cys Ala Arg Gly Asp Pro Ala Ser Lys Ser Arg Ser Cys
                20                  25                  30

Gly Glu Val Arg Gln Ile Tyr Gly Ala Lys Gly Phe Ser Leu Ser Asp
            35                  40                  45

Val Pro Gln Ala Glu Ile Ser Gly Glu His Leu Arg Ile Cys Pro Gln
        50                  55                  60

Gly Tyr Thr Cys Cys Thr Ser Glu Met Glu Glu Asn Leu Ala Asn Arg
65                  70                  75                  80

Ser His Ala Glu Leu Glu Thr Ala Leu Arg Asp Ser Ser Arg Val Leu
                85                  90                  95

Gln Ala Met Leu Ala Thr Gln Leu Arg Ser Phe Asp Asp His Phe Gln
            100                 105                 110

His Leu Leu Asn Asp Ser Glu Arg Thr Leu Gln Ala Thr Phe Pro Gly
            115                 120                 125

Ala Phe Gly Glu Leu Tyr Thr Gln Asn Ala Arg Ala Phe Arg Asp Leu
        130                 135                 140

Tyr Ser Glu Leu Arg Leu Tyr Tyr Arg Gly Ala Asn Leu His Leu Glu
145                 150                 155                 160

Glu Thr Leu Ala Glu Phe Trp Ala Arg Leu Leu Glu Arg Leu Phe Lys
                165                 170                 175

Gln Leu His Pro Gln Leu Leu Leu Pro Asp Asp Tyr Leu Asp Cys Leu
            180                 185                 190

Gly Lys Gln Ala Glu Ala Leu Arg Pro Phe Gly Glu Ala Pro Arg Glu
        195                 200                 205

Leu Arg Leu Arg Ala Thr Arg Ala Phe Val Ala Ala Arg Ser Phe Val
    210                 215                 220

Gln Gly Leu Gly Val Ala Ser Asp Val Val Arg Lys Val Ala Gln Val
225                 230                 235                 240

Pro Leu Gly Pro Glu Cys Ser Arg Ala Val Met Lys Leu Val Tyr Cys
                245                 250                 255

Ala His Cys Leu Gly Val Pro Gly Ala Arg Pro Cys Pro Asp Tyr Cys
            260                 265                 270

Arg Asn Val Leu Lys Gly Cys Leu Ala Asn Gln Ala Asp Leu Asp Ala
        275                 280                 285

Glu Trp Arg Asn Leu Leu Asp Ser Met Val Leu Ile Thr Asp Lys Phe
    290                 295                 300

Trp Gly Thr Ser Gly Val Glu Ser Val Ile Gly Ser Val His Thr Trp
305                 310                 315                 320

Leu Ala Glu Ala Ile Asn Ala Leu Gln Asp Asn Arg Asp Thr Leu Thr
```

-continued

```
                      325                   330                   335
Ala Lys Val Ile Gln Gly Cys Gly Asn Pro Lys Val Asn Pro Gln Gly
            340                   345                   350

Pro Gly Pro Glu Glu Lys Arg Arg Arg Gly Lys Leu Ala Pro Arg Glu
            355                   360                   365

Arg Pro Pro Ser Gly Thr Leu Glu Lys Leu Val Ser Glu Ala Lys Ala
            370                   375                   380

Gln Leu Arg Asp Val Gln Asp Phe Trp Ile Ser Leu Pro Gly Thr Leu
385                   390                   395                   400

Cys Ser Glu Lys Met Ala Leu Ser Thr Ala Ser Asp Asp Arg Cys Trp
                      405                   410                   415

Asn Gly Met Ala Arg Gly Arg Tyr Leu Pro Glu Val Met Gly Asp Gly
                      420                   425                   430

Leu Ala Asn Gln Ile Asn Asn Pro Glu Val Glu Val Asp Ile Thr Lys
                      435                   440                   445

Pro Asp Met Thr Ile Arg Gln Gln Ile Met Gln Leu Lys Ile Met Thr
            450                   455                   460

Asn Arg Leu Arg Ser Ala Tyr Asn Gly Asn Asp Val Asp Phe Gln Asp
465                   470                   475                   480

Ala Ser Asp Asp Gly Ser Gly Ser Gly Ser Gly Asp Gly Cys Leu Asp
                      485                   490                   495

Asp Leu Cys Ser Arg Lys Val Ser Arg Lys Ser Ser Ser Ser Arg Thr
                      500                   505                   510

Pro Leu Thr His Ala Leu Pro Gly Leu Ser Glu Gln Glu Gly Gln Lys
                      515                   520                   525

Thr Ser Ala Ala Ser Cys Pro Gln Pro Pro Thr Phe Leu Leu Pro Leu
            530                   535                   540

Leu Leu Phe Leu Ala Leu Thr Val Ala Arg Pro Arg Trp Arg
545                   550                   555
```

<210> SEQ ID NO 3
<211> LENGTH: 1673
<212> TYPE: DNA
<213> ORGANISM: Mus musculus

<400> SEQUENCE: 3

```
tggaactccg acccgaggc tggtggctgc tgtgcgcggc cgccgcgctg gtcgtctgcg        60
cccgcgggga ccccgccagc aagagccgga gctgcagcga agtccgccag atctacgggg      120
ctaagggctt tagcctgagc gatgtgcctc aggcagagat ctcgggtgag cacctgcgga      180 tctgcccca gggctacact tgctgtacta gtgagatgga ggagaatttg gccaaccaca      240
gccgaatgga gctggagagc gcactccatg acagcagccg cgccctgcag gccacactgg      300
ccacccagct gcatggcatc gatgaccact tccagcgcct gctgaatgac tcggagcgca      360
cactgcagga ggctttccct gggggcctttg gggacctgta tacgcagaac actcgtgcct      420
tccgggacct atatgctgag ctgcgcctct actaccgtgg ggccaacctg caccttgagg      480
agacgctggc cgagttctgg gcacggctgc tggagcgcct cttcaagcag ctgcaccccc      540
agctgctgcc tgatgactac ctggactgcc tgggcaagca ggcggaggca ctgcggccgt      600
ttggagatgc ccctcgagaa ctgcgcctgc gggccacccg tgcctttgtg ctgcacgtt       660 cctttgtgca gggcctgggt gtggccagtg atgtagtccg gaaggtggcc caggtacctc      720
tggccccaga atgttctcgg gccatcatga agttggtcta ctgtgctcat tgccggggag      780
tcccgggcgc ccggccctgc cccgactatt gccgaaatgt gctcaaaggc tgccttgcca      840
```

-continued

```
accaggccga cctggatgcc gagtggagga acctcctgga ctccatggtg ctcatcactg    900
acaagttctg gggcccgtcg ggtgcggaga gtgtcattgg cggtgtgcac gtgtggctgg    960
cggaggccat caacgccctc caggacaaca aggacacact cacagctaag gtcatccagg   1020
cctgtggaaa ccccaaggtc aatccccacg gctctgggcc cgaggagaag cgtcgccgtg   1080
gcaaattggc actgcaggag aagccctcca caggtactct ggaaaaactg gtctctgagg   1140
ccaaggccca gctccgagac attcaggact tctggatcag cctcccaggg acactgtgca   1200
gtgagaagat ggccatgagt cctgccagtg acgaccgctg ctggaatgga atttccaagg   1260
gccggtacct accagaggtg atgggtgacg ggctggccaa ccagatcaac aaccctgagg   1320
tggaagtgga catcaccaag ccagacatga ccatccgcca gcagattatg cagctcaaga   1380
tcatgaccaa ccgtttacgt ggcgcctatg cggcaacga cgtggacttc caggatgcta   1440
gtgatgacgg cagtggctcc ggcagcggtg cgggatgccc agatgacacc tgtggccgga   1500
gggtcagcaa gaagagttcc agctcccgga ccccccttgac ccatgccctc cccggcctgt   1560
cagaacagga gggacagaag acctcagctg ccacctgccc agagccccac agcttcttcc   1620
tgctcttcct cgtcaccttg gtccttgcgg cagccaggcc caggtggcgg taa          1673
```

<210> SEQ ID NO 4
<211> LENGTH: 557
<212> TYPE: PRT
<213> ORGANISM: Mus musculus

<400> SEQUENCE: 4

```
Met Glu Leu Arg Thr Arg Gly Trp Trp Leu Leu Cys Ala Ala Ala Ala
1               5                   10                  15

Leu Val Val Cys Ala Arg Gly Asp Pro Ala Ser Lys Ser Arg Ser Cys
            20                  25                  30

Ser Glu Val Arg Gln Ile Tyr Gly Ala Lys Gly Phe Ser Leu Ser Asp
        35                  40                  45

Val Pro Gln Ala Glu Ile Ser Gly Glu His Leu Arg Ile Cys Pro Gln
    50                  55                  60

Gly Tyr Thr Cys Cys Thr Ser Glu Met Glu Glu Asn Leu Ala Asn His
65                  70                  75                  80

Ser Arg Met Glu Leu Glu Ser Ala Leu His Asp Ser Ser Arg Ala Leu
                85                  90                  95

Gln Ala Thr Leu Ala Thr Gln Leu His Gly Ile Asp Asp His Phe Gln
            100                 105                 110

Arg Leu Leu Asn Asp Ser Glu Arg Thr Leu Gln Glu Ala Phe Pro Gly
        115                 120                 125

Ala Phe Gly Asp Leu Tyr Thr Gln Asn Thr Arg Ala Phe Arg Asp Leu
    130                 135                 140

Tyr Ala Glu Leu Arg Leu Tyr Tyr Arg Gly Ala Asn Leu His Leu Glu
145                 150                 155                 160

Glu Thr Leu Ala Glu Phe Trp Ala Arg Leu Leu Glu Arg Leu Phe Lys
                165                 170                 175

Gln Leu His Pro Gln Leu Leu Pro Asp Asp Tyr Leu Asp Cys Leu Gly
            180                 185                 190

Lys Gln Ala Glu Ala Leu Arg Pro Phe Gly Asp Ala Pro Arg Glu Leu
        195                 200                 205

Arg Leu Arg Ala Thr Arg Ala Phe Val Ala Ala Arg Ser Phe Val Gln
    210                 215                 220
```

-continued

```
Gly Leu Gly Val Ala Ser Asp Val Val Arg Lys Val Ala Gln Val Pro
225                 230                 235                 240

Leu Ala Pro Glu Cys Ser Arg Ala Ile Met Lys Leu Val Tyr Cys Ala
                245                 250                 255

His Cys Arg Gly Val Pro Gly Ala Arg Pro Cys Pro Asp Tyr Cys Arg
            260                 265                 270

Asn Val Leu Lys Gly Cys Leu Ala Asn Gln Ala Asp Leu Asp Ala Glu
        275                 280                 285

Trp Arg Asn Leu Leu Asp Ser Met Val Leu Ile Thr Asp Lys Phe Trp
    290                 295                 300

Gly Pro Ser Gly Ala Glu Ser Val Ile Gly Gly Val His Val Trp Leu
305                 310                 315                 320

Ala Glu Ala Ile Asn Ala Leu Gln Asp Asn Lys Asp Thr Leu Thr Ala
                325                 330                 335

Lys Val Ile Gln Ala Cys Gly Asn Pro Lys Val Asn Pro His Gly Ser
            340                 345                 350

Gly Pro Glu Glu Lys Arg Arg Arg Gly Lys Leu Ala Leu Gln Glu Lys
        355                 360                 365

Pro Ser Thr Gly Thr Leu Glu Lys Leu Val Ser Glu Ala Lys Ala Gln
    370                 375                 380

Leu Arg Asp Ile Gln Asp Phe Trp Ile Ser Leu Pro Gly Thr Leu Cys
385                 390                 395                 400

Ser Glu Lys Met Ala Met Ser Pro Ala Ser Asp Asp Arg Cys Trp Asn
                405                 410                 415

Gly Ile Ser Lys Gly Arg Tyr Leu Pro Glu Val Met Gly Asp Gly Leu
            420                 425                 430

Ala Asn Gln Ile Asn Asn Pro Glu Val Glu Val Asp Ile Thr Lys Pro
        435                 440                 445

Asp Met Thr Ile Arg Gln Gln Ile Met Gln Leu Lys Ile Met Thr Asn
    450                 455                 460

Arg Leu Arg Gly Ala Tyr Gly Gly Asn Asp Val Asp Phe Gln Asp Ala
465                 470                 475                 480

Ser Asp Asp Gly Ser Gly Ser Gly Ser Gly Gly Cys Pro Asp Asp
                485                 490                 495

Thr Cys Gly Arg Arg Val Ser Lys Lys Ser Ser Ser Arg Thr Pro
            500                 505                 510

Leu Thr His Ala Leu Pro Gly Leu Ser Glu Gln Glu Gly Gln Lys Thr
        515                 520                 525

Ser Ala Ala Thr Cys Pro Glu Pro His Ser Phe Phe Leu Leu Phe Leu
    530                 535                 540

Val Thr Leu Val Leu Ala Ala Ala Arg Pro Arg Trp Arg
545                 550                 555
```

```
<210> SEQ ID NO 5
<211> LENGTH: 119
<212> TYPE: PRT
<213> ORGANISM: artificial sequence
<220> FEATURE:
<223> OTHER INFORMATION: 01a033 heavy chain variable region

<400> SEQUENCE: 5

Gln Val Gln Leu Lys Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30
```

-continued

```
Tyr Met His Trp Val Lys Gln Ser Pro Glu Lys Ser Leu Glu Trp Ile
        35              40              45

Gly Glu Ile Asn Pro Ser Thr Gly Asp Thr Thr Tyr Asn Gln Lys Phe
    50              55              60

Lys Ala Lys Ala Thr Leu Thr Val Asp Lys Ser Ser Ser Thr Ala Tyr
65              70              75              80

Met Gln Leu Lys Ser Leu Thr Ser Glu Asp Ser Ala Val Tyr Tyr Cys
            85              90              95

Ala Arg Glu Lys Arg Asp Asp Gly Val Phe Ala Tyr Trp Gly Gln Gly
        100             105             110

Thr Leu Val Thr Val Ser Ser
        115

<210> SEQ ID NO 6
<211> LENGTH: 107
<212> TYPE: PRT
<213> ORGANISM: artificial sequence
<220> FEATURE:
<223> OTHER INFORMATION: 01a033 light chain variable region

<400> SEQUENCE: 6

Asp Ile Val Met Ser Gln Ser Pro Lys Ser Met Ser Met Ser Val Gly
1               5               10              15

Glu Arg Val Ala Leu Ser Cys Lys Ala Ser Glu Asn Val Gly Thr Tyr
        20              25              30

Val Ser Trp Tyr Gln Gln Lys Pro Glu Gln Ser Pro Lys Leu Leu Ile
        35              40              45

Tyr Gly Ala Ser Asn Arg Tyr Thr Gly Val Pro Asp Arg Phe Thr Gly
    50              55              60

Ser Gly Ser Ala Thr Asp Phe Thr Leu Thr Ile Ser Ser Val Gln Ala
65              70              75              80

Glu Asp Leu Ala Asp Tyr Tyr Cys Gly Gln Ser Tyr Ser Tyr Pro Leu
            85              90              95

Thr Phe Gly Ala Gly Thr Lys Leu Glu Leu Lys
        100             105

<210> SEQ ID NO 7
<211> LENGTH: 119
<212> TYPE: PRT
<213> ORGANISM: artificial sequence
<220> FEATURE:
<223> OTHER INFORMATION: humanized heavy chain variable region

<400> SEQUENCE: 7

Gln Val Gln Leu Val Gln Ser Gly Ala Glu Val Lys Lys Pro Gly Ala
1               5               10              15

Ser Val Lys Val Ser Cys Lys Ala Ser Gly Tyr Thr Phe Thr Gly Tyr
        20              25              30

Tyr Met His Trp Val Arg Gln Ala Pro Gly Gln Gly Leu Glu Trp Met
        35              40              45

Gly Glu Ile Asn Pro Ser Thr Gly Asp Thr Thr Tyr Asn Gln Lys Phe
    50              55              60

Lys Ala Arg Val Thr Met Thr Arg Asp Thr Ser Thr Ser Thr Val Tyr
65              70              75              80

Met Glu Leu Ser Ser Leu Arg Ser Glu Asp Thr Ala Val Tyr Tyr Cys
            85              90              95

Ala Arg Glu Lys Arg Asp Asp Gly Val Phe Ala Tyr Trp Gly Gln Gly
        100             105             110
```

-continued

```
Thr Leu Val Thr Val Ser Ser
        115

<210> SEQ ID NO 8
<211> LENGTH: 108
<212> TYPE: PRT
<213> ORGANISM: artificial sequence
<220> FEATURE:
<223> OTHER INFORMATION: T2 humanized light chain variable region

<400> SEQUENCE: 8

Asp Ile Val Met Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Val Trp Tyr Gln Gln Lys Pro Gly Lys Pro Lys Leu Leu Ile
        35                  40                  45

Tyr Ser Ala Ser Val Leu Gln Ser Gly Val Pro Ser Arg Phe Ser Gly
    50                  55                  60

Arg Gly Tyr Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Ser Ile Pro Pro
                85                  90                  95

Val Thr Phe Gly Gly Gly Thr Lys Val Glu Ile Lys
            100                 105

<210> SEQ ID NO 9
<211> LENGTH: 107
<212> TYPE: PRT
<213> ORGANISM: artificial sequence
<220> FEATURE:
<223> OTHER INFORMATION: T7 humanized light chain variable region

<400> SEQUENCE: 9

Ala Ile Gln Leu Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Ser Asp Ala Ser Asn Leu Ala Ser Gly Val Pro Leu Arg Phe Ser Gly
    50                  55                  60

Ser Gly Phe Gly Thr His Phe Thr Leu Thr Ile Asp Asn Leu Gln Pro
65                  70                  75                  80

Glu Asp Ile Ala Thr Tyr Ser Cys Gln Gln Tyr Asn Asn Tyr Pro Phe
                85                  90                  95

Thr Phe Gly Leu Gly Thr Lys Leu Glu Ile Lys
            100                 105

<210> SEQ ID NO 10
<211> LENGTH: 107
<212> TYPE: PRT
<213> ORGANISM: artificial sequence
<220> FEATURE:
<223> OTHER INFORMATION: T8 humanized light chain variable region

<400> SEQUENCE: 10

Glu Ile Val Met Thr Gln Ser Pro Ser Ser Val Ser Ala Ser Val Gly
1               5                   10                  15
```

Asp Arg Val Thr Ile Thr Cys Arg Thr Ser Gln Ser Ile Ser Ser Tyr
            20                  25                  30

Leu Asn Trp Tyr Gln Leu Arg Pro Gly Arg Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Phe Gly Thr Asp Phe Thr Leu Thr Ile Ser Ser Val Gln Pro
65                  70                  75                  80

Glu Asp Phe Ala Thr Tyr Tyr Cys Gln Gln Ala Lys Ser Tyr Pro Leu
                85                  90                  95

Thr Phe Gly Gly Gly Thr Lys Val Asp Ile Lys
            100                 105

<210> SEQ ID NO 11
<211> LENGTH: 108
<212> TYPE: PRT
<213> ORGANISM: artificial sequence
<220> FEATURE:
<223> OTHER INFORMATION: T1 humanized light chain variable region

<400> SEQUENCE: 11

Asp Ile Val Met Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Val Trp Tyr Gln Gln Lys Pro Gly Lys Ala Pro Lys Leu Leu Ile
        35                  40                  45

Tyr Ser Ala Ser Val Leu Gln Ser Gly Val Pro Ser Arg Phe Ser Gly
    50                  55                  60

Arg Gly Tyr Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Ser Ile Pro Pro
                85                  90                  95

Val Thr Phe Gly Gly Gly Thr Lys Val Glu Ile Lys
            100                 105

<210> SEQ ID NO 12
<211> LENGTH: 107
<212> TYPE: PRT
<213> ORGANISM: artificial sequence
<220> FEATURE:
<223> OTHER INFORMATION: T36 humanized light chain variable region

<400> SEQUENCE: 12

Asn Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Arg Pro Gly Lys Ala Pro Gln Leu Leu Ile
        35                  40                  45

Tyr Gly Ala Ser Asn Leu Glu Arg Gly Val Pro Ser Arg Phe Ser Gly
    50                  55                  60

Ser Gly Phe Gly Thr Asp Phe Thr Leu Thr Ile Ser Ser Val Gln Pro
65                  70                  75                  80

Glu Asp Phe Ala Thr Tyr Tyr Cys Gln Gln Ala Lys Ser Tyr Pro Leu
                85                  90                  95

Thr Phe Gly Gly Gly Thr Lys Val Glu Ile Lys
            100                 105

-continued

<210> SEQ ID NO 13
<211> LENGTH: 107
<212> TYPE: PRT
<213> ORGANISM: artificial sequence
<220> FEATURE:
<223> OTHER INFORMATION: T57 humanized light chain variable region

<400> SEQUENCE: 13

```
Glu Ile Val Met Thr Gln Ser Pro Ser Ser Leu Ser Ala Ser Val Gly
1               5                   10                  15

Asp Arg Val Thr Ile Ser Cys Arg Thr Ser Gln Thr Ile Arg His Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Lys Thr Gly Val Pro Ser Arg Phe Ser Gly
    50                  55                  60

Ser Gly Ser Gly Thr Ser Phe Thr Leu Thr Ile Ser Ser Leu Gln Pro
65                  70                  75                  80

Asp Asp Phe Ala Thr Tyr Tyr Cys Gln Gln Ser Tyr Ser Thr Pro Arg
                85                  90                  95

Thr Phe Gly Gln Gly Thr Lys Val Glu Ile Lys
            100                 105
```

<210> SEQ ID NO 14
<211> LENGTH: 107
<212> TYPE: PRT
<213> ORGANISM: artificial sequence
<220> FEATURE:
<223> OTHER INFORMATION: T10 humanized light chain variable region

<400> SEQUENCE: 14

```
Glu Ile Val Leu Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Ile Pro Gly Lys Ala Pro Arg Ile Leu Ile
        35                  40                  45

Ser Ser Ala Ser Ile Leu Gln Ser Gly Ala Pro Ser Arg Phe Ser Gly
    50                  55                  60

Ser Gly Phe Gly Thr Asp Phe Thr Leu Thr Ile Ser Ser Val Gln Pro
65                  70                  75                  80

Glu Asp Phe Ala Thr Tyr Tyr Cys Gln Gln Ala Lys Ser Tyr Pro Leu
                85                  90                  95

Thr Phe Gly Gly Gly Thr Lys Leu Glu Ile Lys
            100                 105
```

<210> SEQ ID NO 15
<211> LENGTH: 107
<212> TYPE: PRT
<213> ORGANISM: artificial sequence
<220> FEATURE:
<223> OTHER INFORMATION: T34 humanized light chain variable region

<400> SEQUENCE: 15

```
Val Ile Trp Met Thr Gln Ser Pro Ser Ser Val Ser Ala Ser Val Gly
1               5                   10                  15

Asp Arg Val Thr Ile Thr Cys Arg Ala Ser Gln Ala Ile Asn Gly Trp
            20                  25                  30
```

-continued

```
Leu Ala Trp Tyr Gln Gln Lys Pro Gly Lys Ala Pro Arg Ile Leu Ile
        35                  40                  45

Tyr Ser Ala Ser Thr Leu Gln Thr Gly Ala Pro Ser Arg Phe Ser Gly
        50                  55                  60

Ser Gly Phe Gly Thr Asp Phe Thr Leu Thr Ile Ser Ser Val Gln Pro
65                  70                  75                  80

Glu Asp Phe Ala Thr Tyr Tyr Cys Gln Gln Ala Lys Ser Tyr Pro Leu
                85                  90                  95

Thr Phe Gly Gly Gly Thr Lys Val Glu Ile Lys
            100                 105

<210> SEQ ID NO 16
<211> LENGTH: 107
<212> TYPE: PRT
<213> ORGANISM: artificial sequence
<220> FEATURE:
<223> OTHER INFORMATION: T56 humanized light chain variable region

<400> SEQUENCE: 16

Asp Ile Val Met Thr Gln Ser Pro Ser Thr Leu Ser Ala Ser Val Gly
1               5                   10                  15

Asp Arg Val Thr Ile Ile Cys Arg Ala Ser Gln Ser Ile Gly Pro Trp
            20                  25                  30

Leu Ala Trp Tyr Gln Gln Lys Ser Gly Lys Ala Pro Lys Leu Leu Ile
        35                  40                  45

Tyr Gly Ala Ser Asn Leu Gln Ser Gly Val Pro Ser Arg Phe Ser Gly
        50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Gln Gln Thr Ser Ser Ala Pro Phe
                85                  90                  95

Thr Phe Gly Pro Gly Thr Lys Val Asp Ile Lys
            100                 105

<210> SEQ ID NO 17
<211> LENGTH: 107
<212> TYPE: PRT
<213> ORGANISM: artificial sequence
<220> FEATURE:
<223> OTHER INFORMATION: T3 humanized light chain variable region

<400> SEQUENCE: 17

Asp Ile Val Met Thr Gln Ser Pro Ser Ser Val Ser Ala Ser Val Gly
1               5                   10                  15

Asp Arg Val Ser Ile Thr Cys Arg Ala Ser Glu His Ile Asn Gly Trp
            20                  25                  30

Leu Ala Trp Tyr Gln Gln Ile Pro Gly Lys Ala Pro Arg Ile Leu Ile
        35                  40                  45

Ser Ser Ala Ser Ile Leu Gln Ser Gly Ala Pro Ser Arg Phe Ser Gly
        50                  55                  60

Ser Gly Phe Gly Thr Asp Phe Thr Leu Thr Ile Ser Ser Val Gln Pro
65                  70                  75                  80

Glu Asp Phe Ala Thr Tyr Tyr Cys Gln Gln Ala Lys Ser Tyr Pro Leu
                85                  90                  95

Thr Phe Gly Gly Gly Thr Lys Val Glu Ile Lys
            100                 105

<210> SEQ ID NO 18
```

```
<211> LENGTH: 107
<212> TYPE: PRT
<213> ORGANISM: artificial sequence
<220> FEATURE:
<223> OTHER INFORMATION: T11 humanized light chain variable region

<400> SEQUENCE: 18

Ala Ile Arg Met Thr Gln Ser Pro Ser Ser Leu Ser Ala Ser Val Gly
1               5                   10                  15

Asp Arg Val Thr Ile Thr Cys Arg Ala Ser Arg Ser Ile Ser Thr Tyr
            20                  25                  30

Leu His Trp Tyr Gln Gln Lys Ala Gly Lys Ala Pro Lys Leu Leu Ile
        35                  40                  45

Tyr Ser Ala Tyr Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Val Glu Ile Lys
            100                 105

<210> SEQ ID NO 19
<211> LENGTH: 107
<212> TYPE: PRT
<213> ORGANISM: artificial sequence
<220> FEATURE:
<223> OTHER INFORMATION: T28 humanized light chain variable region

<400> SEQUENCE: 19

Asp Ile Gln Met Thr Gln Ser Pro Ser Ser Leu Ser Ala Ser Leu Gly
1               5                   10                  15

Glu Met Val Thr Ile Thr Cys Arg Ala Ser Glu Ser Ile His Ser Tyr
            20                  25                  30

Leu Asn Trp Tyr Gln Gln Lys Pro Gly Lys Ala Pro Asn Leu Leu Ile
        35                  40                  45

Tyr Asp Ala Ser Asn Leu Glu Ser Gly Val Pro Ser Arg Phe Ser Gly
    50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Gly Pro Pro Ile
                85                  90                  95

Thr Phe Gly Gln Gly Thr Arg Leu Glu Ile Lys
            100                 105

<210> SEQ ID NO 20
<211> LENGTH: 107
<212> TYPE: PRT
<213> ORGANISM: artificial sequence
<220> FEATURE:
<223> OTHER INFORMATION: T43 humanized light chain variable region

<400> SEQUENCE: 20

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Ser Ala
            20                  25                  30

Leu Ala Trp Tyr Gln Gln Lys Pro Gly Lys Ala Pro Lys Leu Leu Ile
        35                  40                  45
```

-continued

```
Tyr Asp Ala Ser Asn Leu Gln Ser Gly Val Pro Ser Arg Phe Ser Gly
    50              55              60

Ser Gly Ser Gly Thr Asp Phe Thr Leu Thr Ile Ser Asp Val Gln Ala
65              70              75              80

Glu Asp Phe Gly Thr Tyr Tyr Cys Gln Gln Ser Phe Gly Pro Pro Arg
                85              90              95

Thr Phe Gly Gln Gly Thr Arg Leu Glu Ile Lys
            100             105
```

```
<210> SEQ ID NO 21
<211> LENGTH: 107
<212> TYPE: PRT
<213> ORGANISM: artificial sequence
<220> FEATURE:
<223> OTHER INFORMATION: T59 humanized light chain variable region

<400> SEQUENCE: 21
```

```
Glu Ile Val Met Thr Gln Ser Pro Ser Ser Leu Ser Ala Ser Val Gly
1               5               10              15

Asp Arg Val Thr Ile Thr Cys Gln Ala Ser Gln His Ile Ser Asn Lys
                20              25              30

Leu Asn Trp Tyr Gln Gln Lys Pro Gly Lys Ala Pro Lys Leu Leu Ile
        35              40              45

Tyr Asp Ala Ser Asn Leu Glu Thr Gly Val Pro Ser Arg Phe Ser Gly
    50              55              60

Ser Gly Tyr Gly Thr Asp Phe Thr Phe Thr Val Ser Ser Leu Gln Pro
65              70              75              80

Glu Asp Ile Ala Thr Tyr Tyr Cys Gln Gln Tyr Asp Asn Leu Pro Ile
                85              90              95

Thr Phe Gly Gln Gly Thr Arg Leu Glu Ile Lys
            100             105
```

```
<210> SEQ ID NO 22
<211> LENGTH: 107
<212> TYPE: PRT
<213> ORGANISM: artificial sequence
<220> FEATURE:
<223> OTHER INFORMATION: T31 humanized light chain variable region

<400> SEQUENCE: 22
```

```
Ala Ile Gln Met Thr Gln Ser Pro Ala Thr Leu Ser Leu Ser Pro Gly
1               5               10              15

Gln Arg Ala Thr Leu Ser Cys Arg Ala Ser Gln Ser Val Ser Asn Tyr
                20              25              30

Leu Ala Trp Tyr Gln Gln Lys Pro Gly Gln Ala Pro Arg Leu Leu Ile
        35              40              45

Tyr Asp Val Ser Asn Arg Ala Ser Gly Ile Pro Ala Arg Phe Ser Gly
    50              55              60

Ser Gly Ser Gly Thr Asp Phe Thr Leu Thr Ile Ser Ser Leu Glu Pro
65              70              75              80

Glu Asp Phe Ala Ile Tyr Tyr Cys Gln Gln Arg Ser Asn Trp Pro Leu
                85              90              95

Thr Phe Gly Gln Gly Thr Lys Val Asp Ile Lys
            100             105
```

```
<210> SEQ ID NO 23
<211> LENGTH: 107
<212> TYPE: PRT
<213> ORGANISM: artificial sequence
```

```
<220> FEATURE:
<223> OTHER INFORMATION: T22 humanized light chain variable region

<400> SEQUENCE: 23

Ala Ile Gln Met Thr Gln Ser Pro Ala Ser Leu Ser Ala Ser Leu Gly
1               5                   10                  15

Asp Arg Ile Thr Ile Thr Cys Arg Thr Ser Gln Thr Val Ala Gly Tyr
            20                  25                  30

Leu Asn Trp Tyr Gln Gln Thr Pro Gly Asn Ala Pro Lys Leu Leu Ile
        35                  40                  45

Tyr Ser Ala Ser Asn Leu Gln Ser Gly Val Pro Ser Arg Phe Ser Gly
    50                  55                  60

Ser Gly Ser Gly Arg Asp Phe Ser Leu Thr Ile Ser Ser Leu Gln Ser
65                  70                  75                  80

Glu Asp Ser Ala Thr Tyr Tyr Cys Gln His Ser Tyr Ser Thr Pro Tyr
                85                  90                  95

Thr Phe Gly Gln Gly Thr Lys Val Glu Ile Lys
            100                 105

<210> SEQ ID NO 24
<211> LENGTH: 107
<212> TYPE: PRT
<213> ORGANISM: artificial sequence
<220> FEATURE:
<223> OTHER INFORMATION: T26 humanized light chain variable region

<400> SEQUENCE: 24

Asp Val Val Met Thr Gln Ser Pro Ser Ser Leu Ser Ala Ser Val Gly
1               5                   10                  15

Glu Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Arg Ala Thr Gly Ile Pro His Arg Tyr Ser Gly
    50                  55                  60

Ser Gly Ser Gly Thr Val Phe Thr Leu Thr Ile Ser Arg Leu Glu Pro
65                  70                  75                  80

Glu Asp Phe Ala Thr Tyr Tyr Cys Gln Gln Phe His Ser Tyr Pro Ile
                85                  90                  95

Thr Phe Gly Gln Gly Thr Arg Leu Glu Ile Lys
            100                 105

<210> SEQ ID NO 25
<211> LENGTH: 107
<212> TYPE: PRT
<213> ORGANISM: artificial sequence
<220> FEATURE:
<223> OTHER INFORMATION: T32 humanized light chain variable region

<400> SEQUENCE: 25

Asp Val Val Met Thr Gln Ser Pro Gly Thr Leu Ser Leu Ser Pro Gly
1               5                   10                  15

Glu Arg Ala Thr Leu Ser Cys Ser Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Thr Ser Ser Arg Ala Thr Gly Val Pro Ala Arg Phe Ser Gly
    50                  55                  60
```

-continued

```
Ser Gly Ser Gly Thr Glu Phe Thr Leu Thr Ile Ser Ser Leu Gln Ser
65                  70                  75                  80

Glu Asp Phe Ala Ala Tyr Tyr Cys Gln Gln Tyr Asn Ser Trp Pro Leu
                85                  90                  95

Thr Phe Gly Gly Gly Thr Lys Val Glu Ile Lys
            100                 105

<210> SEQ ID NO 26
<211> LENGTH: 108
<212> TYPE: PRT
<213> ORGANISM: artificial sequence
<220> FEATURE:
<223> OTHER INFORMATION: T33 humanized light chain variable region

<400> SEQUENCE: 26

Asp Val Val Met Thr Gln Ser Pro Ala Thr Leu Ser Val Pro Pro Gly
1               5                   10                  15

Asp Arg Ala Thr Leu Ser Cys Arg Ala Ser Gln Ser Val Ser Ser Arg
                20                  25                  30

Leu Ala Trp Tyr Gln Gln Lys Pro Gly Gln Ala Pro Lys Leu Leu Ile
            35                  40                  45

Tyr Gly Ala Ser Thr Arg Ala Thr Gly Ile Pro Ala Arg Phe Ser Gly
        50                  55                  60

Ser Trp Ser Gly Thr Glu Phe Thr Leu Thr Val Ser Ser Leu Gln Ser
65                  70                  75                  80

Glu Asp Ser Ala Val Tyr Tyr Cys Gln Gln Tyr Asn Asp Trp Pro Arg
                85                  90                  95

Tyr Thr Phe Gly Gln Gly Thr Lys Leu Glu Ile Lys
            100                 105

<210> SEQ ID NO 27
<211> LENGTH: 107
<212> TYPE: PRT
<213> ORGANISM: artificial sequence
<220> FEATURE:
<223> OTHER INFORMATION: T29 humanized light chain variable region

<400> SEQUENCE: 27

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
                20                  25                  30

Leu Asn Trp Tyr Gln Gln Lys Pro Gly Glu Ala Pro Lys Leu Leu Val
            35                  40                  45

Tyr Gly Ala Ser Asn Leu Gln Arg Gly Val Pro Pro Gly Phe Arg Gly
        50                  55                  60

Ser Gly Ser Gly Thr Asp Phe Thr Leu Thr Ile Asn Asn Leu Gln Pro
65                  70                  75                  80

Glu Asp Phe Ala Thr Tyr Tyr Cys Gln Gln Ser Ser Thr Ser Pro Ile
                85                  90                  95

Thr Phe Gly Gln Gly Thr Arg Leu Glu Ile Lys
            100                 105

<210> SEQ ID NO 28
<211> LENGTH: 5
<212> TYPE: PRT
<213> ORGANISM: artificial sequence
<220> FEATURE:
<223> OTHER INFORMATION: humanized heavy chain CDR1
```

```
<400> SEQUENCE: 28

Gly Tyr Tyr Met His
1               5

<210> SEQ ID NO 29
<211> LENGTH: 16
<212> TYPE: PRT
<213> ORGANISM: artificial sequence
<220> FEATURE:
<223> OTHER INFORMATION: humanized heavy chain CDR2

<400> SEQUENCE: 29

Glu Ile Asn Pro Ser Thr Gly Asp Thr Thr Tyr Asn Gln Lys Phe Lys
1               5                   10                  15

<210> SEQ ID NO 30
<211> LENGTH: 10
<212> TYPE: PRT
<213> ORGANISM: artificial sequence
<220> FEATURE:
<223> OTHER INFORMATION: humanized heavy chain CDR3

<400> SEQUENCE: 30

Glu Lys Arg Asp Asp Gly Val Phe Ala Tyr
1               5                   10

<210> SEQ ID NO 31
<211> LENGTH: 11
<212> TYPE: PRT
<213> ORGANISM: artificial sequence
<220> FEATURE:
<223> OTHER INFORMATION: T2 light chain CDR1

<400> SEQUENCE: 31

Arg Ala Ser Gln Gly Ile Ser Ser Tyr Leu Val
1               5                   10

<210> SEQ ID NO 32
<211> LENGTH: 7
<212> TYPE: PRT
<213> ORGANISM: artificial sequence
<220> FEATURE:
<223> OTHER INFORMATION: T2 light chain CDR2

<400> SEQUENCE: 32

Ser Ala Ser Val Leu Gln Ser
1               5

<210> SEQ ID NO 33
<211> LENGTH: 10
<212> TYPE: PRT
<213> ORGANISM: artificial sequence
<220> FEATURE:
<223> OTHER INFORMATION: T2 light chain CDR3

<400> SEQUENCE: 33

Gln Gln Ser Phe Ser Ile Pro Pro Val Thr
1               5                   10

<210> SEQ ID NO 34
<211> LENGTH: 11
<212> TYPE: PRT
<213> ORGANISM: artificial sequence
<220> FEATURE:
<223> OTHER INFORMATION: T7 light chain CDR1

<400> SEQUENCE: 34
```

```
Arg Ala Ser Gln Ser Ile Ser Ser Trp Leu Ala
1               5                   10

<210> SEQ ID NO 35
<211> LENGTH: 7
<212> TYPE: PRT
<213> ORGANISM: artificial sequence
<220> FEATURE:
<223> OTHER INFORMATION: T7 light chain CDR2

<400> SEQUENCE: 35

Asp Ala Ser Asn Leu Ala Ser
1               5

<210> SEQ ID NO 36
<211> LENGTH: 9
<212> TYPE: PRT
<213> ORGANISM: artificial sequence
<220> FEATURE:
<223> OTHER INFORMATION: T7 light chain CDR3

<400> SEQUENCE: 36

Gln Gln Tyr Asn Asn Tyr Pro Phe Thr
1               5

<210> SEQ ID NO 37
<211> LENGTH: 11
<212> TYPE: PRT
<213> ORGANISM: artificial sequence
<220> FEATURE:
<223> OTHER INFORMATION: T8 light chain CDR1

<400> SEQUENCE: 37

Arg Thr Ser Gln Ser Ile Ser Ser Tyr Leu Asn
1               5                   10

<210> SEQ ID NO 38
<211> LENGTH: 7
<212> TYPE: PRT
<213> ORGANISM: artificial sequence
<220> FEATURE:
<223> OTHER INFORMATION: T8 light chain CDR2

<400> SEQUENCE: 38

Ala Ala Ser Asn Leu Gln Ser
1               5

<210> SEQ ID NO 39
<211> LENGTH: 9
<212> TYPE: PRT
<213> ORGANISM: artificial sequence
<220> FEATURE:
<223> OTHER INFORMATION: T8 light chain CDR3

<400> SEQUENCE: 39

Gln Gln Ala Lys Ser Tyr Pro Leu Thr
1               5

<210> SEQ ID NO 40
<211> LENGTH: 11
<212> TYPE: PRT
<213> ORGANISM: artificial sequence
<220> FEATURE:
<223> OTHER INFORMATION: T1 light chain CDR1

<400> SEQUENCE: 40
```

-continued

```
Arg Ala Ser Gln Gly Ile Ser Ser Tyr Leu Val
1               5                   10

<210> SEQ ID NO 41
<211> LENGTH: 7
<212> TYPE: PRT
<213> ORGANISM: artificial sequence
<220> FEATURE:
<223> OTHER INFORMATION: T1 light chain CDR2

<400> SEQUENCE: 41

Ser Ala Ser Val Leu Gln Ser
1               5

<210> SEQ ID NO 42
<211> LENGTH: 10
<212> TYPE: PRT
<213> ORGANISM: artificial sequence
<220> FEATURE:
<223> OTHER INFORMATION: T1 light chain CDR3

<400> SEQUENCE: 42

Gln Gln Ser Phe Ser Ile Pro Pro Val Thr
1               5                   10

<210> SEQ ID NO 43
<211> LENGTH: 11
<212> TYPE: PRT
<213> ORGANISM: artificial sequence
<220> FEATURE:
<223> OTHER INFORMATION: T36 light chain CDR1

<400> SEQUENCE: 43

Gln Ala Ser Gln Asp Ile Ser Asn Tyr Leu Asn
1               5                   10

<210> SEQ ID NO 44
<211> LENGTH: 7
<212> TYPE: PRT
<213> ORGANISM: artificial sequence
<220> FEATURE:
<223> OTHER INFORMATION: T36 light chain CDR2

<400> SEQUENCE: 44

Gly Ala Ser Asn Leu Glu Arg
1               5

<210> SEQ ID NO 45
<211> LENGTH: 9
<212> TYPE: PRT
<213> ORGANISM: artificial sequence
<220> FEATURE:
<223> OTHER INFORMATION: T36 light chain CDR3

<400> SEQUENCE: 45

Gln Gln Ala Lys Ser Tyr Pro Leu Thr
1               5

<210> SEQ ID NO 46
<211> LENGTH: 11
<212> TYPE: PRT
<213> ORGANISM: artificial sequence
<220> FEATURE:
<223> OTHER INFORMATION: T57 light chain CDR1

<400> SEQUENCE: 46

Arg Thr Ser Gln Thr Ile Arg His Tyr Leu Asn
```

-continued

```
1               5                   10
```

```
<210> SEQ ID NO 47
<211> LENGTH: 7
<212> TYPE: PRT
<213> ORGANISM: artificial sequence
<220> FEATURE:
<223> OTHER INFORMATION: T57 light chain CDR2

<400> SEQUENCE: 47

Asp Ala Ser Asn Leu Lys Thr
1               5

<210> SEQ ID NO 48
<211> LENGTH: 9
<212> TYPE: PRT
<213> ORGANISM: artificial sequence
<220> FEATURE:
<223> OTHER INFORMATION: T57 light chain CDR3

<400> SEQUENCE: 48

Gln Gln Ser Tyr Ser Thr Pro Arg Thr
1               5

<210> SEQ ID NO 49
<211> LENGTH: 11
<212> TYPE: PRT
<213> ORGANISM: artificial sequence
<220> FEATURE:
<223> OTHER INFORMATION: T10 light chain CDR1

<400> SEQUENCE: 49

Arg Ala Ser Gln Ser Ile Ser Ser Trp Leu Ala
1               5                   10

<210> SEQ ID NO 50
<211> LENGTH: 7
<212> TYPE: PRT
<213> ORGANISM: artificial sequence
<220> FEATURE:
<223> OTHER INFORMATION: T10 light chain CDR2

<400> SEQUENCE: 50

Ser Ala Ser Ile Leu Gln Ser
1               5

<210> SEQ ID NO 51
<211> LENGTH: 9
<212> TYPE: PRT
<213> ORGANISM: artificial sequence
<220> FEATURE:
<223> OTHER INFORMATION: T10 light chain CDR3

<400> SEQUENCE: 51

Gln Gln Ala Lys Ser Tyr Pro Leu Thr
1               5

<210> SEQ ID NO 52
<211> LENGTH: 11
<212> TYPE: PRT
<213> ORGANISM: artificial sequence
<220> FEATURE:
<223> OTHER INFORMATION: T34 light chain CDR1

<400> SEQUENCE: 52

Arg Ala Ser Gln Ala Ile Asn Gly Trp Leu Ala
1               5                   10
```

-continued

```
<210> SEQ ID NO 53
<211> LENGTH: 7
<212> TYPE: PRT
<213> ORGANISM: artificial sequence
<220> FEATURE:
<223> OTHER INFORMATION: T34 light chain CDR2

<400> SEQUENCE: 53

Ser Ala Ser Thr Leu Gln Thr
1               5

<210> SEQ ID NO 54
<211> LENGTH: 9
<212> TYPE: PRT
<213> ORGANISM: artificial sequence
<220> FEATURE:
<223> OTHER INFORMATION: T34 light chain CDR3

<400> SEQUENCE: 54

Gln Gln Ala Lys Ser Tyr Pro Leu Thr
1               5

<210> SEQ ID NO 55
<211> LENGTH: 11
<212> TYPE: PRT
<213> ORGANISM: artificial sequence
<220> FEATURE:
<223> OTHER INFORMATION: T56 light chain CDR1

<400> SEQUENCE: 55

Arg Ala Ser Gln Ser Ile Gly Pro Trp Leu Ala
1               5                   10

<210> SEQ ID NO 56
<211> LENGTH: 7
<212> TYPE: PRT
<213> ORGANISM: artificial sequence
<220> FEATURE:
<223> OTHER INFORMATION: T56 light chain CDR2

<400> SEQUENCE: 56

Gly Ala Ser Asn Leu Gln Ser
1               5

<210> SEQ ID NO 57
<211> LENGTH: 9
<212> TYPE: PRT
<213> ORGANISM: artificial sequence
<220> FEATURE:
<223> OTHER INFORMATION: T56 light chain CDR3

<400> SEQUENCE: 57

Gln Gln Thr Ser Ser Ala Pro Phe Thr
1               5

<210> SEQ ID NO 58
<211> LENGTH: 11
<212> TYPE: PRT
<213> ORGANISM: artificial sequence
<220> FEATURE:
<223> OTHER INFORMATION: T3 light chain CDR1

<400> SEQUENCE: 58

Arg Ala Ser Glu His Ile Asn Gly Trp Leu Ala
1               5                   10
```

<210> SEQ ID NO 59
<211> LENGTH: 7
<212> TYPE: PRT
<213> ORGANISM: artificial sequence
<220> FEATURE:
<223> OTHER INFORMATION: T3 light chain CDR2

<400> SEQUENCE: 59

Ser Ala Ser Ile Leu Gln Ser
1               5

<210> SEQ ID NO 60
<211> LENGTH: 9
<212> TYPE: PRT
<213> ORGANISM: artificial sequence
<220> FEATURE:
<223> OTHER INFORMATION: T3 light chain CDR3

<400> SEQUENCE: 60

Gln Gln Ala Lys Ser Tyr Pro Leu Thr
1               5

<210> SEQ ID NO 61
<211> LENGTH: 11
<212> TYPE: PRT
<213> ORGANISM: artificial sequence
<220> FEATURE:
<223> OTHER INFORMATION: T11 light chain CDR1

<400> SEQUENCE: 61

Arg Ala Ser Arg Ser Ile Ser Thr Tyr Leu His
1               5                   10

<210> SEQ ID NO 62
<211> LENGTH: 7
<212> TYPE: PRT
<213> ORGANISM: artificial sequence
<220> FEATURE:
<223> OTHER INFORMATION: T11 light chain CDR2

<400> SEQUENCE: 62

Ser Ala Tyr Asn Leu Gln Ser
1               5

<210> SEQ ID NO 63
<211> LENGTH: 9
<212> TYPE: PRT
<213> ORGANISM: artificial sequence
<220> FEATURE:
<223> OTHER INFORMATION: T11 light chain CDR3

<400> SEQUENCE: 63

Gln Gln Ser Tyr Ser Thr Pro Tyr Thr
1               5

<210> SEQ ID NO 64
<211> LENGTH: 11
<212> TYPE: PRT
<213> ORGANISM: artificial sequence
<220> FEATURE:
<223> OTHER INFORMATION: T28 light chain CDR1

<400> SEQUENCE: 64

Arg Ala Ser Glu Ser Ile His Ser Tyr Leu Asn
1               5                   10

```
<210> SEQ ID NO 65
<211> LENGTH: 7
<212> TYPE: PRT
<213> ORGANISM: artificial sequence
<220> FEATURE:
<223> OTHER INFORMATION: T28 light chain CDR2

<400> SEQUENCE: 65

Asp Ala Ser Asn Leu Glu Ser
1               5

<210> SEQ ID NO 66
<211> LENGTH: 9
<212> TYPE: PRT
<213> ORGANISM: artificial sequence
<220> FEATURE:
<223> OTHER INFORMATION: T28 light chain CDR3

<400> SEQUENCE: 66

Gln Gln Ser Tyr Gly Pro Pro Ile Thr
1               5

<210> SEQ ID NO 67
<211> LENGTH: 11
<212> TYPE: PRT
<213> ORGANISM: artificial sequence
<220> FEATURE:
<223> OTHER INFORMATION: T43 light chain CDR1

<400> SEQUENCE: 67

Arg Ala Ser Gln Gly Ile Arg Ser Ala Leu Ala
1               5                   10

<210> SEQ ID NO 68
<211> LENGTH: 7
<212> TYPE: PRT
<213> ORGANISM: artificial sequence
<220> FEATURE:
<223> OTHER INFORMATION: T43 light chain CDR2

<400> SEQUENCE: 68

Asp Ala Ser Asn Leu Gln Ser
1               5

<210> SEQ ID NO 69
<211> LENGTH: 9
<212> TYPE: PRT
<213> ORGANISM: artificial sequence
<220> FEATURE:
<223> OTHER INFORMATION: T43 light chain CDR3

<400> SEQUENCE: 69

Gln Gln Ser Phe Gly Pro Pro Arg Thr
1               5

<210> SEQ ID NO 70
<211> LENGTH: 11
<212> TYPE: PRT
<213> ORGANISM: artificial sequence
<220> FEATURE:
<223> OTHER INFORMATION: T59 light chain CDR1

<400> SEQUENCE: 70

Gln Ala Ser Gln His Ile Ser Asn Lys Leu Asn
1               5                   10

<210> SEQ ID NO 71
```

-continued

```
<211> LENGTH: 7
<212> TYPE: PRT
<213> ORGANISM: artificial sequence
<220> FEATURE:
<223> OTHER INFORMATION: T59 light chain CDR2

<400> SEQUENCE: 71

Asp Ala Ser Asn Leu Glu Thr
1               5

<210> SEQ ID NO 72
<211> LENGTH: 9
<212> TYPE: PRT
<213> ORGANISM: artificial sequence
<220> FEATURE:
<223> OTHER INFORMATION: T59 light chain CDR3

<400> SEQUENCE: 72

Gln Gln Tyr Asp Asn Leu Pro Ile Thr
1               5

<210> SEQ ID NO 73
<211> LENGTH: 11
<212> TYPE: PRT
<213> ORGANISM: artificial sequence
<220> FEATURE:
<223> OTHER INFORMATION: T31 light chain CDR1

<400> SEQUENCE: 73

Arg Ala Ser Gln Ser Val Ser Asn Tyr Leu Ala
1               5                   10

<210> SEQ ID NO 74
<211> LENGTH: 7
<212> TYPE: PRT
<213> ORGANISM: artificial sequence
<220> FEATURE:
<223> OTHER INFORMATION: T31 light chain CDR2

<400> SEQUENCE: 74

Asp Val Ser Asn Arg Ala Ser
1               5

<210> SEQ ID NO 75
<211> LENGTH: 9
<212> TYPE: PRT
<213> ORGANISM: artificial sequence
<220> FEATURE:
<223> OTHER INFORMATION: T31 light chain CDR3

<400> SEQUENCE: 75

Gln Gln Arg Ser Asn Trp Pro Leu Thr
1               5

<210> SEQ ID NO 76
<211> LENGTH: 11
<212> TYPE: PRT
<213> ORGANISM: artificial sequence
<220> FEATURE:
<223> OTHER INFORMATION: T22 light chain CDR1

<400> SEQUENCE: 76

Arg Thr Ser Gln Thr Val Ala Gly Tyr Leu Asn
1               5                   10

<210> SEQ ID NO 77
<211> LENGTH: 7
```

-continued

```
<212> TYPE: PRT
<213> ORGANISM: artificial sequence
<220> FEATURE:
<223> OTHER INFORMATION: T22 light chain CDR2

<400> SEQUENCE: 77

Ser Ala Ser Asn Leu Gln Ser
1               5

<210> SEQ ID NO 78
<211> LENGTH: 9
<212> TYPE: PRT
<213> ORGANISM: artificial sequence
<220> FEATURE:
<223> OTHER INFORMATION: T22 light chain CDR3

<400> SEQUENCE: 78

Gln His Ser Tyr Ser Thr Pro Tyr Thr
1               5

<210> SEQ ID NO 79
<211> LENGTH: 11
<212> TYPE: PRT
<213> ORGANISM: artificial sequence
<220> FEATURE:
<223> OTHER INFORMATION: T26 light chain CDR1

<400> SEQUENCE: 79

Arg Ala Ser Gln Ser Ile Ser Ser Tyr Leu Asn
1               5                   10

<210> SEQ ID NO 80
<211> LENGTH: 7
<212> TYPE: PRT
<213> ORGANISM: artificial sequence
<220> FEATURE:
<223> OTHER INFORMATION: T26 light chain CDR1

<400> SEQUENCE: 80

Ala Ala Ser Ser Arg Ala Thr
1               5

<210> SEQ ID NO 81
<211> LENGTH: 9
<212> TYPE: PRT
<213> ORGANISM: artificial sequence
<220> FEATURE:
<223> OTHER INFORMATION: T26 light chain CDR3

<400> SEQUENCE: 81

Gln Gln Phe His Ser Tyr Pro Ile Thr
1               5

<210> SEQ ID NO 82
<211> LENGTH: 11
<212> TYPE: PRT
<213> ORGANISM: artificial sequence
<220> FEATURE:
<223> OTHER INFORMATION: T32 light chain CDR1

<400> SEQUENCE: 82

Ser Ala Ser Gln Ser Val Ser Ser Asn Leu Ala
1               5                   10

<210> SEQ ID NO 83
<211> LENGTH: 7
<212> TYPE: PRT
```

<213> ORGANISM: artificial sequence
<220> FEATURE:
<223> OTHER INFORMATION: T32 light chain CDR2

<400> SEQUENCE: 83

Gly Thr Ser Ser Arg Ala Thr
1               5

<210> SEQ ID NO 84
<211> LENGTH: 9
<212> TYPE: PRT
<213> ORGANISM: artificial sequence
<220> FEATURE:
<223> OTHER INFORMATION: T32 light chain CDR3

<400> SEQUENCE: 84

Gln Gln Tyr Asn Ser Trp Pro Leu Thr
1               5

<210> SEQ ID NO 85
<211> LENGTH: 11
<212> TYPE: PRT
<213> ORGANISM: artificial sequence
<220> FEATURE:
<223> OTHER INFORMATION: T33 light chain CDR1

<400> SEQUENCE: 85

Arg Ala Ser Gln Ser Val Ser Ser Arg Leu Ala
1               5                   10

<210> SEQ ID NO 86
<211> LENGTH: 7
<212> TYPE: PRT
<213> ORGANISM: artificial sequence
<220> FEATURE:
<223> OTHER INFORMATION: T33 light chain CDR2

<400> SEQUENCE: 86

Gly Ala Ser Thr Arg Ala Thr
1               5

<210> SEQ ID NO 87
<211> LENGTH: 10
<212> TYPE: PRT
<213> ORGANISM: artificial sequence
<220> FEATURE:
<223> OTHER INFORMATION: T33 light chain CDR3

<400> SEQUENCE: 87

Gln Gln Tyr Asn Asp Trp Pro Arg Tyr Thr
1               5                   10

<210> SEQ ID NO 88
<211> LENGTH: 11
<212> TYPE: PRT
<213> ORGANISM: artificial sequence
<220> FEATURE:
<223> OTHER INFORMATION: T29 light chain CDR1

<400> SEQUENCE: 88

Arg Ala Ser Gln Asp Ile Ser Ser Tyr Leu Asn
1               5                   10

<210> SEQ ID NO 89
<211> LENGTH: 7
<212> TYPE: PRT
<213> ORGANISM: artificial sequence
<220> FEATURE:
<223> OTHER INFORMATION: T29 light chain CDR2

<400> SEQUENCE: 89

Gly Ala Ser Asn Leu Gln Arg
1               5

<210> SEQ ID NO 90
<211> LENGTH: 9
<212> TYPE: PRT
<213> ORGANISM: artificial sequence
<220> FEATURE:
<223> OTHER INFORMATION: T29 light chain CDR3

<400> SEQUENCE: 90

Gln Gln Ser Ser Thr Ser Pro Ile Thr
1               5

<210> SEQ ID NO 91
<211> LENGTH: 327
<212> TYPE: PRT
<213> ORGANISM: artificial sequence
<220> FEATURE:
<223> OTHER INFORMATION: heavy chain constant region of chimeric and
      humanized antibody

<400> SEQUENCE: 91

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

```
Ile Ala Val Glu Trp Glu Ser Asn Gly Gln Pro Glu Asn Asn Tyr Lys
            260             265             270

Thr Thr Pro Pro Val Leu Asp Ser Asp Gly Ser Phe Phe Leu Tyr Ser
        275             280             285

Arg Leu Thr Val Asp Lys Ser Arg Trp Gln Glu Gly Asn Val Phe Ser
    290             295             300

Cys Ser Val Met His Glu Ala Leu His Asn His Tyr Thr Gln Lys Ser
305             310             315             320

Leu Ser Leu Ser Leu Gly Lys
            325

<210> SEQ ID NO 92
<211> LENGTH: 107
<212> TYPE: PRT
<213> ORGANISM: artificial sequence
<220> FEATURE:
<223> OTHER INFORMATION: light chain constant region of chimeric and
      humanized antibody

<400> SEQUENCE: 92

Arg Thr Val Ala Ala Pro Ser Val Phe Ile Phe Pro Pro Ser Asp Glu
1           5               10              15

Gln Leu Lys Ser Gly Thr Ala Ser Val Val Cys Leu Leu Asn Asn Phe
            20              25              30

Tyr Pro Arg Glu Ala Lys Val Gln Trp Lys Val Asp Asn Ala Leu Gln
        35              40              45

Ser Gly Asn Ser Gln Glu Ser Val Thr Glu Gln Asp Ser Lys Asp Ser
    50              55              60

Thr Tyr Ser Leu Ser Ser Thr Leu Thr Leu Ser Lys Ala Asp Tyr Glu
65              70              75              80

Lys His Lys Val Tyr Ala Cys Glu Val Thr His Gln Gly Leu Ser Ser
            85              90              95

Pro Val Thr Lys Ser Phe Asn Arg Gly Glu Cys
            100             105
```

Humanized anti–GPC1 antibody

Examination of reaction conditions for conjugates

DAR0   DAR2   DAR4   DAR6   DAR8

| Scale (g) | ADC conc. (mg/ml) | Free drug %w/w/mol | Endotoxin (EU/mg) | ADC Amount (mg) |
|---|---|---|---|---|
| 1.1 | 10 | < 0.06 | < 0.002 | < 0.045 | 960 |

| | Drug Distribution | | | | | | Purity by SEC | | |
|---|---|---|---|---|---|---|---|---|---|
| DAR | D0 (%) | D2 (%) | D4 (%) | D6 (%) | D8 (%) | | HMWS (%) | Monomer (%) | LMWS (%) |
| 4.01 | 7.26 | 15.57 | 59.06 | 5.71 | 12.4 | | 1.43 | 98.57 | ND |

Figure 13
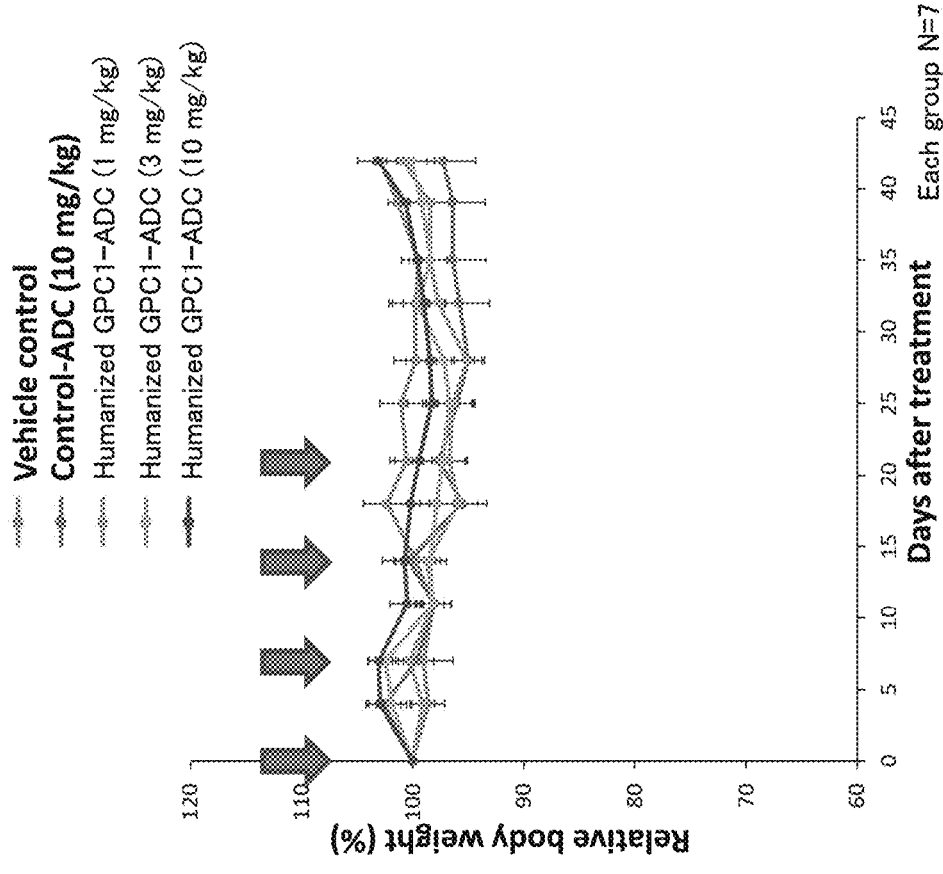
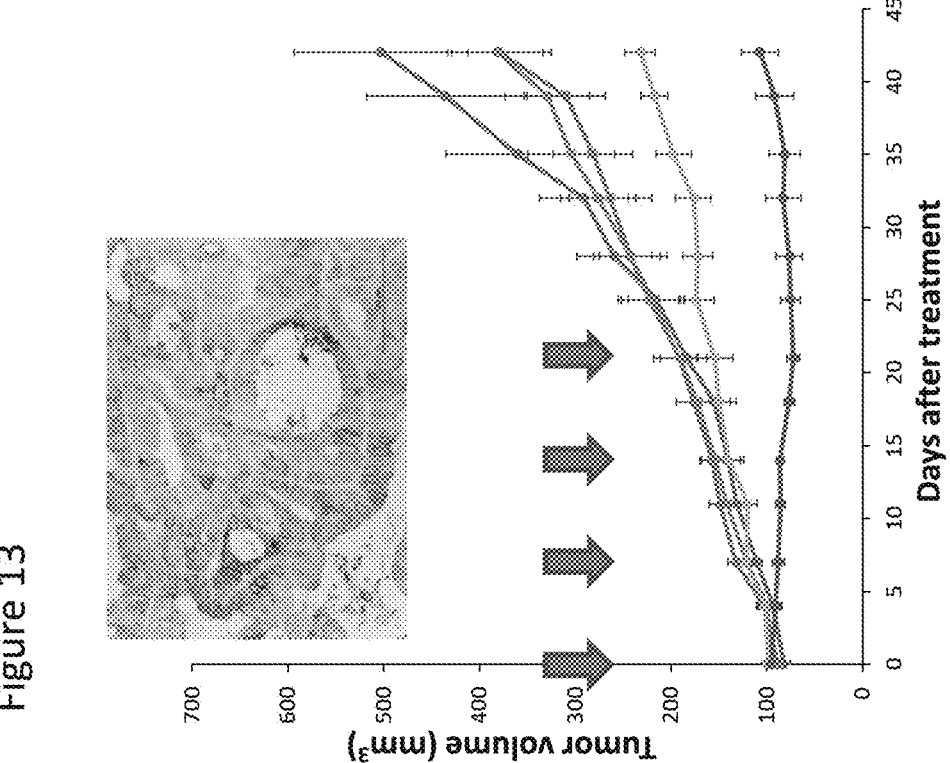

Figure 14
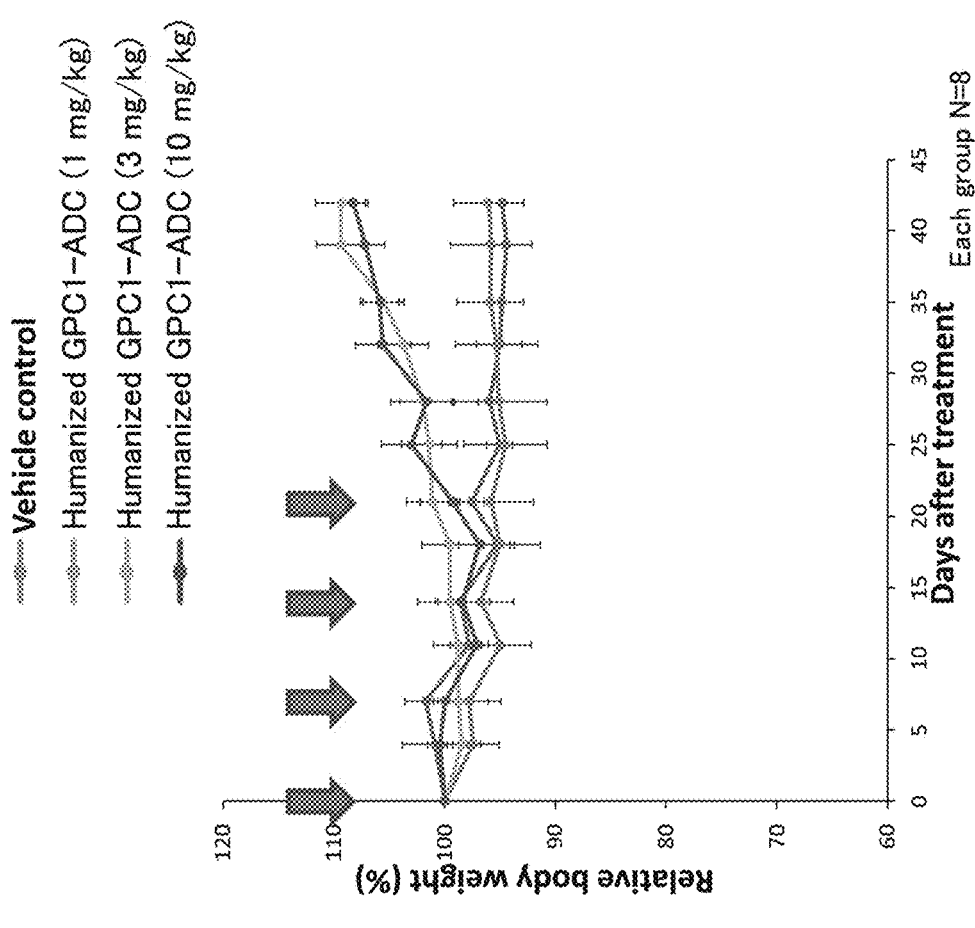
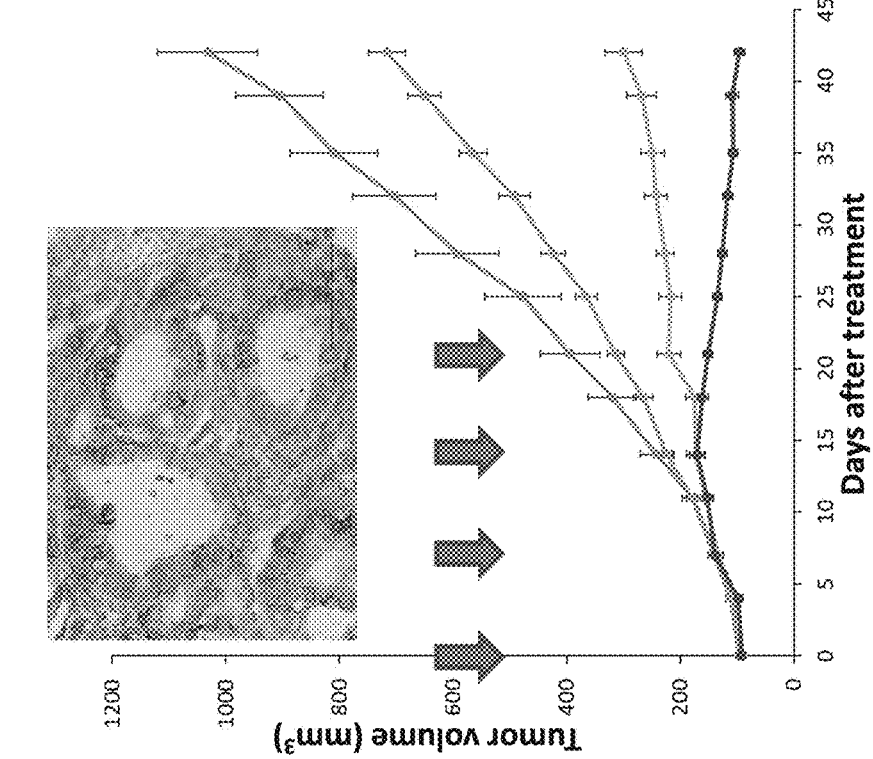

Figure 16
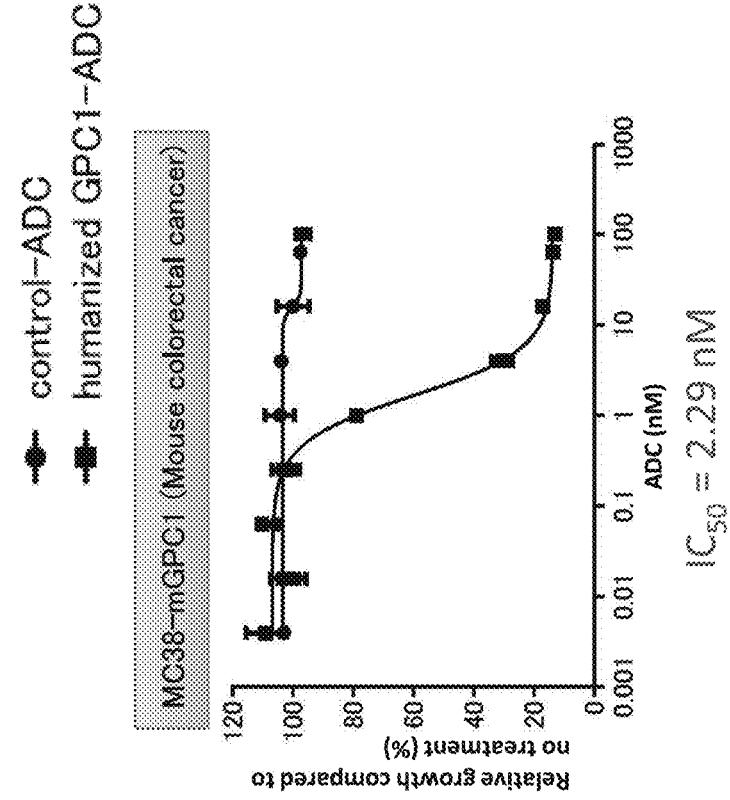
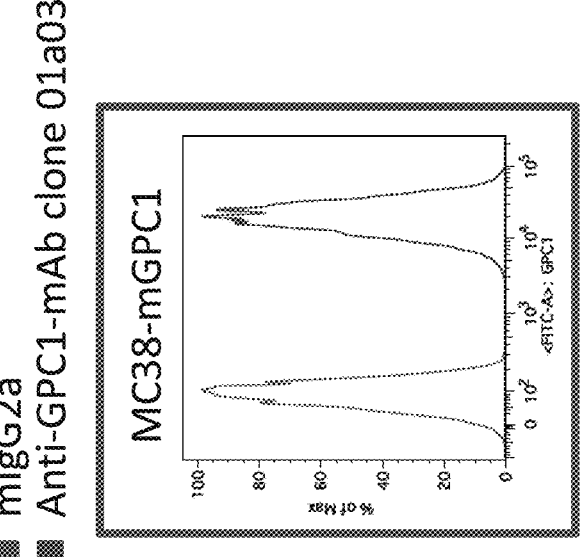

Figure 21

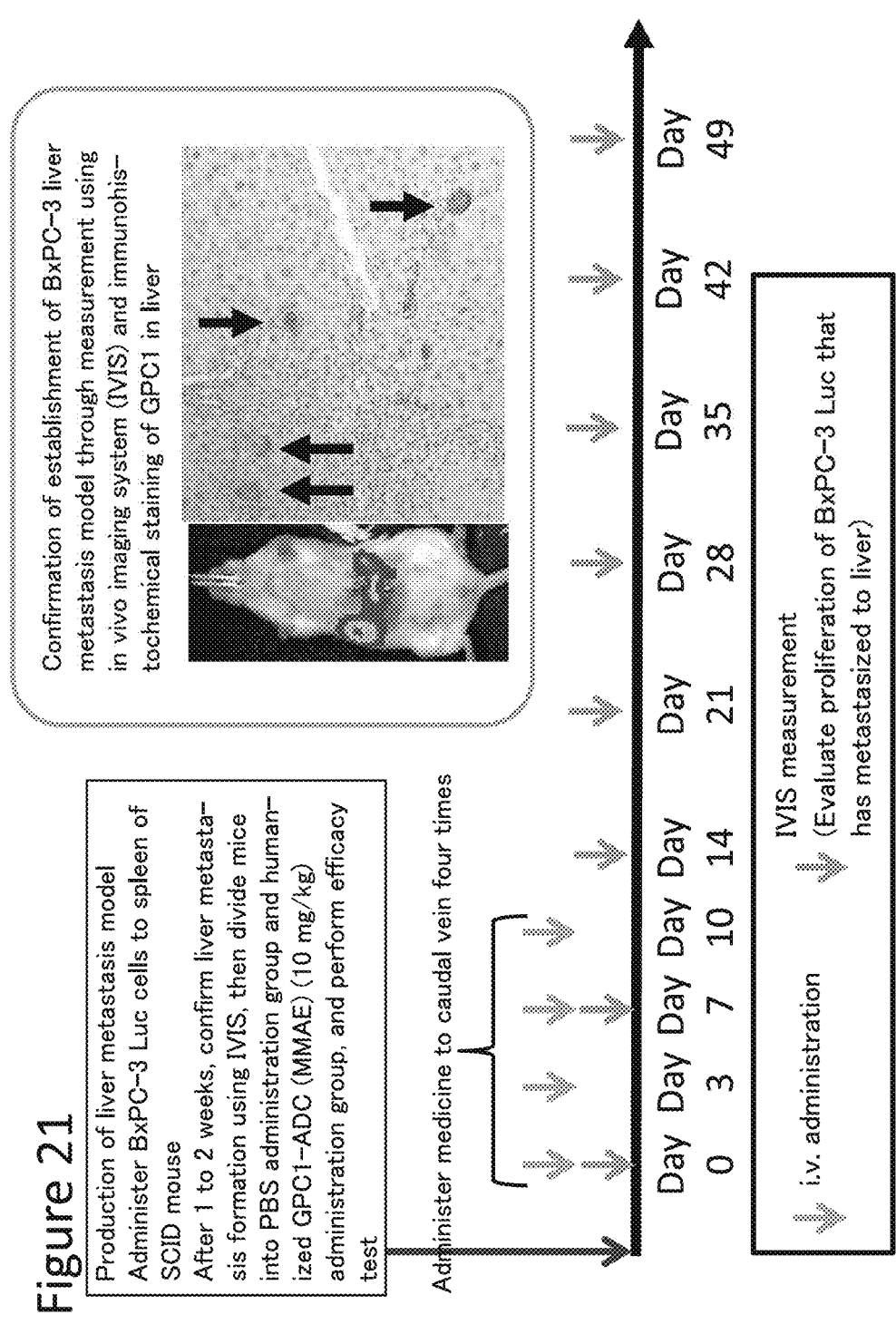

Production of liver metastasis model

Administer BxPC-3 Luc cells to spleen of SCID mouse

After 1 to 2 weeks, confirm liver metastasis formation using IVIS, then divide mice into PBS administration group and humanized GPC1-ADC (MMAE) (10 mg/kg) administration group, and perform efficacy test Administer medicine to caudal vein four times Confirmation of establishment of BxPC-3 liver metastasis model through measurement using in vivo imaging system (IVIS) and immunohistochemical staining of GPC1 in liver Day 0   Day 3   Day 7   Day 10   Day 14   Day 21   Day 28   Day 35   Day 42   Day 49 i.v. administration

IVIS measurement
(Evaluate proliferation of BxPC-3 Luc that has metastasized to liver)

HUMANIZED ANTI-GPC-1 ANTIBODY

SEQUENCE LISTING SUBMISSION VIA EFS-WEB

A computer readable text file, entitled "SequenceListing.txt" created on Dec. 5, 2022, with a file size of 54,979 bytes and contains the sequence listing for this application and is hereby incorporated by reference in its entirety.

TECHNICAL FIELD

The present disclosure relates to a humanized antibody that specifically binds to Glypican-1 (GPC-1), and also relates to technologies, methods, medicines, and the like related to the humanized antibody.

BACKGROUND ART

It was found that Glypican-1 molecules are significantly more highly expressed in esophageal cancer cells than normal cells and can be used as a tumor marker (Patent Literature 1). Also, an antibody that significantly binds to Glypican-1 was isolated (Patent Literature 1).

CITATION LIST

Patent Literature

Patent Literature 1: WO 2015/098112

SUMMARY OF INVENTION

Solution to Problem

In one aspect, the present disclosure provides a humanized anti-GPC-1 monoclonal antibody that has high affinity for GPC-1 and has high internalization activity in GPC-1-positive cells. A humanized anti-GPC-1 antibody had not been developed yet, and furthermore, a humanized anti-GPC-1 antibody was not predicted to have high activity. The antibody of the present disclosure can be used in various therapeutic applications.

Accordingly, in another aspect, the present disclosure also provides a composition for preventing or treating Glypican-1-positive cancer that includes a complex of a humanized anti-GPC-1 monoclonal antibody and a medicine having cytotoxic activity.

Such an antibody or a fragment thereof is applicable to a companion diagnostic reagent as well as a targeted treatment, personalized medical care, or the like that is combined with the companion diagnostic reagent.

Therefore, the present disclosure provides, for example, the following items.

(Item 1)

A humanized anti-GPC-1 antibody humanized based on an antibody that includes a heavy-chain variable region having an amino acid sequence set forth in SEQ ID NO: 5 and a light-chain variable region having an amino acid sequence set forth in SEQ ID NO: 6, or an antigen-binding fragment of the humanized anti-GPC-1 antibody, the humanized antibody or the antigen-binding fragment thereof having higher affinity for GPC-1 compared with the antibody that includes a heavy-chain variable region having an amino acid sequence set forth in SEQ ID NO: 5 and a light-chain variable region having an amino acid sequence set forth in SEQ ID NO: 6.

(Item 2)

The humanized antibody or the antigen-binding fragment thereof according to item 1, wherein the humanized antibody or the antigen-binding fragment thereof includes:

(a) heavy-chain CDRs 1 to 3 having amino acid sequences set forth in SEQ ID NOs: 28 to 30, respectively, or (b) has three or less amino acid substitution(s), deletion(s), and/or addition(s) in the heavy-chain CDRs 1 to 3 in (a).

(Item 3)

The humanized antibody or the antigen-binding fragment thereof according to item 1 or 2, including:

(a) light-chain CDRs 1 to 3 having amino acid sequences set forth in SEQ ID NOs: 31 to 33, respectively, or (b) light-chain CDRs 1 to 3 having amino acid sequences set forth in SEQ ID NOs: 34 to 36, respectively, or (c) including light-chain CDRs 1 to 3 having amino acid sequences set forth in SEQ ID NOs: 37 to 39, respectively, or (d) including light-chain CDRs 1 to 3 having amino acid sequences set forth in SEQ ID NOs: 40 to 42, respectively, or (e) including light-chain CDRs 1 to 3 having amino acid sequences set forth in SEQ ID NOs: 43 to 45, respectively, or (f) including light-chain CDRs 1 to 3 having amino acid sequences set forth in SEQ ID NOs: 46 to 48, respectively, or (g) including light-chain CDRs 1 to 3 having amino acid sequences set forth in SEQ ID NOs: 49 to 51, respectively, or (h) including light-chain CDRs 1 to 3 having amino acid sequences set forth in SEQ ID NOs: 52 to 54, respectively, or (i) including light-chain CDRs 1 to 3 having amino acid sequences set forth in SEQ ID NOs: 55 to 57, respectively, or (j) including light-chain CDRs 1 to 3 having amino acid sequences set forth in SEQ ID NOs: 58 to 60, respectively, or (k) including light-chain CDRs 1 to 3 having amino acid sequences set forth in SEQ ID NOs: 61 to 63, respectively, or (l) including light-chain CDRs 1 to 3 having amino acid sequences set forth in SEQ ID NOs: 64 to 66, respectively, or (m) including light-chain CDRs 1 to 3 having amino acid sequences set forth in SEQ ID NOs: 67 to 69, respectively, or (n) including light-chain CDRs 1 to 3 having amino acid sequences set forth in SEQ ID NOs: 70 to 72, respectively, or (o) including light-chain CDRs 1 to 3 having amino acid sequences set forth in SEQ ID NOs: 73 to 75, respectively, or (p) including light-chain CDRs 1 to 3 having amino acid sequences set forth in SEQ ID NOs: 76 to 78, respectively, or (q) including light-chain CDRs 1 to 3 having amino acid sequences set forth in SEQ ID NOs: 79 to 81, respectively, or (r) including light-chain CDRs 1 to 3 having amino acid sequences set forth in SEQ ID NOs: 82 to 84, respectively, or (s) including light-chain CDRs 1 to 3 having amino acid sequences set forth in SEQ ID NOs: 85 to 87, respectively, or (t) including light-chain CDRs 1 to 3 having amino acid sequences set forth in SEQ ID NOs: 88 to 90, respectively, or (u) having three or less amino acid substitutions, deletions, and/or additions in the light-chain CDRs 1 to 3 in any of (a) to (t).

(Item 4)

The humanized antibody or the antigen-binding fragment thereof according to any one of items 1 to 3, including a heavy-chain variable region having an amino acid sequence with at least 90% identity to an amino acid sequence set forth in SEQ ID NO: 7.

(Item 5)

The humanized antibody or the antigen-binding fragment thereof according to any one of items 1 to 4, including a light-chain variable region having an amino acid sequence with at least 90% identity to an amino acid sequence selected from the group consisting of amino acid sequences set forth in SEQ ID NOs: 8 to 27.

(Item 6)

The humanized antibody or the antigen-binding fragment thereof according to any one of items 1 to 5, including a light-chain variable region having an amino acid sequence selected from the group consisting of amino acid sequences set forth in SEQ ID NOs: 8 to 27.

(Item 7)

The humanized antibody or the antigen-binding fragment thereof according to any one of items 1 to 6, including a light-chain variable region having an amino acid sequence with at least 90% identity to an amino acid sequence selected from the group consisting of amino acid sequences set forth in SEQ ID NOs: 8 to 17.

(Item 8)

The humanized antibody or the antigen-binding fragment thereof according to any one of items 1 to 7, including a light-chain variable region having an amino acid sequence selected from the group consisting of amino acid sequences set forth in SEQ ID NOs: 8 to 17.

(Item 9)

The humanized antibody or the antigen-binding fragment thereof according to any one of items 1 to 8, wherein an epitope of the antibody includes positions 339 to 358 and/or 388 to 421 of SEQ ID NO: 2.

(Item 10)

The humanized antibody or the antigen-binding fragment thereof according to any one of items 1 to 9, wherein the antibody binds to Glypican-1 with a $K_D$ of $1.02E^{-8}$ or less, the $K_D$ being based on analysis using a surface plasmon resonance technique.

(Item 11)

A pharmaceutical composition for transferring an active ingredient into a cell, including the humanized antibody or the antigen-binding fragment thereof according to any one of items 1 to 10.

(Item 12)

A complex of the humanized antibody or the antigen-binding fragment thereof according to any one of items 1 to 10, and a medicine having cytotoxic activity.

(Item 13)

The complex according to item 12, wherein the humanized antibody or the antigen-binding fragment thereof is operably linked to the medicine having cytotoxic activity via a linker.

(Item 14)

The complex according to item 12 or 13, wherein the medicine having cytotoxic activity is selected from the group consisting of monomethyl auristatin E (MMAE), monomethyl auristatin F (MMAF), DM1, DM4, calicheamicin, duocarmycin, pyrrolobenzodiazepine (PBD), and topoisomerase inhibitors.

(Item 15)

The complex according to item 13 or 14, wherein the medicine having cytotoxic activity has cell membrane permeability.

(Item 16)

The complex according to any one of items 13 to 15, wherein the medicine having cytotoxic activity is selected from MMAE, PBD, Eribulin, SN-38, Dxd, and DM4.

(Item 17)

The complex according to any one of items 13 to 16, wherein the linker is selected from the group consisting of an enzyme cleavable linker, an acid labile linker, and a disulfide linker.

(Item 18)

The complex according to any one of items 13 to 17, wherein the linker is a cleavable linker capable of being cleaved by cathepsin B.

(Item 19)

The complex according to any one of items 12 to 18, wherein the complex has an $IC_{50}$ of about 0.1 nM or less in a Glypican-1-positive cell.

(Item 20)

A composition for preventing or treating Glypican-1-positive cancer, including the complex according to any one of items 12 to 19.

(Item 21)

The composition according to item 20, wherein the Glypican-1-positive cancer is selected from esophageal cancer, pancreatic cancer, bile duct cancer, cervical cancer, lung cancer, head and neck cancer, breast cancer, uterine leiomyosarcoma, prostate cancer, oral squamous cell cancer, and any combinations thereof.

(Item 22)

The composition according to item 20 or 21, wherein the Glypican-1-positive cancer is esophageal cancer or pancreatic cancer.

(Item 23)

The composition according to any one of items 20 to 22, wherein the cancer has cancer-associated fibroblasts (CAFs).

(Item 24)

The composition according to any one of items 20 to 23, wherein the composition is administered together with an immune checkpoint inhibitor.

(Item 25)

The composition according to item 24, wherein the immune checkpoint inhibitor is an anti-PD-1 antibody.

(Item 26)

A composition for preventing or treating metastatic cancer of Glypican-1-positive cancer, including the complex according to any one of items 12 to 19.

(Item 27)

The composition according to item 26, wherein the Glypican-1-positive cancer is selected from esophageal cancer, pancreatic cancer, bile duct cancer, cervical cancer, lung cancer, head and neck cancer, breast cancer, uterine leiomyosarcoma, prostate cancer, oral squamous cell cancer, and any combinations thereof.

(Item 28)

The composition according to item 26 or 27, wherein the metastatic cancer is metastatic cancer of pancreatic cancer.

(Item 29)

The composition according to any one of items 26 to 28, wherein the metastatic cancer is metastatic cancer that has metastasized to a liver, esophagus, bile duct, cervix, lung, head and neck region, breast, uterine smooth muscle, prostate, oral squamous epithelium, brain, bone, peritoneum, or adrenal.

(Item 1A)

A method for transferring an active ingredient into a cell, including a step of administering the humanized antibody or the antigen-binding fragment thereof according to any one of items 1 to 10 to the cell.

(Item 2A)

A method for preventing or treating Glypican-1-positive cancer in a subject, including a step of administering the complex according to any one of items 12 to 19 to the subject.

(Item 3A)

The method according to item 2A, wherein the Glypican-1-positive cancer is selected from esophageal cancer, pancreatic cancer, bile duct cancer, cervical cancer, lung cancer, head and neck cancer, breast cancer, uterine leiomyosarcoma, prostate cancer, oral squamous cell cancer, and any combinations thereof.

(Item 4A)

The method according to item 2A or 3A, wherein the Glypican-1-positive cancer is esophageal cancer or pancreatic cancer.

(Item 5A)

The method according to any one of items 2A to 4A, wherein the cancer has cancer-associated fibroblasts (CAFs).

(Item 6A)

The method according to any one of items 2A to 5A, further including a step of administering an immune checkpoint inhibitor.

(Item 7A)

The method according to item 6A, wherein the immune checkpoint inhibitor is an anti-PD-1 antibody.

(Item 8A)

A method for preventing or treating metastatic cancer of Glypican-1-positive cancer in a subject, including a step of administering the complex according to any one of items 12 to 19 to the subject.

(Item 9A)

The method according to item 8A, wherein the Glypican-1-positive cancer is selected from esophageal cancer, pancreatic cancer, bile duct cancer, cervical cancer, lung cancer, head and neck cancer, breast cancer, uterine leiomyosarcoma, prostate cancer, oral squamous cell cancer, and any combinations thereof.

(Item 10A)

The method according to item 8A or 9A, wherein the metastatic cancer is metastatic cancer of pancreatic cancer.

(Item 11A)

The method according to any one of items 8A to 10A, wherein the metastatic cancer is metastatic cancer that has metastasized to a liver, esophagus, bile duct, cervix, lung, head and neck region, breast, uterine smooth muscle, prostate, oral squamous epithelium, brain, bone, peritoneum, or adrenal.

(Item 1B)

Use of the humanized antibody or the antigen-binding fragment thereof according to any one of items 1 to 10 in the manufacture of a pharmaceutical drug for transferring an active ingredient into a cell.

(Item 2B)

Use of the complex according to any one of items 12 to 19 in the manufacture of a pharmaceutical drug for preventing or treating Glypican-1-positive cancer in a subject.

(Item 3B)

The use according to item 2B, wherein the Glypican-1-positive cancer is selected from esophageal cancer, pancreatic cancer, bile duct cancer, cervical cancer, lung cancer, head and neck cancer, breast cancer, uterine leiomyosarcoma, prostate cancer, oral squamous cell cancer, and any combinations thereof.

(Item 4B)

The use according to item 2B or 3B, wherein the Glypican-1-positive cancer is esophageal cancer or pancreatic cancer.

(Item 5B)

The use according to any one of items 2B to 4B, wherein the cancer has cancer-associated fibroblasts (CAFs).

(Item 6B)

The use according to any one of items 2B to 5B, characterized in that the complex is administered together with an immune checkpoint inhibitor.

(Item 7B)

The use according to item 6B, wherein the immune checkpoint inhibitor is an anti-PD-1 antibody.

(Item 8B)

Use of the complex according to any one of items 12 to 19 in the manufacture of a pharmaceutical drug for preventing or treating metastatic cancer of Glypican-1-positive cancer in a subject.

(Item 9B)

The use according to item 8B, wherein the Glypican-1-positive cancer is selected from esophageal cancer, pancreatic cancer, bile duct cancer, cervical cancer, lung cancer, head and neck cancer, breast cancer, uterine leiomyosarcoma, prostate cancer, oral squamous cell cancer, and any combinations thereof.

(Item 10B)

The use according to item 8B or 9B, wherein the metastatic cancer is metastatic cancer of pancreatic cancer.

(Item 11B)

The use according to any one of items 8B to 10B, wherein the metastatic cancer is metastatic cancer of a liver, esophagus, bile duct, cervix, lung, head and neck region, breast, uterine smooth muscle, prostate, oral squamous epithelium, brain, bone, peritoneum, or adrenal.

(Item 1C)

The humanized antibody or the antigen-binding fragment thereof according to any one of items 1 to 10 for transferring an active ingredient into a cell.

(Item 2C)

The complex according to any one of items 12 to 19 for preventing or treating Glypican-1-positive cancer in a subject.

(Item 3C)

The complex according to item 2C, wherein the Glypican-1-positive cancer is selected from esophageal cancer, pancreatic cancer, bile duct cancer, cervical cancer, lung cancer, head and neck cancer, breast cancer, uterine leiomyosarcoma, prostate cancer, oral squamous cell cancer, and any combinations thereof.

(Item 4C)

The complex according to item 2C or 3C, wherein the Glypican-1-positive cancer is esophageal cancer or pancreatic cancer.

(Item 5C)

The complex according to any one of items 2C to 4C, wherein the cancer has cancer-associated fibroblasts (CAFs).

(Item 6C)

The complex according to any one of items 2C to 5C, wherein the complex is administered together with an immune checkpoint inhibitor.

(Item 7C)

The complex according to item 6C, wherein the immune checkpoint inhibitor is an anti-PD-1 antibody.

(Item 8C)

The complex according to any one of items 12 to 19 for preventing or treating metastatic cancer of Glypican-1-positive cancer in a subject.

(Item 9C)

The complex according to item 8C, wherein the Glypican-1-positive cancer is selected from esophageal cancer, pancreatic cancer, bile duct cancer, cervical cancer, lung cancer, head and neck cancer, breast cancer, uterine leiomyosarcoma, prostate cancer, oral squamous cell cancer, and any combinations thereof.

(Item 10C)

The complex according to item 8C or 9C, wherein the metastatic cancer is metastatic cancer of pancreatic cancer.

(Item 11C)

The complex according to any one of items 8C to 10C, wherein the metastatic cancer is metastatic cancer that has metastasized to a liver, esophagus, bile duct, cervix, lung, head and neck region, breast, uterine smooth muscle, prostate, oral squamous epithelium, brain, bone, peritoneum, or adrenal.

In the present disclosure, it is intended that other combinations of the above-mentioned one or more features than the specified combinations thereof may be provided. If a person skilled in the art reads and understands the following detailed description as needed, he/she will recognize further embodiments and advantages of the present disclosure.

Advantageous Effects of Invention

According to the present disclosure, a humanized anti-Glypican-1 antibody applicable to clinical use is provided. Such an antibody can be utilized as a detection agent used for diagnosis and companion treatment of Glypican-1-positive cancer, and furthermore, a complex of the antibody and a drug is highly effective in treatment of Glypican-1-positive cancer.

BRIEF DESCRIPTION OF DRAWINGS

FIG. 1 shows equilibrium dissociation constants ($K_D$) of twenty types of clones measured using Biacore (registered trademark).

FIG. 13 shows the results of an in-vivo efficacy test of a humanized GPC1-ADC (MMAE) using a pancreatic cancer PDX (PK565) in which the GPC1 expression is heterogeneous. In all the groups, the body weights did not significantly change. The tumor volume was almost unchanged in the case of Humanized GPC1-ADC (10 mg/kg), the tumor volume slightly increased in the case of Humanized GPC1-ADC (3 mg/kg), the tumor volumes increased and were substantially the same in the cases of Humanized GPC-ADC (1 mg/kg) and Control-ADC (10 mg/kg), and the tumor volume increased and was the largest in the case of Vehicle control.

FIG. 14 shows the results of an in-vivo efficacy test of a humanized GPC1-ADC (MMAE) using a pancreatic cancer PDX (PK175) in which GPC1 is expressed in both cancer cells and CAFs. The body weights slightly increased in the cases of Humanized GPC1-ADC (10 mg/kg) and Humanized GPC1-ADC (3 mg/kg). The body weights did not significantly change in the cases of Humanized GPC-ADC (1 mg/kg) and Vehicle control. The tumor volume decreased and was the smallest in the case of Humanized GPC1-ADC (10 mg/kg), the tumor volume slightly increased in the case of Humanized GPC1-ADC (3 mg/kg), the tumor volumes gradually increased in the cases of Humanized GPC-ADC (1 mg/kg) and Vehicle control, and the tumor volume was the largest in the case of Vehicle control.

FIG. 16 shows the results of a GPC1 expression analysis and an ADC assay of a mouse colorectal cancer cell line forced to express mGPC1 (mGPC1-MC38).

FIG. 21 shows the outlines of production of a pancreatic cancer liver metastasis model and an efficacy test using a humanized GPC1-ADC. On day 0, day 3, day 7, and day 10, i.v. administration was performed. On day 0, day 7, day 14, day 21, day 28, day 35, day 42, and day 49, IVIS measurement was performed.

DESCRIPTION OF EMBODIMENTS

Figure 2:
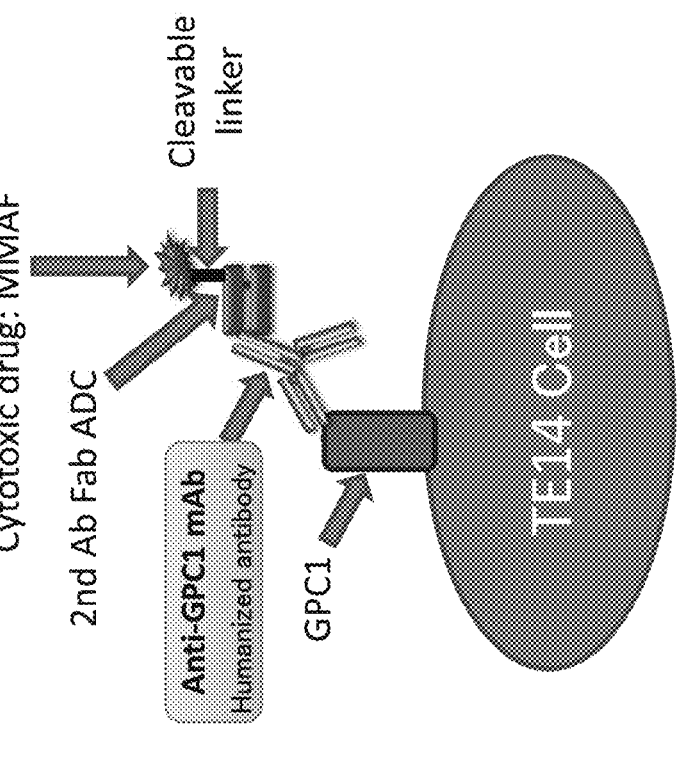
FIG. 2 shows a schematic diagram illustrating an ADC assay of Example 2.

Hereinafter, the present disclosure will be described. It should be understood that, throughout this specification, nouns expressed in a singular form also encompass concepts of the nouns in a plural form unless otherwise stated. Accordingly, it should be understood that articles (e.g., "a", "an", and "the" in English) used with nouns in a singular form also encompass concepts of the nouns in a plural form unless otherwise stated. Also, it should be understood that the terms as used herein are used in the general senses in the art unless otherwise stated. Accordingly, all of the technical terms and the scientific terms as used herein are used in the same senses as those understood by a person skilled in the art to which the present disclosure belongs, unless otherwise defined. If a contradiction arises, this specification (including the definitions) has priority. The term "about" means±10% of an indicated value.

Definitions

First, the terms and the common technologies as used herein will be described.

In this specification, the terms "Glypican-1", "GPC-1", and "GPC-1" are used interchangeably, and refer to a glycosylphosphatidylinositol (GPI) anchor-type cell-surface proteoglycan having heparan sulfate. This proteoglycan is regarded as being related to cell adhesion, migration, lipoprotein metabolism, growth factor activity regulation, and blood coagulation inhibition. The proteoglycan is said to bind to several types of fibroblast growth factors (FGFs) such as FGF-1, FGF-2, and FGF-7. Glypican-1 is regarded as serving as an extracellular chaperone of VEGF165 and aiding in restoring the receptor binding ability after oxidation. At present, six types of Glypicans, namely Glypican-1 to Glypican-6, are known. However, regarding the relationship with cancer, all the members belonging to the Glypican family are not necessarily recognized as a cancer marker, and the members seem to be independent of one another. Glypican-1 is registered in UniProt (Accession No. P35052) (see uniprot.org/uniprot/P35052). In addition, Glypican-1 is registered in NCBI (NP_002072.2 (amino acid sequence of the precursor) and NM_002081.2 (mRNA)), EMBL (X54232.1 (mRNA)), GenBank (BC051279.1 (mRNA)), and DDBJ (AC110619.3 (genomic)). All these pieces of information can be utilized in this specification, and are incorporated herein by reference. Regarding Glypican-1, David Get al., J Cell Biol. 1990 December; 111 (6 Pt 2): 3165-76; Haecker U et al., Nat Rev Mol Cell Biol. 2005 July; 6 (7): 530-41; Aikawa T et al., J Clin Invest. 2008 January; 118 (1): 89-99.; Matsuda K, et al., Cancer Res. 2001 Jul. 15; 61 (14): 5562-9., and the like can be referred to. A representative example of the nucleic acid sequence (full length) of human Glypican-1 is a sequence set forth in SEQ ID NO: 1, and a representative example of the amino acid sequence thereof is a sequence set forth in SEQ ID NO: 2. Also, a representative example of the nucleic acid sequence (full length) of mouse Glypican-1 is a sequence set forth in SEQ ID NO: 3, and a representative example of the amino acid sequence thereof is a sequence set forth in SEQ ID NO: 4. In the case where "Glypican-1", "GPC-1", or "GPC-1" is used with the object of this specification, it is understood that not only a protein (or a nucleic acid coding for the protein) having an amino acid sequence of a specific sequence ID number or accession number but also functionally active analogues or derivatives thereof, functionally active fragments thereof, homologues thereof, and variants coded for by nucleic acids that hybridize with the nucleic acid coding for this protein under high stringency conditions or low stringency conditions can also be used in the present disclosure as long as they suit the specific object of the present disclosure.

The terms "derivative", "analogue", and "variant" as used herein preferably encompass molecules that include a region substantially homologous with a protein of interest (e.g., Glypican-1 and an antibody), but are not intended to be limited thereto. In various embodiments, such molecules have at least 30%, 40%, 50%, 60%, 70%, 80%, 90%, 95%, 96%, 97%, 98%, or 99% identity when compared with an amino acid sequence having the same size or a sequence aligned by performing alignment with a computer homology program known in the art. Alternatively, nucleic acids coding for such molecules can hybridize with the sequence coding for the constituent protein under (highly) stringent conditions, moderately stringent conditions, or non-stringent conditions. This means that these molecules are produced by modifying a protein through substitution, deletion, and addition of an amino acid, and the thus produced derivatives still exhibit biological functions of the original protein, though they need not necessarily exhibit the functions to the same extent as the original protein. For example, it is also possible to examine the biological functions of such proteins through appropriate available in-vitro assays that are described herein or known in the art. The expression "functionally active" as used herein refers to polypeptides, namely fragments or derivatives, having structural functions, control functions, or biochemical functions of a protein, such as biological activity, according to aspects involving polypeptides, namely fragments or derivatives, of the present disclosure in this specification.

Although the present disclosure mainly describes human Glypican-1, it is known that Glypican-1 proteins are expressed in lots of animal species other than human, such as chimpanzees (Pan troglodytes) (K7B6W5), rhesus monkeys (Macaca mulatta) (F6VPW9), mice (Mus musculus) (Q9QZF2), rats (Rattus norvegicus) (P35053), and chickens (Gallus gallus) (F1P150), and thus it is understood that these animals, particularly mammals, fall within the scope of the present disclosure. It is preferable that preferably functional domains of Glypican-1, such as the extracellular domain (constituted by about 500 amino acids including 12 cysteine residues) and the C-terminal hydrophobic region (GPI-anchor domain), are conserved.

The terms "protein", "polypeptide", "oligopeptide", and "peptide" as used herein are used interchangeably in this specification, and refer to an amino acid polymer having any length. This polymer may be a linear polymer, a branched polymer, or a cyclic polymer. The amino acid may be a natural amino acid or a non-natural amino acid, and may be a modified amino acid. These terms may encompass a complex obtained by assembling a plurality of polypeptide chains. These terms also encompass a naturally or artificially modified amino acid polymer. Such modifications encompass, for example, disulfide bond formation, glycosylation, lipidation, acetylation, phosphorylation, and any other operations or modifications (e.g., formation of a polymer bound to a label component). This definition encompasses, for example, polypeptides that include one or two or more amino acid analogues (e.g., polypeptides that include a non-natural amino acid or the like), peptide-like compounds (e.g., peptoids), and other modifications known in the art. The term "amino acid" as used herein is a generic name for organic compounds having an amino group and a carboxyl group. When an antibody according to an embodiment of the present disclosure includes a "specific amino acid sequence", any of the amino acids in the amino acid sequence may be chemically modified. Also, any of the amino acids in the amino acid sequence may form a salt or solvate. Also, any of the amino acids in the amino acid sequence may be an L-amino acid or a D-amino acid. Even in such cases, it can be said that a protein according to an embodiment of the present disclosure includes the above-mentioned "specific amino acid sequence". For example, N-terminal modifications (e.g., acetylation and myristoylation), C-terminal modifications (e.g., amidation and addition of glycosylphosphatidylinositol), side-chain modifications (e.g., phosphorylation and glycosylation) are known as chemical modifications that an amino acid included in a protein undergo in a living organism. The amino acid may be a natural amino acid or a non-natural amino acid as long as the object of the present disclosure is met.

The terms "polynucleotide", "oligonucleotide", and "nucleic acid" as used herein are used interchangeably in this specification, and refer to a nucleotide polymer having any length. These terms also encompass "oligonucleotide derivatives" and "polynucleotide derivatives". The "oligonucleotide derivatives" and the "polynucleotide derivatives" refer to oligonucleotides or polynucleotides that include a nucleotide derivative or in which a bond between nucleotides is different from a common bond, and are used interchangeably. Specific examples of such oligonucleotides include 2'-O-methyl-ribonucleotide, an oligonucleotide derivative obtained by converting a phosphodiester bond in an oligonucleotide to a phosphorothioate bond, an oligonucleotide derivative obtained by converting a phosphodiester bond in an oligonucleotide to an N3'-P5' phosphoramidate bond, an oligonucleotide derivative obtained by converting a ribose and a phosphodiester bond in an oligonucleotide to a peptide nucleic acid bond, an oligonucleotide derivative obtained by substituting an uracil in an oligonucleotide with a C-5 propynyluracil, an oligonucleotide derivative obtained by substituting an uracil in an oligonucleotide with a C-5 thiazoleuracil, an oligonucleotide derivative obtained by substituting a cytosine in an oligonucleotide with a C-5 propynylcytosine, an oligonucleotide derivative obtained by substituting a cytosine in an oligonucleotide with a phenoxazine-modified cytosine, an oligonucleotide derivative obtained by substituting a ribose in DNA with 2'-O-propylribose, and an oligonucleotide derivative obtained by substituting a ribose in an oligonucleotide with 2'-methoxyethoxyribose. Unless otherwise stated, it is intended that a specific nucleic acid sequence also encompass explicitly shown sequences as well as modified sequences (e.g., degenerate codon substitution sequences) thereof obtained by conservatively modifying the sequences and complementary sequences thereof. Specifically, the degenerate codon substitution sequences can be obtained by producing a sequence in which the third positions in one or more selected (or all) codons are substituted with mixed bases and/or deoxyinosine residues (Batzer et al., Nucleic Acid Res. 19: 5081 (1991); Ohtsuka et al., J. Biol. Chem. 260: 2605-2608 (1985); Rossolini et al., Mol. Cell. Probes 8: 91-98 (1994)). Also, in this specification, the "nucleic acid" is used interchangeably with a gene, a cDNA, an mRNA, an oligonucleotide, and a polynucleotide. In this specification, the "nucleotide" may be a natural nucleotide or a non-natural nucleotide.

The term "gene" as used herein refers to a factor that determines an inherited trait, and the "gene" may refer to a "polynucleotide", an "oligonucleotide", and a "nucleic acid".

The term genetic "homology" as used herein refers to the degree of identity between two or more gene sequences, and "homologous" commonly means that the degree of identity or similarity is high. Accordingly, the higher the homology between certain two genes is, the higher the identity or similarity between their sequences is. Whether or not two types of genes are homologous to each other can be examined by directly comparing their sequences, or subjecting nucleic acids to a hybridization method under stringent conditions. In the case where two gene sequences are directly compared, the genes are homologous when the DNA sequence identity between the gene sequences is typically at least 50%, preferably at least 70%, and more preferably at least 80%, 90%, 95%, 96%, 97%, 98%, or 99%. Accordingly, the term "homologue" or "homologous gene product" as used herein means a protein of another species, preferably another mammal, that exhibits the same biological functions as those of a constituent protein of a complex, which will also be described in this specification. Such a homologue may also be referred to as an "orthologue gene product". It is understood that such homologues, homologous gene products, orthologous gene products, and the like can also be used as long as the object of the present disclosure is met.

In this specification, amino acids may be referred to using the commonly known three-letter codes or the one-letter codes recommended by IUPAC-IUB Biochemical Nomenclature Commission. Similarly, nucleotides may be referred to using the commonly recognized one-letter codes. In this specification, comparisons of similarity, identity, and homology between amino acid sequences and those between base sequences are calculated using BLAST, which is a sequence analysis tool, with default parameters. Identity search can be performed using NCBI BLAST 2.2.28 (released on Apr. 2, 2013). The identity values in this specification are generally values obtained by using BLAST above to perform alignment under default conditions. However, in the case where a higher value is obtained by changing the parameters, the highest value is taken as the identity value. In the case where the identity is evaluated at a plurality of regions, the highest value among the obtained values is taken as the identity value. The similarity is a numerical value calculated with the identity as well as similar amino acids being taken into consideration.

In one embodiment of the present disclosure, "90% or more" may be, for example, 90% or more, 95% or more, 96% or more, 97% or more, 98% or more, 99% or more, or 100% or more, or may be within a range between any two values above. The above-mentioned "homology" may be determined by calculating the ratio of the number of homologous amino acids between two or more amino acid sequences in accordance with a method known in the art. Before the ratio is calculated, amino acid sequences to be compared in the amino acid sequence group are aligned, and a gap is introduced into a portion of an amino acid sequence if this is needed to maximize the ratio of identical amino acids. The alignment method, the ratio calculation method, the comparison method, and computer programs related thereto are conventionally well known in the art (for example, BLAST, GENETYX, and the like). In this specification, the "homology" can be represented by a value measured using NCBI BLAST unless otherwise stated. In BLAST, Blastp can be used with default settings as an algorithm for comparing amino acid sequences. The measurement results are converted to numerical values as Positives or Identities.

The term "functional equivalent" as used herein refers to any substance that has the same function of interest as the original target entity but has a different structure. Accordingly, it is understood that the functional equivalent of "Glypican-1" or a Glypican-1 antibody encompasses a substance that is not Glypican-1 or a Glypican-1 antibody but a variant or altered product (with a modified amino acid sequence or the like, for example) of Glypican-1 or a Glypican-1 antibody that retains biological effects of Glypican-1 or a Glypican-1 antibody, and a substance that can change into Glypican-1 or a Glypican-1 antibody, or a variant or altered product of Glypican-1 or a Glypican-1 antibody (including a nucleic acid coding for Glypican-1 or a Glypican-1 antibody, or a variant or altered product of Glypican-1 or a Glypican-1 antibody, a vector and cells that include the nucleic acid above, and the like) when such effects should be exhibited. It is understood that, in the present disclosure, the functional equivalent of Glypican-1 or a Glypican-1 antibody can be used in the same manner as Glypican-1 or a Glypican-1 antibody without making special references. The functional equivalent can be found by searching a database and the like. The term "search" as used herein means that a certain nucleic acid sequence is used in an electronic or biological method or in other methods to find another nucleic acid sequence having a certain function and/or characteristic. Examples of electronic search include, but are not limited to, BLAST (Altschul et al., J. Mol. Biol. 215: 403-410 (1990)), FASTA (Pearson & Lipman, Proc. Natl. Acad. Sci., USA 85: 2444-2448 (1988)), the Smith and Waterman method (Smith and Waterman, J. Mol. Biol. 147: 195-197 (1981)), and the Needleman and Wunsch method (Needleman and Wunsch, J. Mol. Biol. 48: 443-453 (1970)). Examples of biological search include, but are not limited to, stringent hybridization, microarray assay using a microarray obtained by attaching genome DNA to a nylon membrane or the like or a microarray obtained by attaching genome DNA on a glass plate, PCR, and in-situ hybridization. In this specification, it is intended that genes used in the present disclosure should include corresponding genes identified through such electronic search or biological search.

The functional equivalent of the present disclosure may be obtained by performing insertion, substitution, or deletion of one or more amino acids on an amino acid sequence or addition of one or more amino acids to one or both termini of an amino acid sequence. In this specification, the wording "performing insertion, substitution, or deletion of one or more amino acids on an amino acid sequence or addition of one or more amino acids to one or both termini of an amino acid sequence" means that an amino acid sequence is modified through a well-known technique such as site-directed mutagenesis or natural mutation, so that a plurality of amino acids are substituted, for example, to such an extent that may naturally occur. The modified amino acid sequence can be obtained by performing insertion, substitution, or deletion, or addition to one or both termini, of, for example, 1 to 30 amino acids, preferably 1 to 20 amino acids, more preferably 1 to 9 amino acids, even more preferably 1 to 5 amino acids, and particularly preferably 1 or 2 amino acids. The modified amino acid sequence may be the amino acid sequence of Glypican-1 that preferably includes one or more (preferably one or several, or one, two, three, or four) conservative substitutions. Here, the "conservative substitution" means that one or more amino acid residues are substituted with other chemically similar amino acid residues such that protein functions are not substantially modified. Examples thereof include substitution of a certain hydrophobic residue with another hydrophobic residue, and substitution of a certain polar residue with another polar residue having the same electric charge. For each amino acid, a functionally similar amino acid that can be used to perform such substitution is known in the art. Specific examples of the non-polar (hydrophobic) amino acids include alanine, valine, isoleucine, leucine, proline, tryptophan, phenylalanine, and methionine. Specific examples of the polar (neutral) amino acids include glycine, serine, threonine, tyrosine, glutamine, asparagine, and cysteine. Specific examples of the amino acids having a positive electric charge (basic amino acids) include arginine, histidine, and lysine. Specific examples of the amino acids having a negative electric charge (acidic amino acids) include aspartic acid and glutamic acid.

In one embodiment of the present disclosure, an "anti-Glypican-1 antibody" includes an antibody having a Glypican-1-binding ability. Although there is no particular limitation on a method for producing this anti-Glypican-1 antibody, this antibody may be produced, for example, by immunizing a mammal or bird with Glypican-1. The "antigen-binding fragment" of the anti-Glypican-1 antibody refers to a fragment of an antibody having a Glypican-1-binding ability. Examples of this antigen-binding fragment include, but are not limited to, a single-chain antibody, an scFv, a Fab fragment, and a F(ab')2 fragment.

Although there is no particular limitation on the antibody class of the anti-Glypican-1 antibody according to one embodiment of the present disclosure, it may be, for example, IgM, IgD, IgG, IgA, IgE, or IgY.

The anti-Glypican-1 antibody according to one embodiment of the present disclosure may be an antibody fragment (which may also be referred to as an "antigen-binding fragment" hereinafter) having an antigen-binding activity. In this case, a stability increasing effect, an antibody production efficiency increasing effect, and the like are obtained.

The anti-Glypican-1 antibody according to one embodiment of the present disclosure may be a fusion protein. This fusion protein may be obtained by linking a polypeptide or an oligopeptide to the N- or C-terminus of the anti-Glypican-1 antibody. Here, the oligopeptide may be a His tag.

The anti-Glypican-1 antibody according to one embodiment of the present disclosure may be, for example, an antibody obtained through a step of immunizing a living organism with purified Glypican-1, Glypican-1-expressing cells, or a Glypican-1-containing lipid membrane. It is preferable to use Glypican-1-expressing cells for immunization from the viewpoint of enhancing an effect of treating Glypican-1-positive cancer.

The anti-Glypican-1 antibody according to one embodiment of the present disclosure may be an antibody having a CDR set of an antibody obtained through a step of immunizing a living organism with purified Glypican-1, Glypican-1-expressing cells, or a Glypican-1-containing lipid membrane. It is preferable to use Glypican-1-expressing cells for immunization from the viewpoint of enhancing an effect of treating Glypican-1-positive cancer. The CDR set includes heavy-chain CDRs 1, 2, and 3 and light-chain CDRs 1, 2, and 3.

In one embodiment of the present disclosure, the "Glypican-1 expressing cells" may be obtained by, for example, introducing a polynucleotide coding for Glypican-1 into cells and then allowing the cells to express Glypican-1. Here, Glypican-1 includes a Glypican-1 fragment. Also, in one embodiment of the present disclosure, the "Glypican-1-containing lipid membrane" may be obtained by, for example, mixing Glypican-1 and a lipid bilayer membrane. Here, Glypican-1 includes a Glypican-1 fragment. Also, the anti-Glypican-1 antibody according to one embodiment of the present disclosure is preferably an antibody obtained through a step of immunizing a chicken with an antigen, or an antibody having the CDR set of the thus obtained antibody, from the viewpoint of enhancing an effect of treating Glypican-1-positive cancer.

The anti-Glypican-1 antibody of the present disclosure may have any binding force as long as the object is achieved. For example, even if the anti-Glypican-1 antibody of the present disclosure has low affinity for Glypican-1, it is sufficient that it has internalization activity and/or ADC activity. However, it is preferable that this antibody has strong binding force in the case where it is used for the application to diagnosis or a companion agent. For example, the KD value (kd/ka) may be $1.0 \times 10^{-7}$ (M) or less, $1.0 \times 10^{-8}$ (M) or less, $1.0 \times 10^{-9}$ (M) or less, or $1.0 \times 10^{-10}$ (M) or less. When the anti-Glypican-1 antibody is used for the application to diagnosis or a companion agent, the binding force thereof expressed as the KD value (kd/ka) is preferably $1.0 \times 10^{-8}$ (M) or less.

The anti-Glypican-1 antibody according to one embodiment of the present disclosure may bind to wild-type Glypican-1 or mutant Glypican-1. The term "mutant" encompasses mutations caused by a difference in the DNA sequence between individual antibodies. The homology of the amino acid sequence of wild-type Glypican-1 or mutant Glypican-1 to the amino acid sequence set forth in SEQ ID NO: 2 is preferably 80% or more, more preferably 90% or more, even more preferably 95% or more, and particularly preferably 98% or more.

In this specification, the "antibody" encompasses molecules or populations thereof that can specifically bind to a specific epitope on an antigen. The antibody can be present in various forms, and one or more forms may be selected from the group consisting of, for example, a full-length antibody (antibody having a Fab region and a Fc region), an Fv antibody, a Fab antibody, an F(ab')2 antibody, a Fab' antibody, a diabody, a single-stranded (single-chain) antibody (e.g., scFv), an sc(Fv)2 (single-chain (Fv)2), an scFv-Fc, a dsFv, a multispecific antibody (e.g., oligospecific antibody or bispecific antibody), a diabody, a peptide or polypeptide having an antigen-binding ability, a chimeric antibody (e.g., mouse-human chimeric antibody or chicken-human chimeric antibody), a mouse antibody, a chicken antibody, a humanized antibody, a human antibody, and substances equal thereto (or equivalents). Also, the antibody encompasses modified antibodies and unmodified antibodies. The modified antibodies may be formed by linking various molecules such as polyethylene glycol to antibodies. The modified antibodies can be obtained by chemically modifying an antibody using a known method. Furthermore, such antibodies may be fused to an enzyme such as alkaline phosphatase, horseradish peroxidase, or u-galactosidase via a covalent bond or through recombination. It is sufficient that the anti-Glypican-1 antibody used in the present disclosure binds to a Glypican-1 protein, and there is no limitation on the source, type, and shape of the antibody. Specifically, a known antibody such as an antibody from a non-human animal (e.g., a mouse antibody, a rat antibody, and a camel antibody), a human antibody, a chimeric antibody, or a humanized antibody can be used. It is preferable that the antibody specifically binds to a Glypican-1 protein. Also, the antibody encompasses modified antibodies and unmodified antibodies. The modified antibodies may be formed by linking various molecules such as polyethylene glycol to antibodies. The modified antibodies can be obtained by chemically modifying an antibody using a known method.

In one embodiment of the present disclosure, the term "monoclonal antibody" encompasses the case where individual antibodies included in the population, excluding a few antibodies having mutations that may naturally occur, correspond to substantially a single epitope. Alternatively, it may also encompass the case where individual antibodies included in the population, excluding a few antibodies having mutations that may naturally occur, may be substantially the same. A monoclonal antibody is highly specific, and is different from a common polyclonal antibody that typically includes different antibodies corresponding to different epitopes. The monoclonal antibody is useful due to its specificity as well as the fact that it can be synthesized through a hybridoma culture that is not contaminated with other immunoglobulins. The expression "monoclonal" may indicate the feature that the antibody is obtained from a substantially homogeneous antibody population, but does not mean that the antibody has to be produced using some specific method. For example, the monoclonal antibody may be produced using a method that is similar to the hybridoma method as described in "Kohler G, Milstein C., Nature. 1975 Aug. 7; 256(5517): 495-497". Alternatively, the monoclonal antibody may be produced using a method that is similar to the recombination method as disclosed in U.S. Pat. No. 4,816,567. The monoclonal antibody may be isolated from a phage antibody library using a method that is similar to the technique as described in "Clacksonet al., Nature. 1991 Aug. 15; 352(6336): 624-628" or "Marks et al., J Mol Biol. 1991 Dec. 5; 222(3): 581-597". The monoclonal antibody may be produced using a method described in "Protein Experiments Handbook, Yodosha Co., Ltd. (2003): 92-96".

Any method known in the art can be used for mass production of antibodies, and, for example, the following is atypical example of construction of an antibody mass-production system and antibody production. That is to say, an H-chain antibody expression vector and an L-chain antibody expression vector are transfected into CHO cells, the cells are cultured with G418 and Zeocin, which are selective reagents, and cloning is performed using a limiting dilution method. After the cloning, a clone that stably expresses the antibody is selected using an ELISA method. The selected CHO cells are subjected to expansion culture, and a culture supernatant containing the antibody is collected. The antibody can be purified from the collected culture supernatant through Protein A purification or Protein G purification. Regarding the humanized antibody of the present disclosure, a polyclonal complete human antibody can be obtained by immunizing a human antibody producing mouse with an antigen of interest, and a monoclonal antibody obtained therefrom can be used in the present disclosure.

In one embodiment of the present disclosure, the "humanized antibody" is, for example, an antibody that has one or more CDRs derived from a non-human species, a framework region (FR) derived from human immunoglobulin, and a constant region derived from human immunoglobulin, and binds to a desired antigen. An antibody can be humanized using various methods known in the art (Almagro et al., Front Biosci. 2008 Jan. 1; 13: 1619-1633). Examples thereof include CDR grafting (Ozaki et al., Blood. 1999 Jun. 1; 93(11): 3922-3930), Re-surfacing (Roguska et al., Proc Natl Acad Sci USA. 1994 Feb. 1; 91(3): 969-973), and FR shuffling (Damschroder et al., Mol Immunol. 2007 April; 44(11): 3049-3060. Epub 2007 Jan. 22). In order to modify (preferably, improve) antigen binding, amino acid residues in the human FR region may be substituted with corresponding residues from a CDR donor antibody. This FR substitution can be performed using a method well known in the art (Riechmann et al., Nature. 1988 Mar. 24; 332(6162): 323-327). For example, an FR residue that is important to antigen binding may be identified by modeling the interaction between the CDR and the FR residues. Alternatively, an abnormal FR residue at a specific position may be identified through sequence comparison. In the humanization, an amino acid in the CDR may or may not be changed. In addition to the description above, a humanized antibody may also be produced as described in "Production Example" of the present disclosure. Specifically, screening from a library of Vx in which a CDR of an antibody derived from a non-human species is grafted into a human heavy chain framework and the heavy chain is fixed may be performed. In this humanization method, the heavy-chain CDR is not changed, but the light-chain CDR may be changed.

In one embodiment of the present disclosure, the "heavy chain" is typically a main constituent element of a full-length antibody. In general, the heavy chain binds to a light chain via a disulfide bond and a non-covalent bond. A region called a variable region (VH) is present in the N-terminal domain of the heavy chain, and the amino acid sequences of the variable regions vary even in antibodies of the same type and the same class. It is commonly known that the VH significantly contributes to specificity and affinity for an antigen. For example, "Reiter et al., J Mol Biol. 1999 Jul. 16; 290(3): 685-98" states that a molecule constituted by only a VH specifically binds to an antigen with high affinity. Furthermore, "Wolfson W, Chem Biol. 2006 December; 13(12): 1243-1244" states that some camel antibodies have only a heavy chain and no light chains.

In one embodiment of the present disclosure, the "CDR (complementarity determining region)" is a region in an antibody that actually comes into contact with an antigen to form a binding site. In general, the CDR is located on the Fv (variable region: including a heavy-chain variable region (VH) and a light-chain variable region (VL)) of an antibody. Also, in general, the CDR includes CDR1, CDR2, and CDR3, which are each constituted by about 5 to 30 amino acid residues. It is known that particularly the CDR of the heavy chain contributes to binding of an antibody to an antigen. It is also known that the contribution of the CDR3 to binding of an antibody to an antigen is the greatest among the CDRs. For example, "Willy et al., Biochemical and Biophysical Research Communications Volume 356, Issue 1, 27 Apr. 2007, Pages 124-128" states that the binding ability of an antibody is increased by modifying the heavy-chain CDR3. A portion of the Fv region other than the CDR is called a framework region (FR), and the framework region includes FR1, FR2, FR3, and FR4 and is relatively highly conserved among antibodies (Kabat et al., "Sequence of Proteins of Immunological Interest" US Dept. Health and Human Services, 1983). That is to say, the factor that characterizes the reactivity of an antibody is the CDR, particularly the heavy-chain CDR.

A plurality of definitions of the CDR and a plurality of methods for determining the position of the CDR have been reported. For example, the Kabat definition (Sequences of Proteins of Immunological Interest, 5th ed., Public Health Service, National Institutes of Health, Bethesda, Md. (1991)) or the Chothia definition (Chothia et al., J. Mol. Biol., 1987; 196: 901-917) may be employed. One embodiment of the present disclosure employs the Kabat definition as a preferred example, but the preferred example is not necessarily limited thereto. In some cases, the CDR may be determined in consideration of both the Kabat definition and the Chothia definition. For example, a portion in which a CDR according to the Kabat definition and a CDR according to the Chothia definition overlap each other, or a portion that includes both a CDR according to the Kabat definition and a CDR according to the Chothia definition, can be taken as the CDR. A specific example of such a method is a method by Martin et al. (Proc. Natl. Acad. Sci. USA, 1989; 86: 9268-9272) in which the Oxford Molecular's AbM antibody modeling software is used, the method being a compromise between the Kabat definition and the Chothia definition. Such information about the CDR can be used to produce a variant that can be used in the present disclosure. Such a variant of an antibody can be produced such that the framework of the original antibody includes one or several (e.g., 2, 3, 4, 5, 6, 7, 8, 9, or 10) substitutions, additions, or deletions, but the CDR includes no mutation.

The term "antigen" as used herein refers to any substrate to which an antibody molecule can specifically bind to. The term "immunogen" as used herein refers to an antigen that can start the activation of lymphocytes that causes antigen-specific immune response. The term "epitope" or "antigenic determinant" as used herein refers to a portion in an antigen molecule to which an antibody or a lymphocyte receptor binds to. A method for determining an epitope is well known in the art, and a person skilled in the art can determine such an epitope using such a well-known common technique when a primary nucleic acid sequence or primary amino acid sequence is provided. It is understood that even an antibody with a sequence different from the sequence of the antibody of the present disclosure can also be used in the same manner as the antibody of the present disclosure as long as the epitopes for these antibodies are the same.

It is understood that an antibody used in this specification may have any specificity as long as a false-positive is reduced.

"Cancer" targeted by the present disclosure includes one or more selected from the group consisting of lung cancer, esophageal cancer, stomach cancer, liver cancer, pancreatic cancer, renal cancer, adrenal cancer, biliary tract cancer, breast cancer, colorectal cancer, small intestinal cancer, ovarian cancer, bile duct cancer, uterine cancer, bladder cancer, prostate cancer, ureteral cancer, renal pelvis cancer, ureteral cancer, penile cancer, testicular cancer, brain tumor, central nervous system cancer, peripheral nervous system cancer, head and neck cancer, glioma, glioblastoma multiforme, skin cancer, melanoma, thyroid cancer, salivary gland cancer, malignant lymphoma, carcinoma, sarcoma, leukemia, and hematological malignancy. The term "cancer" is used interchangeably with the terms "carcinoma" and "tumor". Here, ovarian cancer includes, for example, ovarian serous adenocarcinoma and ovarian clear cell adenocarcinoma. Uterine cancer includes, for example, endometrial cancer and cervical cancer. Head and neck cancer includes, for example, oral cancer, pharyngeal cancer, laryngeal cancer, nasal cavity cancer, nasal sinus cancer, salivary gland cancer, and thyroid cancer. Lung cancer includes, for example, non-small cell lung cancer and small-cell lung cancer. Malignant tumor may be PD-L1-positive tumor.

The term "esophageal cancer" as used herein is given its ordinary meaning, and is used in a broad sense encompassing cancer that appears in the esophagus. Esophageal cancer encompasses, but is not limited to, squamous cell cancer as well as adenocarcinoma, lymph-node metastatic cancer, and the like. It is known that esophageal cancer appears near the center of the esophagus in the chest in about a half of Japanese patients while it appears in a lower portion of the esophagus in a quarter of Japanese patients, and it is understood that the present disclosure covers both cases. Without wishing to be bound by theory, it is expected that the present disclosure can be used as an indicator for all kinds of esophageal cancer including squamous cell cancer as well as adenocarcinoma and lymph-node metastatic cancer.

The term "pancreatic cancer" as used herein refers to malignant tumor that appears in the pancreas, but this term generally refers to pancreatic duct cancer. In this specification, tumors that appear in other portions of the pancreas are also encompassed.

The term "cervical cancer" as used herein refers to one type of uterine cancer. Uterine cancer includes cervical cancer and uterine body cancer. Cervical cancer appears in a portion at the entrance of the uterus, which is called the uterine cervix.

The term "lung cancer" as used herein refers to malignant tumor that appears from epithelial cells of the lung, and includes small cell lung cancer, non-small cell lung cancer, and the like. Non-small cell lung cancer includes adenocarcinoma, squamous cell cancer and large cell cancer.

The term "head and neck cancer" as used herein refers to tumor in the head and neck region, and specifically refers to tumor that appears in a portion ranging from the face to the neck such as the nose, the mouth, the throat, the upper jaw, the lower jaw, or the ear.

The term "breast cancer" as used herein refers to tumor that appears in the breast, and includes ductal breast cancer, lobular cancer, and the like.

The term "uterine leiomyosarcoma" as used herein refers to one type of uterine sarcoma that appears in the uterine smooth muscle. Uterine leiomyosarcoma can be histologically diagnosed based on the cell density, the number of cell division, the cellular atypism, and whether or not coagulation necrosis of tumor cells occurs.

The term "prostate cancer" as used herein refers to tumor that appears in the prostate.

The term "oral squamous cell cancer" as used herein refers to tumor that is one type of oral cancer and appears in the epithelium of the oral mucous membrane.

The term "bile duct cancer" as used herein refers to tumor that appears in the bile duct. "Bile duct cancer" is classified into intrahepatic bile duct cancer, which appears in the bile duct in the liver, perihilar bile duct cancer, which appears in the hepatic portal region outside the liver, and distal bile duct cancer, which appears in the distal portion outside the liver.

The term "cancer-associated fibroblasts (CAFs)" as used herein refers to fibroblasts that constitute the stroma of cancer. CAFs produce a large amount of extracellular matrix such as collagen, which considerably hardens the stroma of cancer. As a result, compression (collapse) of the blood vessels and the like occur, and thus efficient infiltration of an anti-cancer agent is prevented. Compression of blood vessels also induces the hypoxic state of a cancer tissue, and furthermore increases the malignancy of cancer cells. An increase in the hardness of stroma itself is one of the factors that improve the proliferation and invasive capacity (ability to spread over the surrounding tissue) of cancer cells. In addition, CAFs produce a large amount of growth factors, and the growth factors act on cancer cells to promote the proliferation and invasion thereof, and suppress anti-tumor immune response.

The term "stroma" of cancer refers to a tissue that surrounds cancer cells in a cancer tissue, includes CAFs as a main constituent component, and includes, as other constituent components, immune cells, bone marrow-derived cells, tumor vessels, lymph vessels, extracellular matrix produced by CAFs, and the like.

The term "subject (human subject)" as used herein refers to a target (e.g., a living organism such as a human, or cells, blood, serum, or the like removed from a living organism) to be subjected to diagnosis or detection, or treatment etc. of the present disclosure.

The term "sample" as used herein refers to any substance obtained from a subject or the like, and includes, for example, serum and the like. A person skilled in the art can select a preferred sample as appropriate based on the description in this specification.

The terms "medicine", "agent", and "factor" as used herein are used interchangeably in a broad sense, and may refer to any substance or another element (e.g., energy such as light, radiation, heat, and electricity) as long as the intended object can be achieved. Examples of such a substance include, but are not limited to, a protein, a polypeptide, an oligopeptide, a peptide, a polynucleotide, an oligonucleotide, a nucleotide, a nucleic acid (including DNA such as cDNA and genome DNA, and RNA such as mRNA, for example), a polysaccharide, an oligosaccharide, a lipid, a low-molecular-weight organic molecule (e.g., a hormone, a ligand, a messenger, a low-molecular-weight organic molecule, a molecule synthesized thorough combinatorial chemistry, or a low-molecular-weight molecule that can be used as a pharmaceutical drug (e.g., low-molecular-weight ligand)), and a complex molecule thereof. Glypican-1-binding substances can also be included in such medicines. Typical examples of a factor specific to a polynucleotide include, but are not limited to, a complementary polynucleotide having a certain sequence homology (e.g., 70% or more sequence identity) to the sequence of the polynucleotide, and a polypeptide such as a transcription factor that binds to a promoter region. Typical examples of a factor specific to a polypeptide include, but are not limited to, an antibody directed specifically to the polypeptide, or a derivative thereof or an analogue thereof (e.g., single-chain antibody), a specific ligand or receptor (in the case where the polypeptide is a receptor or ligand), and a substrate (in the case where the polypeptide is an enzyme).

The term "diagnosis" as used herein means that various parameters related to a disease, disorder, condition (e.g., esophageal cancer), or the like in a subject are identified to determine the current state and the future of such a disease, disorder, or condition. The method, apparatus, or system of the present disclosure can be used to check the condition in the body, and the thus obtained information can be used to select various parameters for a disease, disorder, or condition in a subject, treatment to be administered, or a formulation or method for prevention. The term "diagnosis" as used herein refers to diagnosing the current state in a narrow sense, and encompasses "early diagnosis", "predictive diagnosis", "preliminary diagnosis", and the like in a broad sense. In principle, a substance collected from the body can be used in a diagnostic method of the present disclosure, and thus this method is industrially useful because it can be carried out by a person other than a healthcare worker such as a medical doctor. In order to clarify that the method can be carried out by a person other than a healthcare worker such as a medical doctor, the expression that "predictive diagnosis, preliminary diagnosis, or diagnosis" is "supported" is employed in some portions of this specification.

The term "detection reagent (agent)" or "test reagent (agent)" as used herein refers to any medicine that can be used to detect or test a target of interest in a broad sense.

The term "diagnostic reagent (agent)" as used herein refers to any medicine that can be used to diagnose a condition of interest (e.g., a disease such as esophageal cancer) in a broad sense.

The term "treatment" as used herein refers to preventing exacerbation of a certain disease or disorder (e.g., esophageal cancer) that is developed, preferably maintaining a current level of the disease or disorder, more preferably alleviating the disease or disorder, and even more preferably curing the disease or disorder completely, and encompasses being capable of exhibiting an effect of improving or preventing a disease of a patient or one or more symptoms of the disease. Giving appropriate treatment based on preliminary diagnosis is referred to as "companion treatment", and a diagnostic reagent for the companion treatment may be referred to as a "companion diagnostic reagent".

The term "therapeutic reagent (agent)" as used herein refers to any medicine that can be used to treat a condition of interest (e.g., a disease such as esophageal cancer) in a broad sense. In one embodiment of the present disclosure, the "therapeutic reagent" may be a pharmaceutical composition that includes an active ingredient and one or more pharmacologically acceptable carriers. The pharmaceutical composition can be produced by, for example, mixing an active ingredient and the above-mentioned carrier and performing any method known in the formulation art. The therapeutic reagent may be used in any form as long as it is used for treatment, and only an active ingredient may be used or a mixture of an active ingredient and any component may be used. Also, there is no particular limitation on the form of the above-mentioned carrier, and the carrier may be in, for example, a solid form or liquid form (e.g., buffer solution). Note that a therapeutic reagent for esophageal cancer includes a drug used to prevent esophageal cancer (preventive reagent), or an esophageal cancer cell growth inhibitor.

The term "prevention" as used herein refers to an attempt to prevent the development of a certain disease or disorder (e.g., esophageal cancer) before onset of the disease or disorder. The medicine of the present disclosure can be used for diagnosis. The medicine of the present disclosure can be used as needed to prevent esophageal cancer or take measures for prevention.

The term "preventive reagent (agent)" as used herein refers to any medicine that can be used to prevent a condition of interest (e.g., a disease such as esophageal cancer) in a broad sense.

The term "interaction" as used herein means that each of two substances exert a force (e.g., intermolecular force (van der Waals force), hydrogen bond, or hydrophobic interaction) on each other. In general, two interacting substances are associated with or linked to each other. The detection, testing, and diagnosis of the present disclosure can be realized by utilizing such interaction.

In this specification, the "detection" or "quantification" of the expression of a polynucleotide or polypeptide can be achieved by, for example, using an appropriate method including an mRNA measurement method and an immunological measurement method that utilize binding to or interaction with a detection agent, test agent, or diagnostic agent (including application as a companion reagent). Examples of a molecular biological measurement method include northern blotting, dot blotting, and a PCR technique. Examples of the immunological measurement method include ELISA in which a microtiter plate is used, RIA, a fluorescent antibody technique, luminescence immunoassay (LIA), an immune precipitation technique (IP), an immunodiffusion technique (SRID), turbidimetric immunoassay (TIA), western blotting, and immunohistological staining. Examples of the quantification method include ELISA and RIA. The quantification may also be performed using a gene analysis method in which an array (e.g., DNA array or protein array) is used. Abroad outline of the DNA array is given in an extra issue of Cell Engineering "DNA Microarray and Latest PCR Technique", edited by Shuiunsha Co., Ltd. Details of the protein array is described in Nat Genet. 2002 December; 32 Suppl: 526-532. Examples of the method for analyzing gene expression include, but are not limited to, RT-PCR, a RACE technique, an SSCP technique, an immune precipitation technique, a two-hybrid system, and an in-vitro translation in addition to the above-described methods. Such further analysis methods are described in, for example, "Genomics Experiments—Yusuke Nakamura Laboratory Manual", edited by Yusuke Nakamura, Yodosha Co., Ltd. (2002), etc., which is incorporated herein by reference in its entirety.

The term "reduction" or "suppression" or synonyms thereof as used herein for activity and expression products (e.g., proteins and transcripts (such as RNA)) refers to a reduction of the amount, quality, or effect of a specific activity, transcript, or protein, or activity for reducing the amount, quality, or effect of a specific activity, transcript, or protein. If the activity, expression products, and the like are reduced until they are undetectable, that is, they are reduced to fall below the detection limits, the term "disappearance" may be particularly used. In this specification, "disappearance" is encompassed in "reduction" and "suppression".

The term "label" as used herein refers to an entity (e.g., substance, energy, or electromagnetic wave) for distinguishing a molecule or substance of interest from others. Examples of such a labeling method include an RI (radioisotope) method, a fluorescence method, a biotin method, and a chemiluminescence method. When a plurality of markers of the present disclosure, or factors or measures for capturing the markers are labeled through the fluorescence method, fluorescent substances that differ from one another in the fluorescent emission maximum wavelength are used. A difference in the fluorescent emission maximum wavelengths is preferably 10 nm or more. When a ligand is labeled, any fluorescent substance can be used as long as it has no influence on the functions of the ligand, but a desirable fluorescent substance is Alexa (trademark) Fluor. Alexa (trademark) Fluor is a water-soluble fluorescent dye obtained by modifying coumarin, rhodamine, fluorescein, cyanine, or the like, and a series thereof corresponds to a wide range of fluorescence wavelengths, and is very stable, produces bright fluorescence, and has a lower pH sensitivity than other fluorescent dyes for corresponding wavelengths. Examples of a combination of fluorescent dyes whose fluorescent emission maximum wavelengths differ from each other by 10 nm or more include a combination of Alexa (trademark) 555 and Alexa (trademark) 633, and a combination of Alexa (trademark) 488 and Alexa (trademark) 555. When a nucleic acid is labeled, any label can be used as long as it can bind to the base moiety of the nucleic acid, but it is preferable to use a cyanine dye (e.g., Cy3 and Cy5 of CyDye (trademark) series), a rhodamine 6G reagent, 2-acetylaminofluorene (AAF), and AAIF (iodine derivative of AAF). Examples of a combination of fluorescent substances whose fluorescent emission maximum wavelengths differ from each other by 10 nm or more include a combination of Cy5 and the rhodamine 6G reagent, a combination of Cy3 and fluorescein, and a combination of the rhodamine 6G reagent and fluorescein. In the present disclosure, such a label can be used to alter a target of interest such that detection means can be used to detect the target. Such an alteration is known in the art, and a person skilled in the art can perform such a method as appropriate in accordance with a label and a target of interest.

The term "in vivo" as used herein refers to the inside of a living organism. In a specific context, the wording "inside a living organism" refers to a position at which a substance of interest is to be arranged.

The term "in vitro" as used herein refers to a state in which a part of a living organism is extracted or isolated "out of the living organism" (e.g., into a test tube) for various research purposes. This term is used in contrast with the term "in vivo".

The term "ex vivo" as used herein refers to a series of operations in a certain procedure when it is intended to perform the procedure outside the body first and then back inside the body. In the present disclosure as well, an embodiment can be assumed in which cells obtained from the inside of a living organism are treated with the medicine of the present disclosure and are then returned into a patient again.

The term "kit" as used herein refers to a unit whose parts (e.g., a test reagent, a diagnostic reagent, a therapeutic reagent, an antibody, a label, and an operation manual) to be provided are generally divided into two or more components and provided in that manner. This form of a kit is preferable for the purpose of providing a composition that should not be provided as a mixture in consideration of its stability and the like and is preferably prepared as a mixture just before use. It is advantageous that such a kit includes an instruction or operation manual that preferably describes how to use the parts (e.g., a test reagent, a diagnostic reagent, and a therapeutic reagent) to be provided, or how to treat the reagent. When the kit is used as a reagent kit in this specification, the kit generally includes an instruction or the like that describes how to use a test reagent, a diagnostic reagent, a therapeutic reagent, an antibody, and the like.

In this specification, the "instruction" describes a way to use the present disclosure for medical doctors or other users. This instruction describes the detection method of the present disclosure, a way to use a diagnostic reagent, and written instructions to administer a pharmaceutical drug. Also, the instruction may describe written instructions about administration sites such as oral administration and intraesophageal administration (by injection or the like, for example). This instruction is prepared in accordance with the form prescribed by the competent authority (e.g., the Ministry of Health, Labour and Welfare in Japan, and the Food and Drug Administration (FDA) in the U.S.) in a country where the present disclosure is implemented, and states clearly that the present disclosure is approved by the competent authority. The instruction is what is called a package insert and is generally provided as a print medium, but there is no limitation thereto. For example, the instruction may also be provided in the form of an electronic medium (e.g., a web site provided on the Internet or an e-mail) or the like.

The term "cell entry (internalize/internalization)" as used herein refers to a phenomenon in which a cell takes in a substance binding to an antigen on the surface of the cell through endocytosis or phagocytosis, which are mediated by the substance binding to the antigen. A substance (e.g., anti-Glypican-1 antibody) that has such activity and binds to Glypican-1 can transfer an active ingredient of interest into a cell that expresses Glypican-1 on the cell surface, and cause the active ingredient of interest to exhibit a desired effect in the Glypican-1 expressing cell. Examples of the active ingredient of interest include, but are not limited to, a medicine having cytotoxic activity, an anti-cancer agent, a contrast medium, an siRNA, an antisense nucleic acid, and ribozyme.

The term "complex" as used herein refers to any construct that includes two or more moieties. For example, if one moiety is a polypeptide, the other moiety may be a polypeptide or another substance (e.g., saccharide, lipid, nucleic acid, another hydrocarbon, and low-molecular-weight compound). In this specification, the two or more moieties included in the complex may be linked together via covalent bonds or other bonds (e.g., hydrogen bonds, ionic bonds, hydrophobic interaction, and van der Waals force). Accordingly, in this specification, the "complex" encompasses molecules formed by a plurality of types of molecules such as a polypeptide, a nucleic acid, a lipid, a saccharide, and a low-molecular-weight compound linking together.

The term "linker" as used herein refers to a molecule that couples at least two constituent elements while separating them spatially. Examples of the linker include, but are not limited to, an enzyme cleavable linker, an acid labile linker, and disulfide linker. The term "enzyme cleavable linker" refers to a linker that is cleaved by an enzyme present inside a cell. The term "acid labile linker" refers to a linker that can be cleaved under acidic conditions of endosomes or lysosomes inside a cell. The term "disulfide linker" refers to a linker that can be cleaved under reduced conditions inside a cell.

The term "antigen-drug complex (ADC)" as used herein refers to an antibody or an antigen-binding fragment of the antibody that is chemically linked to one or more active ingredients of interest. In a preferred embodiment, an ADC is operably linked via a linker. The wording "operably linked" as used herein refers to a state in which constituent elements are linked together such that each of them can exhibit its functions. Examples of the active ingredient of interest that can be included in the ADC include, but are not limited to, a medicine having cytotoxic activity, an anti-cancer agent, a contrast medium, an siRNA, an antisense nucleic acid, and ribozyme. A cleavable linker or non-cleavable linker may be used as the linker. Examples of the cleavable linker include, but are not limited to, a linker having a sequence that is cleaved by a protease, an acid labile linker, and a disulfide linker. An example of the non-cleavable linker is an MCC linker, but there is no limitation thereto.

The term "cytotoxic activity" as used herein refers to activity for bringing about cell death through direct or indirect blockage of cell functions caused by not only a pathological change brought about to a cell and a direct external injury to a cell but also damage to any cell structures and cell functions of a cell such as cleavage of DNA, formation of a base dimer, cleavage of a chromosome, damage to the cell division system, and decreases in various enzyme activities. Accordingly, examples of the "medicine having cytotoxic activity" include, but are not limited to, an alkylating agent, a tumor necrosis factor inhibitor, an intercalator, a microtubule inhibitor, a kinase inhibitor, a proteasome inhibitor, and a topoisomerase inhibitor.

The term "50% inhibitory concentration ($IC_{50}$)" as used herein refers to a concentration of a compound required to kill 50% of cells. In this specification, $IC_{50}$ is measured using a method described in Example 7.

The term "affinity" as used herein refers to an equilibrium constant of a reversible bond between two substances (e.g., an antibody and an antigen), and is expressed as an equilibrium dissociation constant ($K_D$ value). The equilibrium dissociation constant can be measured through a surface plasmon resonance (SPR) technique using, for example, Biacore (registered trademark). In addition, MP-SPR Navi (trademark) (BioNavis), OpenPlex (Horiba), and Smart SPR (RIBM) may also be used to measure the equilibrium dissociation constant. The $K_D$ values shown in the present disclosure are measured through the surface plasmon resonance (SPR) technique unless otherwise specified.

Preferred Embodiments

Hereinafter, preferred embodiments of the present disclosure will be described. The embodiments below are provided for a better understanding of the present disclosure, and it is understood that the scope of the present disclosure should not be limited to the description below. Accordingly, it is clear that a person skilled in the art can take the description in this specification into consideration and make alterations as appropriate within the scope of the present disclosure. It is also understood that the following embodiments of the present disclosure can be used alone or in combination.

Antibody

In one aspect, the present disclosure provides a humanized anti-GPC-1 antibody humanized based on an antibody that includes a heavy-chain variable region having an amino acid sequence set forth in SEQ ID NO: 5 and a light-chain variable region having an amino acid sequence set forth in SEQ ID NO: 6, or an antigen-binding fragment of the humanized anti-GPC-1 antibody. The inventors of the present invention humanized an anti-GPC-1 mouse monoclonal antibody 01a033 (that includes a heavy-chain variable region represented by SEQ ID NO: 5 and a light-chain variable region represented by SEQ ID NO: 6) having high affinity to GPC-1, which is disclosed in WO 2018/199318 (incorporated by reference herein), and thereby unexpectedly succeeded in obtaining a humanized antibody having higher affinity than that of 01a033. Accordingly, the humanized antibody of the present disclosure may have higher affinity to GPC-1 than that of an antibody that includes a heavy-chain variable region having an amino acid sequence set forth in SEQ ID NO: 5 and a light-chain variable region having an amino acid sequence set forth in SEQ ID NO: 6.

In some embodiments, the antibody of the present disclosure or the antigen-binding fragment thereof may include a heavy-chain variable region having an amino acid sequence set forth in SEQ ID NO: 7, or an amino acid sequence with at least about 90% identity, at least about 95% identity, at least about 96% identity, at least about 97% identity, at least about 98% identity, or at least about 99% identity thereto.

In some embodiments, the antibody of the present disclosure or the antigen-binding fragment thereof may include a light-chain variable region having an amino acid sequence selected from the group consisting of amino acid sequences set forth in SEQ ID NOs: 8 to 27, or an amino acid sequence with at least about 90% identity, at least about 95% identity, at least about 96% identity, at least about 97% identity, at least about 98% identity, or at least about 99% identity thereto. In preferred embodiments, the antibody of the present disclosure or the antigen-binding fragment thereof may include a light-chain variable region having an amino acid sequence selected from the group consisting of amino acid sequences set forth in SEQ ID NOs: 8 to 17, or an amino acid sequence with at least about 90% identity, at least about 95% identity, at least about 96% identity, at least about 97% identity, at least about 98% identity, or at least about 99% identity thereto.

In some embodiments, the antibody of the present disclosure may be of any class, and may be, for example, IgM, IgD, IgG, IgA, IgE, or IgY In a specific embodiment, the antibody of the present disclosure may be IgG. In a further specific embodiment, the antibody of the present disclosure is of a subclass selected from the group consisting of human IgG1, human IgG2, human IgG3, and human IgG4, and is preferably human IgG4.

It is known that a human IgG4 H chain exchange reaction (Fab-arm exchange) occurs between one human IgG4 and another human IgG4 (www.nature.com/articles/nmeph.2015.95/figures/2). In order to prevent this reaction, S228P mutation can be introduced (J Biol Chem. 2015 Feb. 27; 290 (9): 5462-9). For example, in OPDIVO (nivolumab) and KEYTRUDA (pembrolizumab), S228P mutation is introduced, and in dupilumab, the amino acid residue at position 233 of the H chain is substituted with Pro. In the classes other than human IgG4, the Fab-arm exchange does not occur, and thus amino acid mutation need not be introduced.

In some embodiments, the antibody of the present disclosure may include a heavy-chain constant region having an amino acid sequence set forth in SEQ ID NO: 91, or an amino acid sequence with at least about 90% identity, at least about 95% identity, at least about 96% identity, at least about 97% identity, at least about 98% identity, or at least about 99% identity thereto. In some embodiments, the antibody of the present disclosure may include a light-chain constant region having an amino acid sequence set forth in SEQ ID NO: 92, or an amino acid sequence with at least about 90% identity, at least about 95% identity, at least about 96% identity, at least about 97% identity, at least about 98% identity, or at least about 99% identity thereto.

In some embodiments, CDRs 1 to 3 of the heavy-chain variable region may have amino acid sequences set forth in SEQ ID NOs: 28 to 30, respectively.

In some embodiments, CDRs 1 to 3 of the light-chain variable region may have amino acid sequences set forth in SEQ ID NOs: 31 to 33, respectively, or SEQ ID NOs: 34 to 36, respectively, or SEQ ID NOs: 37 to 39, respectively, or SEQ ID NOs: 40 to 42, respectively, or SEQ ID NOs: 43 to 45, respectively, or SEQ ID NOs: 46 to 48, respectively, or SEQ ID NOs: 49 to 51, respectively, or SEQ ID NOs: 52 to 54, respectively, or SEQ ID NOs: 55 to 57, respectively, or SEQ ID NOs: 58 to 60, respectively, or SEQ ID NOs: 61 to 63, respectively, or SEQ ID NOs: 64 to 66, respectively, or SEQ ID NOs: 67 to 69, respectively, or SEQ ID NOs: 70 to 72, respectively, or SEQ ID NOs: 73 to 75, respectively, or 76 to 78, or 79 to 81, or 82 to 84, or 85 to 87, or SEQ ID NOs: 88 to 90, respectively. In preferred embodiments, CDRs 1 to 3 of the light-chain variable region may have amino acid sequences set forth in SEQ ID NOs: 31 to 33, respectively, or SEQ ID NOs: 34 to 36, respectively, or SEQ ID NOs: 37 to 39, respectively, or SEQ ID NOs: 40 to 42, respectively, or SEQ ID NOs: 43 to 45, respectively, or SEQ ID NOs: 46 to 48, respectively, or SEQ ID NOs: 49 to 51, respectively, or SEQ ID NOs: 52 to 54, respectively, or SEQ ID NOs: 55 to 57, respectively, or SEQ ID NOs: 58 to 60, respectively.

In some embodiments, the epitope of the antibody of the present disclosure or the antigen-binding fragment thereof may include positions 339 to 358 and/or 388 to 421 of SEQ ID NO: 2 (full-length sequence of human GPC-1). In a specific embodiment, the epitope of the antibody of the present disclosure may include positions 339 to 358 and 388 to 421 of SEQ ID NO: 2 (full-length sequence of human GPC-1).

In some embodiments, the antibody of the present disclosure or the antigen-binding fragment thereof may bind to Glypican-1 with affinity ($K_D$ value) of about $5\times10^{-9}$ M, about $6\times10^{-9}$ M, about $7\times10^{-9}$ M, about $8\times10^{-9}$ M, about $9\times10^{-9}$ M, about $10^{-8}$M or less, about $2\times10^{-8}$ M, about $3\times10^{-8}$ M, about $4\times10^{-8}$ M, about $5\times10^{-8}$ M, about $10^{-7}$ M, or about $5\times10^{-7}$ M. In a specific embodiment, the antibody of the present disclosure or the antigen-binding fragment thereof may bind to Glypican-1 with affinity ($K_D$ value) of $3.16\times10^{-8}$ M or about $1.02\times10^{-8}$ M.

In a further aspect, the present disclosure provides a pharmaceutical composition for transferring an active ingredient into a cell, the composition including the humanized antibody of the present disclosure or the antigen-binding fragment thereof. The antibody of the present disclosure unexpectedly has cell entry (internalization) activity greater than or equal to that of 01a033.
Complex In a further aspect, the present disclosure provides a complex of the humanized antibody of the present disclosure or the antigen-binding fragment thereof and a medicine having cytotoxic activity. The medicine having cytotoxic activity may be operably linked to the humanized antibody or the antigen-binding fragment thereof via a linker.

Examples of the medicine having cytotoxic activity include, but are not limited to, monomethyl auristatin E (MMAE), monomethyl auristatin F (MMAF), DM1, DM4, calicheamicin, duocarmycin, pyrrolobenzodiazepine (PBD), and topoisomerase inhibitors. The medicine having cytotoxic activity preferably has a bystander effect, which is not intended to be limiting. The "bystander effect" refers to a phenomenon in which a medicine released inside a cancer cell passes through the cell membrane and also has an effect on surrounding cancer cells. Accordingly, in some embodiments, the medicine having cytotoxic activity may have cell permeability. Examples of the medicine having cytotoxic activity and a bystander effect include, but are not limited to, MMAE, PBD, Eribulin, SN-38, Dxd, and DM4.

In some embodiments, it is sufficient that the linker is cleaved in a cancer cell, and examples thereof include an enzyme cleavable linker, an acid labile linker, and disulfide linker. In a specific embodiment, the linker may be a cleavable linker that is cleaved by cathepsin (e.g., cathepsin B), such as maleimidecaproyl-valine-citrulline-p-aminobenzyloxycarbonyl.

In some embodiments, the complex of the present disclosure may show an $IC_{50}$ of about 0.04 nM or less, about 0.05 nM or less, about 0.06 nM or less, about 0.07 nM or less, about 0.08 nM or less, about 0.09 nM or less, about 0.1 nM or less, about 0.11 nM or less, about 0.12 nM or less, about 0.13 nM or less, about 0.14 nM or less, or about 0.15 nM or less in a Glypican-1-positive cell. $IC_{50}$ may be a value measured through the ADC assay of Example 2. In preferred embodiments, the complex may show an $IC_{50}$ of about 0.1 nM or less in a Glypican-1-positive cell.

In another embodiment, the linker used in the complex of the present disclosure may be an acid labile linker. Given that an acidic pH condition inside an endosome or lysosome is utilized after transfer into a cell, pH-responsive linker that is labile under an acidic condition can be used. An example of such a linker is hydrazone.

In yet another embodiment, the linker used in the complex of the present disclosure may be a disulfide linker, and examples of such a linker include N-succinimidyl 4-(2-pyridyldithio)butanoate (SPDB) and N-succinimidyl 4-(2-pyridyldithio)pentanoate (SPP).

The linker used in the complex of the present disclosure may be a non-cleavable linker. An example of the non-cleavable linker is maleimidomethylcyclohexane-1-carboxylic acid (MCC linker), but there is no limitation thereto.
Pharmaceutical Composition In a further aspect, the present disclosure provides a composition for preventing or treating Glypican-1-positive cancer, the composition including the complex of the present disclosure. The Glypican-1-positive cancer may be selected from esophageal cancer, pancreatic cancer, bile duct cancer, cervical cancer, lung cancer, head and neck cancer, breast cancer, uterine leiomyosarcoma, prostate cancer, oral squamous cell cancer, and any combinations thereof. In a specific embodiment, the Glypican-1-positive cancer may be esophageal cancer or pancreatic cancer.
Composition for Treating Metastatic Cancer In a further aspect, a composition for preventing or treating metastatic cancer of Glypican-1-positive cancer is provided, the composition including the complex of the present disclosure. The inventors of the present invention found that metastatic cancer of Glypican-1-positive cancer expresses Glypican-1, and the complex of the present disclosure can be used to treat metastatic cancer of Glypican-1-positive cancer. The same antigen as an antigen expressed at a primary cancer site is not always expressed in a metastatic cancer. Therefore, it is necessary to confirm whether or not a cancer antigen that has been proven to be expressed in the primary cancer site is expressed in metastatic cancer. It has been proven that GPC1 is expressed in a metastatic tumor tissue such as lymph node metastasis of pancreatic cancer, liver metastasis of pancreatic cancer, and lymph node metastasis of esophageal cancer, and that GPC1 is effective as a treatment target.

In some embodiments, the Glypican-1-positive cancer may be selected from esophageal cancer, pancreatic cancer, bile duct cancer, cervical cancer, lung cancer, head and neck cancer, breast cancer, uterine leiomyosarcoma, prostate cancer, oral squamous cell cancer, and any combinations thereof. In a specific embodiment, the Glypican-1-positive cancer may be pancreatic cancer.

In some embodiments, the metastatic cancer may be metastatic cancer that has metastasized to the liver, esophagus, bile duct, cervix, lung, head and neck region, breast, uterine smooth muscle, prostate, oral squamous epithelium, brain, bone, peritoneum, or adrenal.

In some embodiments, the cancer may include cancer-associated fibroblasts (CAFs).

In a further embodiment, the complex of the present disclosure may be administered together with an immune checkpoint inhibitor. Examples of the immune checkpoint inhibitor include, but are not limited to, an anti-PD-1 antibody, an anti-PD-L1 antibody, an anti-CTLA-4 antibody, and an anti-VISTA antibody.

Production of Variant

A person skilled in the art can produce a variant having affinity to GPC-1 higher than or equal to that of 01a033 or the antibody of the present disclosure based on the sequence of the antibody of the present disclosure in accordance with a method well known in the art. For example, a person skilled in the art can analyze antibodies whose CDRs have slightly different sequences using a phage display technique and screen antibodies having affinity higher than or equal to that of an antibody of interest. Other examples of the method for producing a variant include a CDR-walking method and a random mutagenesis method. In some embodiments, the variant may be produced by performing substitution, deletion and/or addition of three or less amino acids, preferably substitution, deletion and/or addition of two or less amino acids, and more preferably substitution, deletion and/or addition of one or less amino acids, on the CDRs of the antibody of the present disclosure or the antigen-binding fragment thereof. The affinity of these variants to GPC-1 may be higher than or equal to that of 01a033 or the antibody of the present disclosure.

In this specification, the term "or" is used when "at least one" of listed items in the text can be employed. The same applies to all cases where "or" is used. In this specification, when the wording "within a range between two values" is clearly stated, this range also includes these two values.

The references such as scientific literature, patents, and patent applications cited herein are incorporated herein by reference in their entireties as if specifically set forth.

The present disclosure has been described with reference to preferred embodiments to facilitate understanding. Hereinafter, the present disclosure will be described with reference to examples. However, the descriptions above and the examples below are provided by way of example only, and are not provided for limiting the present disclosure. Accordingly, the scope of the present disclosure is not limited by the embodiments and the examples that are specifically described herein, and is limited by only the appended claims.

EXAMPLES

Hereinafter, examples will be described. When necessary, the animals used in the examples below were treated in accordance with the Declaration of Helsinki while complying with the standards defined by the National Institute of Biomedical Innovation. Regarding the reagents, the product that are specifically described in the examples were used, but equivalents available from other manufacturers (e.g., Sigma-Aldrich, Wako Pure Chemical Industries Ltd., Nacalai Tesque Inc., R&D Systems, and USCN Life Science Inc) can be used instead.

The objects of the examples are as follows: the anti-GPC1-monoclonal antibody (clone 01a033) discovered as an antibody having high cell-internalization activity is humanized, cell-internalization activity higher than that before the humanization is screened, humanized GPC1-ADC is produced by linking an anti-cancer agent to humanized anti-GPC1 monoclonal antibody via a linker, and the anti-tumor effect of the humanized GPC1-ADC is demonstrated in vitro and in vivo. In addition, payload MMAE has the property of inducing immunogenic cell death, and therefore, another object is to confirm that using the humanized GPC1-ADC and an immune checkpoint inhibitor together provides a synergistic anti-tumor effect.

Production Example: Production of Humanized Antibody

Production of the humanized antibody of the present disclosure was ordered from HD Biosciences (China) Co., Ltd.

Briefly speaking, humanization was performed simply through construction of a library, antigen panning and screening, binding ELISA, and determination of affinity. A human Vx library was constructed using CDRs of mouse antibodies and fixed heavy chains of human frameworks, and then antigen panning and screening were performed. Thirty humanized anti-glypican-1 antibodies in total were found through panning of the Vx library, and were checked through phage ELISA. Twenty antibodies were selected therefrom for expression and purification of antibodies, and then the affinity was determined using Biacore (registered trademark) 8K.

Materials and Methods

Construction of Antibody Library

Production of Humanized H Chain VH Region through CDR Grafting of Mouse Antibody (01a033)

Alleles having high homology to the VH of 01a033 were searched using the abYsis database, and the framework of the human germ cell line sequence VH1-46 was selected to produce a gene corresponding to an amino acid sequence obtained by grafting the CDR sequence of the VH of 01a033.

As for the VL region, the library of human VL gene pool (LC-Library: Library diversity $4.53 \times 10^5$/Library size $1.06 \times 10^{13}$) was used. A VL library gene, the Ck gene, the above-mentioned humanized VH gene, and CH1 were inserted in this order on the N terminal side of a phage GIII antigen.

A phage library constituted by random human L chains (k) and the humanized H chain (VH+CH1) having the 01a033 CDR sequence was produced (humanized antibody library).

Panning

Panning was performed to select phages expressing an antibody that actually binds to GPC-1, from the humanized antibody library.

The antigen GPC-1 was linked to a solid phase (test tube, particles), and a phage population was added thereto. Then, the solid phase was washed, and the bound phages were collected.

Isolation of Phage Clone Through Filter Lifting and Verification of Antigen-Binding Ability The phages that bound to the antigen during panning and were then eluted were allowed to infect *E. coli* seeded on a plate. Then, generated plaques were transferred to a filter, and the phages were cloned.

The obtained phage clones were amplified, and the binding ability of each clone in ELISA (human GPC-1 antigen was immobilized) was checked. Clones that provided a binding signal higher than or equal to a certain value were selected.

Expression and Purification of IgG Derived from Antibody Clone

Antibodies in the form of IgG derived from the genes of the selected twenty phage clones were expressed in HEK293 cells (vector: pFUSE2ss-CLIg-hkpFUSE2ss-CLIg-hk (light chain, Invivogen, Catalog No.: pfuse2ss-hclk) and pFUSEss-CHIg-hGl (heavy chain, Invivogen, Catalog No.: pfusess-hchgl); cell line: FreeStyle (trademark) 293F Cells (Invitrogen, Catalog No.: R790-07)). On Day 4 after transfection, the antibodies were purified from culture supernatants, and were subjected to quantification and SDS-PAGE analysis. All the twenty clones were subjected to analysis on antibody production (presence of the H chain and L chain, and molecular weights thereof).

Measurement of Antigen-Binding Affinity of Clones Through Surface Plasmon Resonance Technique The antigen-binding affinity of each of the obtained twenty clone antibodies was measured through surface plasmon resonance technique (Biacore (registered trademark) 8K). An anti-human-IgG antibody was immobilized on a chip, and each antibody was flowed thereon and allowed to bind thereto. After washing, the human GPC-1 antigen was flowed thereon, and the binding constant (Ka) and the dissociation constant (Kd) were measured. Seven clones had affinity higher than that of the mouse antibody.

Measurement of Antigen-Binding Affinity of Mouse Antibody (01a033) Through Surface Plasmon Resonance Technique The binding affinity of the mouse antibody to human GPC-1 was measured through surface plasmon resonance technique (Biacore (registered trademark) 8K). An anti-mouse-Fc antibody was immobilized on a chip, and the mouse antibody (01a033) was flowed thereon and allowed to bind thereto. After washing, the human GPC-1 was flowed thereon, and the binding constant (Ka) and the dissociation constant (Kd) were measured.

Production of Mouse Anti-GPC-1 Chimeric Antibody

A human antibody chimeric gene was produced by linking the VH/VL gene of 01a033 to the human Ck/CH gene. This chimeric gene was expressed in HEK293F cells.

Example 1: Analysis of Affinity of Humanized Anti-GPC1 Monoclonal Antibody

Materials and Methods

The mouse anti-human-GPC1 monoclonal antibody was humanized (subclass: IgG4), and the obtained twenty clones (T1, T2, T3, T7, T8, T10, T11, T22, T26, T28, T29, T31, T32, T33, T34, T36, T43, T56, T57, T59) were prepared. An anti-human IgG (Fc) was immobilized on an sCM5 sensor chip (GE Healthcare) using Human antibody capture kit (GE Healthcare), and the affinity of each of these clones to a recombinant human GPC1 protein (R&D Systems) was measured using Biacore (registered trademark) 8K (GE Healthcare).

Results

The anti-Glypican-1 (GPC-1) monoclonal antibody (01a033) was independently humanized, and as a result, twenty candidate clones were obtained. The equilibrium dissociation constant ($K_D$) of each of these twenty clones was measured using Biacore (registered trademark) (FIG. 1). As a result, it was found that seven clones (clones T1, T2, T3, T8, T10, T36, T56) had affinity higher than that of the chimeric mouse antibody (01a033), which was not subjected to the humanization yet (FIG. 1).

Example 2: ADC Assay Using Humanized Anti-GPC-1 Antibody and MMAF-Bound

Secondary Antibody in Combination
Materials and Methods

Verification of Sensitivity of TE14 Cell to Anti-Cancer Agent

80 µl of a solution containing 2,000 TE14 cells was added to a 96-well plate. The cells were cultured overnight in an incubator at 37° C. and 5% $CO_2$. On the next day, 10 µl of a solution containing each humanized anti-GPCT antibody clone at a concentration of 10 times as high as the final concentration thereof was added per well as a primary antibody. Subsequently, 10 µl of a solution containing an anti-human-IgG antibody (Fab) to which an anti-cancer agent (MMAF) was linked via a linker (MORADEC, Catalog No. AH-202AF-50) was added per well as a secondary antibody to a final volume of 100 µl. The cells were cultured for 6 days in an incubator at 37° C. and 5% CO2, and the cell viability was measured by detecting the ATP amount using a Cell Titer-Glo Luminescent Cell Viability Assay reagent. RPMI1640 supplemented with 10% FBS and 1% PS was used as the culture medium.

ADC Used in Assay

FIG. 2 shows a schematic diagram illustrating an ADC used in the assay. Clones having high cell-internalization activity were screened from the twenty clones in accordance with the method shown in FIG. 2. In this procedure, an assay system was used in which the humanized anti-GPC1 antibody derived from the clone obtained in the Production Example above was added as a primary antibody to the TE14 cell line, which is an esophageal cancer cell line that expresses GPC1, an anti-cancer agent (MMAF) conjugated anti-human-IgG antibody was added as a secondary antibody thereto, and thus the anti-cancer agent was taken in by the cancer cells as a complex of the primary antibody and the secondary antibody, thereby inducing cell death due to the effects of the anti-cancer agent.

Results

Figure 3:
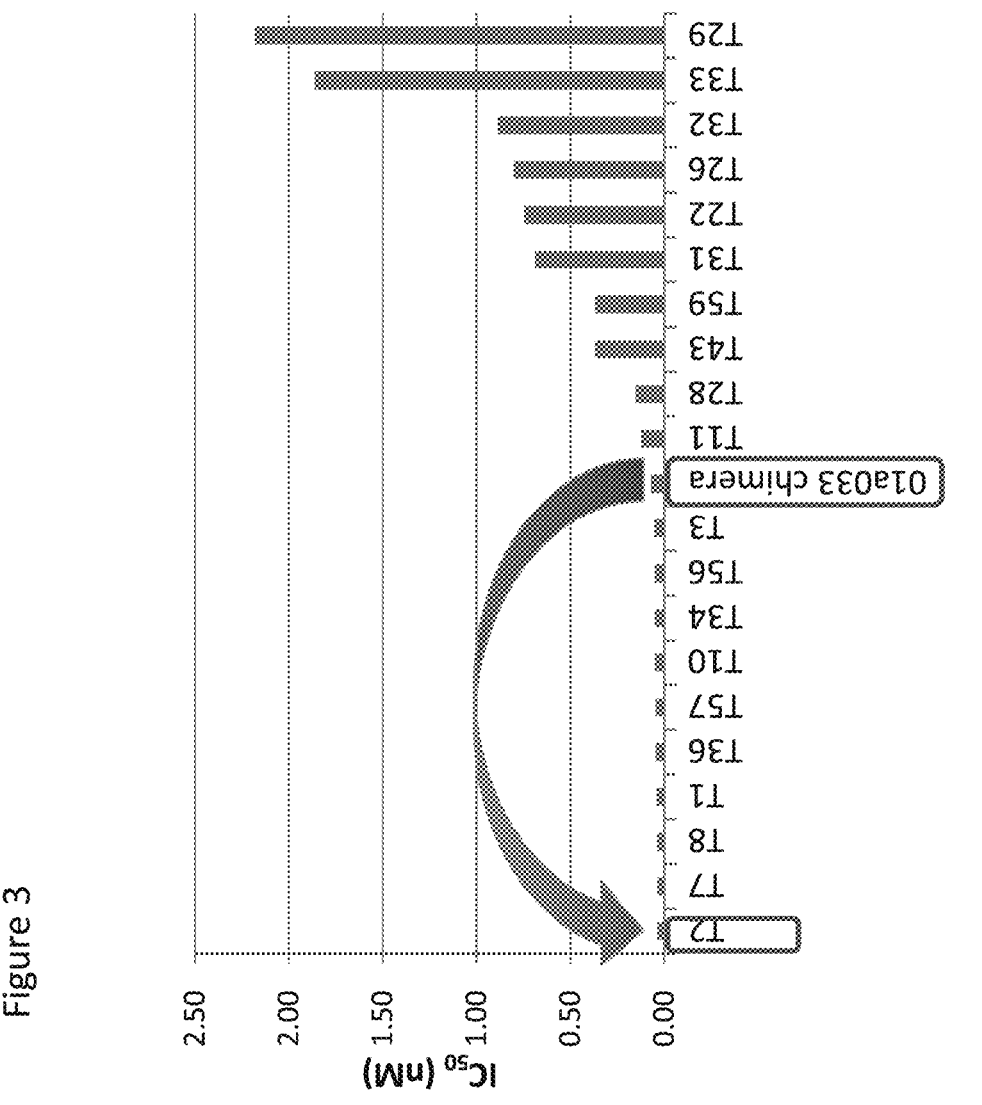
FIG. 3 shows the results of cytotoxic activity ($IC_{50}$) of twenty types of clones against the TE14 cell line.

It was found that ten clones (clones T2, T7, T8, T1, T36, T57, T10, T34, T56, T3) had cell-internalization activity higher than that of the chimeric mouse antibody (01a033) (FIG. 3).

Example 3: Antigen Affinity Analysis Using FACS

Since it was found from the results of Example 2 that the clone T2 had the highest activity, the clone T2 was selected as a humanized anti-GPC1 antibody having high cell-internalization activity, and was subjected to analysis.

Materials and Methods

In the FACS analysis using the antibody, cells of human esophageal cancer cell line (TE8) were used as GPC1-positive cells, and TE8-GPC1 KO cells in which GPC1 was knocked out using a CRISPR-Cas9 technique were used as GPC1-negative cells. The measurement was performed with FACS CantoII (BD) using the human/mouse chimeric anti-GPC1 antibody (clone 01a033) and the humanized anti-GPC1 antibody (clone T2) as primary antibodies and FITC labeled anti-human-IgG-FITC (Jackson Immuno Research, Catalog No. 109-095-098) as a secondary antibody, and the measurement data were analyzed using BD FACS Diva Software (BD).

Materials and Methods

The measurement was performed with FACS CantoII (BD) using the human/mouse chimeric anti-GPC1 antibody (clone 01a033) and the humanized anti-GPC1 antibody (clone T2) as primary antibodies at various concentrations and FITC labeled anti-human-IgG-FITC (Jackson Immuno Research, Catalog No. 109-095-098) as a secondary antibody, and the measurement data were analyzed using BD FACS Diva Software (BD).

Results

Figure 4:
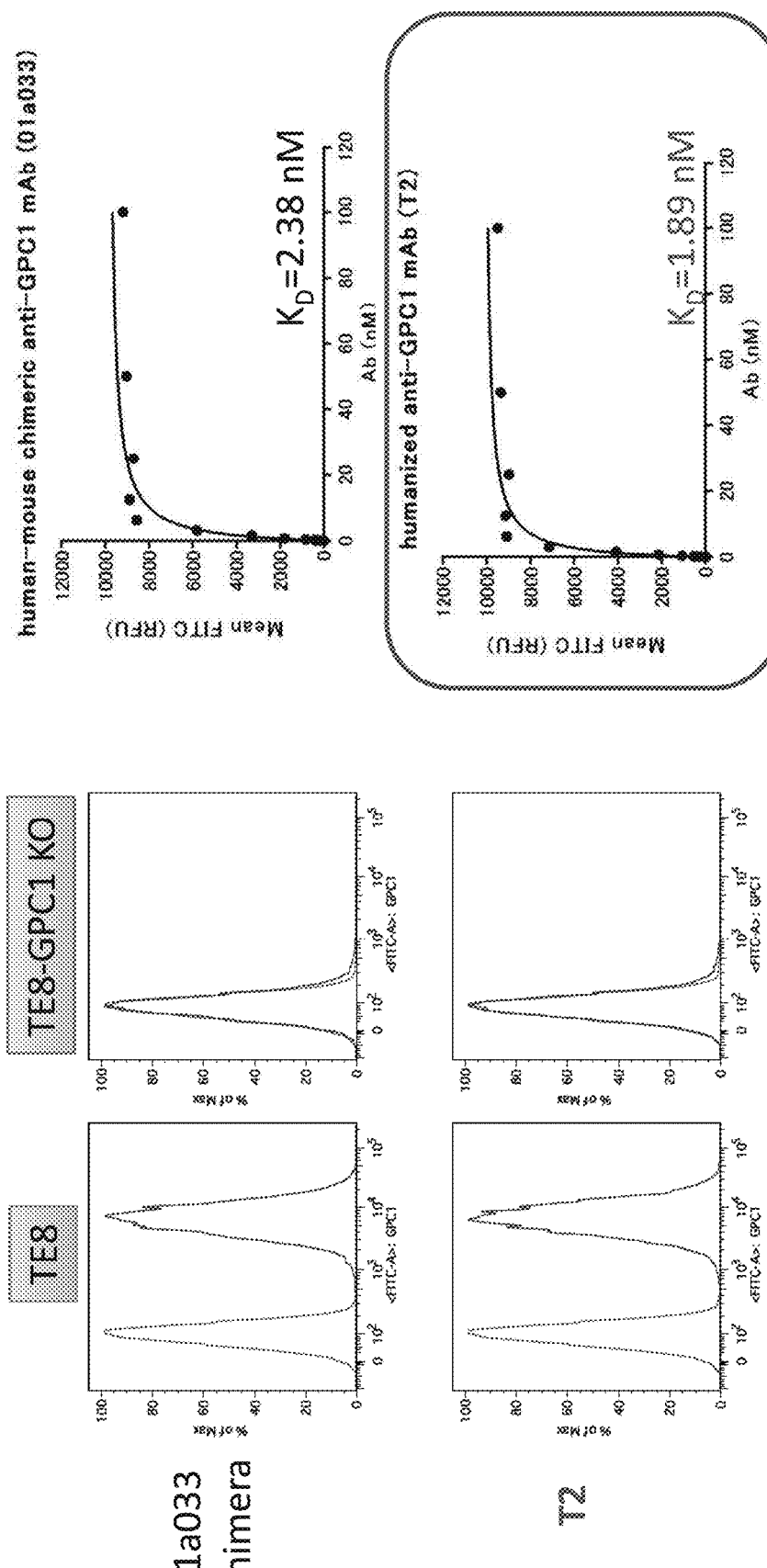
FIG. 4 shows the results of an antigen affinity analysis of an anti-GPC-1 chimeric antibody (01a033) and a clone T2 measured using a FACS.

As a result of performing, on the TE8, which is GPC1-positive esophageal cancer cell line, and the TE8-GPC1-KO cells in which GPC1 was knocked out using the CRISPR/Cas9 system, the FACS analysis using the chimeric mouse antibody (01a033) and the humanized anti-GPC1 antibody (T2), the humanized anti-GPC1 antibody (T2) had no reactivity with the TE8-GPC1-KO cells but had reactivity with only the TE8 cells, and it was thus found that the humanized anti-GPC1 antibody (T2) had GPC1-specific binding ability (FIG. 4). Regarding the reactivity with GPC1 on the surface of the TE8 cell as well, it was revealed that the humanized anti-GPC1 antibody (T2) had affinity higher than that of the chimeric mouse antibody (01a033) (FIG. 4).

Example 4: Production of ADC

In this example, an ADC was produced as follows.

The mAb humanized anti-GPC1 antibody (clone T2) was conjugated with maleimidecaproyl-valine-citrulline-p-aminobenzyloxycarbonyl-monomethyl auristatin E (MC-vc-PAB-MMAE). The conjugate was formed using a maleimide-cysteine-based method in which the disulfide bonds between the chains of the mAb is reduced using TCEP at 37° C. first, and then the maleimide moiety of the drug is linked to the reduced cysteine. The ADC was desalted using Amicon Ultra—0.5 mL Centrifugal filters—30K (Millipore), and unreacted toxins were removed. Then, the buffer was exchanged with an ADC formulation buffer (20 mM histidine, 7% sucrose, 0.02% (w/v) PS80, pH 5.5). The distribution of the drug-antibody ratio (DAR) was analyzed through hydrophobic interaction chromatography (HIC), and the degree of coagulation was analyzed through size exclusion chromatography (SEC). The conjugating conditions were set such that the drug-antibody ratio (DAR) was 4.

Results

Figure 5:
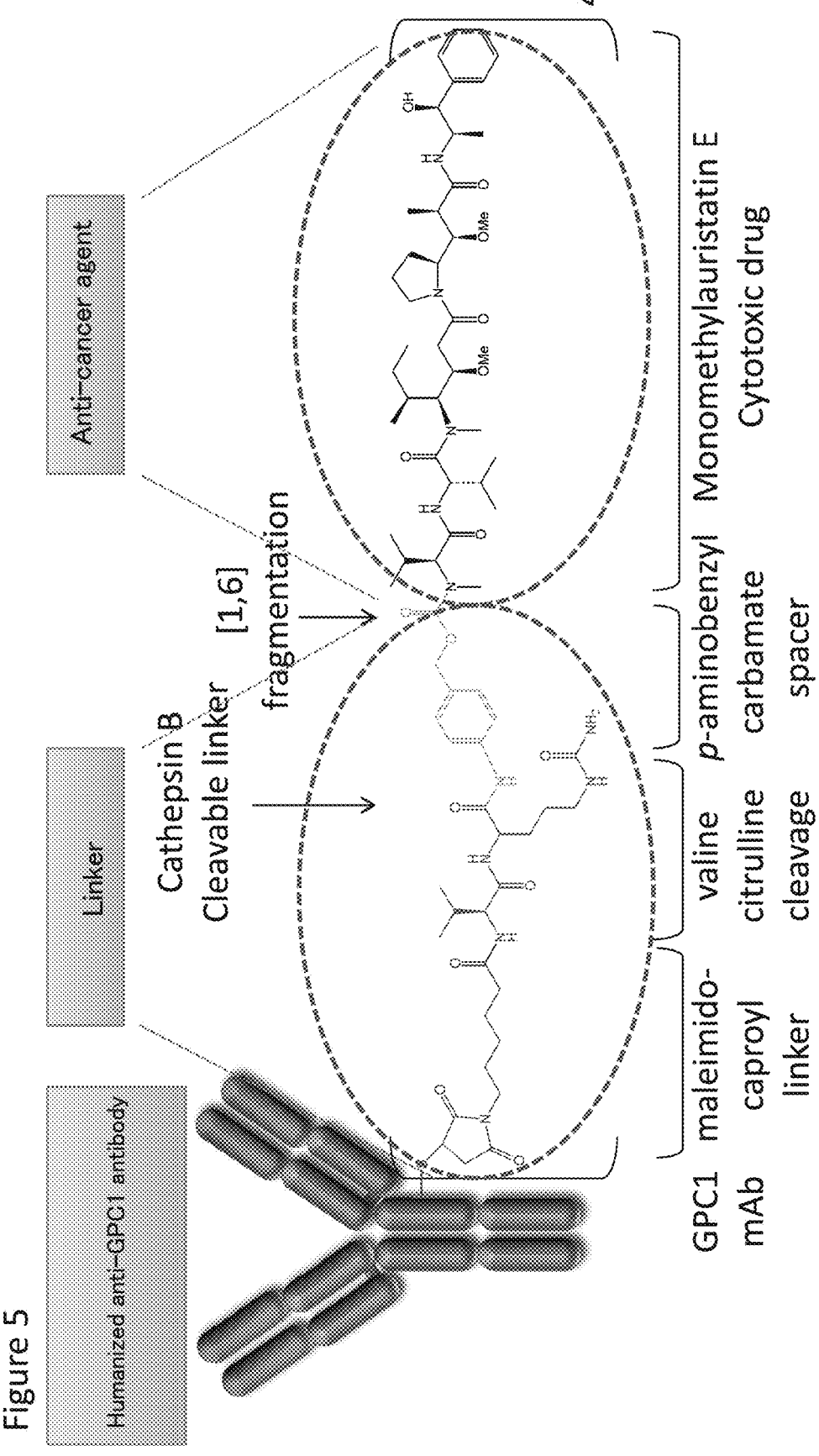
FIG. 5 shows a schematic diagram illustrating the structure of an exemplary ADC.
Figure 6:
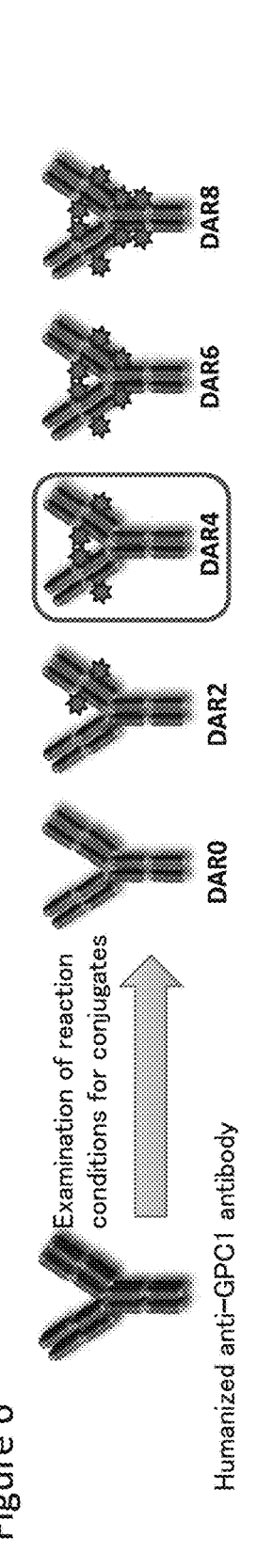
FIG. 6 shows a schematic diagram illustrating the settings of a drug-to-antibody ratio (DAR).

FIG. 5 shows a schematic diagram illustrating the structure of an exemplary ADC. As shown in FIG. 5, MMAE, which is a payload having a bystander effect, was conjugated with a cysteine residue of the humanized anti-GPC1 antibody (clone T2) via a cleavable linker capable of being cleaved by cathepsin B. The humanized GPC1-ADC had a DAR of 4.0 (FIG. 6).

Example 5: Antigen Affinity Analysis with FACS Using Humanized GPC1-ADC and Unlabeled Antibody Materials and Methods In the FACS analysis using the antibody, cells of human pancreatic cancer cell line (BxPC-3) were used as GPC1-positive cells. The measurement was performed with FACS CantoII (BD) using the humanized anti-GPC1 antibody (clone T2) and the humanized GPC1-ADC (MMAE) as primary antibodies at various concentrations and FITC labeled anti-human-IgG-FITC (Jackson Immuno Research, Catalog No. 109-095-098) as a secondary antibody, and the measurement data were analyzed using BD FACS Diva Software (BD).

Results

Figure 7:
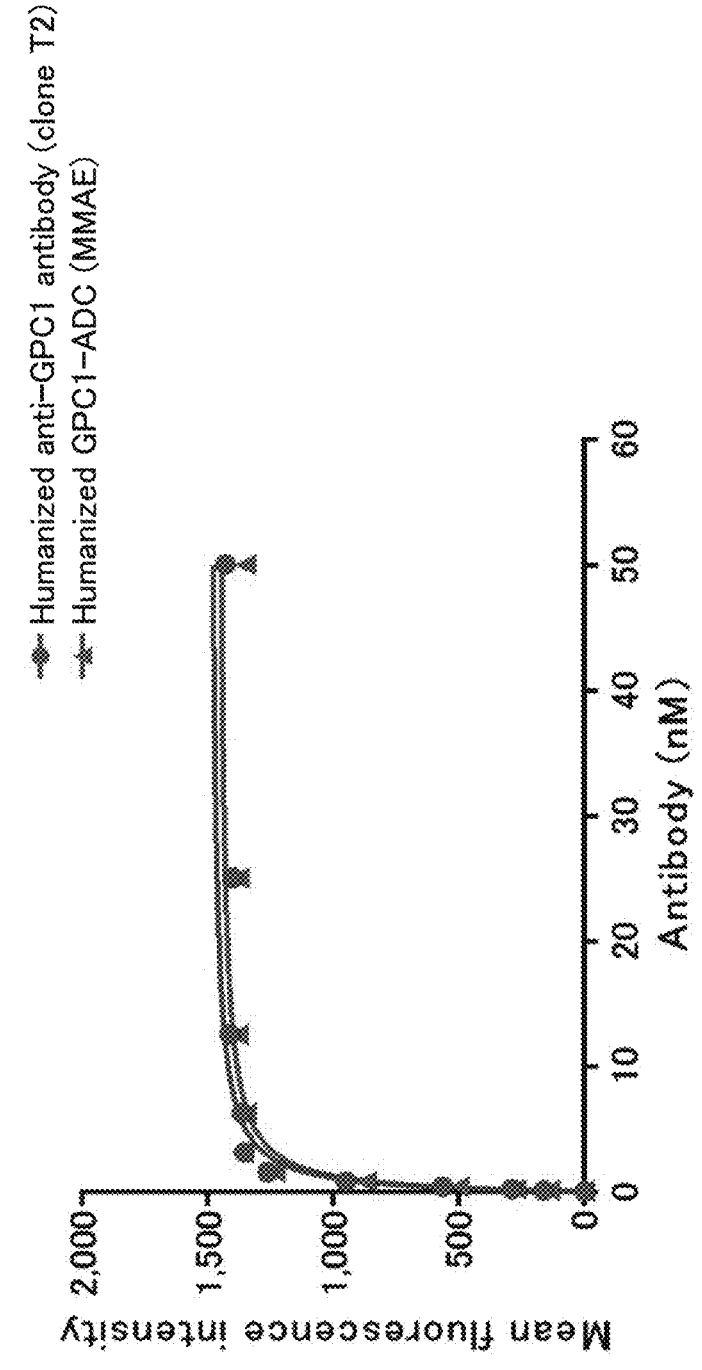
FIG. 7 shows the results of an antigen affinity analysis of a humanized GPC1-ADC and an unlabeled antibody using a FACS.

The influence of conjugation of a payload with the humanized anti-GPC1 antibody (T2) on the antigen affinity was evaluated by analyzing the antibody concentration-dependent binding ability with FACS using GPC1 expression-positive BxPC3 cells. As a result, the $K_D$ value of the humanized anti-GPC1-ADC was the same as that of the humanized anti-GPC1 antibody (T2), and it was thus found that the conjugation of the payload did not significantly reduce the antigen affinity (FIG. 7).

Example 6: Cell-Internalization Assay of Humanized Anti-GPC-1 Antibody (Clone T2) and Humanized GPC1-ADC (MMAE)

In this example, the internalization (cell entry) activity of the humanized GPC1-ADC (MMAE) was investigated with a FACS using the GPC1-positive BxPC-3 cell line.

Materials and Methods

The cells treated with the humanized anti-GPC1 antibody (clone T2) and the humanized GPC1-ADC (MMAE) were detected using an anti-GPC1 mAB (biotin-labeled 02b006) and a PE-labeled streptavidin.

The BxPC-3 cell line was removed from a 10-cm plate using 0.02% EDTA and collected. The cells were suspended in RPMI1640 supplemented with 10% FBS, 1% GlutaMAX (trademark) I, 100 U/ml penicillin, and 100 μg/ml streptomycin such that 0.9 ml of the suspension containing $2.0 \times 10^6$ cells was obtained in a 1.5-ml tube. The suspension was allowed to stand on ice for 1 hour to reduce the internalization activity. A 1 mg/ml solution of the humanized anti-GPC1 antibody (clone T2) and a 1 mg/ml solution of the humanized GPC1-ADC (MMAE) were diluted using ice-cooled RPMI 1640 supplemented with 10% FBS, 1% GlutaMAX (trademark) I, 100 U/ml penicillin, and 100 μg/ml streptomycin to a final concentration of 24 μg/ml (160 nM). 100 μl of each antibody solution was added to the cell suspension and suspended and was allowed to stand on ice for 30 minutes to stain the antigen on the cell surface. After 30 minutes, the cell suspension was dispensed into six 100-μl aliquots. The cell suspension was divided into a 4° C.-incubation group and a 37° C.-incubation group, and thus 12 aliquots in total were prepared. The incubation time was set to 0 h, 1 h, 2 h, 3 h, 4 h, and 6 h. After the end of the incubation time, the cells were centrifuged at 1,500 rpm at 4° C. for 5 minutes, and the supernatant was removed. The cells were washed using 100 μl of ice-cooled PBS supplemented with 0.2% BSA, then centrifuged, and then washed. The washing operation was performed 3 times in total. 50 μL of a 1 μg/ml solution of a biotin-labeled anti-GPC1 antibody 02b006 (WO 2018/199318) was added and suspended. The antigen on the cell surface was stained for 30 minutes on ice (GPC1 that had not been internalized was stained). After the end of the incubation time, the cells were centrifuged at 1,500 rpm at 4° C. for 5 minutes, and the supernatant was removed. The cells were washed using 100 μl of ice-cooled PBS supplemented with 0.2% BSA, then centrifuged, and then washed. The washing operation was performed 3 times in total. Streptavidin-PE (PharMingen, #554061) was diluted 200-fold using ice-cooled PBS supplemented with 0.2% BSA, and 50 μL of the diluted solution was added to the cells and suspended. The reaction was allowed to progress on ice for 30 minutes in a dark place. After the end of the incubation time, the cells were centrifuged at 1,500 rpm at 4° C. for 5 minutes, and the supernatant was removed. The cells were washed using 100 μl of ice-cooled PBS supplemented with 0.2% BSA, then centrifuged, and then washed. The washing operation was performed 3 times in total. 150 μL of ice-cooled PBS supplemented with 0.2% BSA was added. Then the measurement was performed with FACS CantoII, and the analysis was performed using BD FACS Diva Software (BD).

Furthermore, when the humanized anti-GPC1 antibody (clone T2) and the humanized GPC1-ADC (MMAE) were internalized using the GPC1-positive BxPC-3 cell line, the localization of the humanized anti-GPC1 antibody (clone T2) and the humanized GPC1-ADC (MMAE) inside the cell was investigated using a fluorescence microscope.

7.5×10$^4$ BxPC-3 cells (1 ml/well) were seeded per well of a 12-well plate (Corning: 3513) in which an 18-mm micro-cover glass (Matsunami) was placed, and the cells were cultured overnight in an incubator at 37° C. and 5% $CO_2$.

On the next day, the culture medium was removed, 1.0 ml of ice-cooled RPMI1640 supplemented with 10% FBS, 1% GlutaMAX (trademark) I, 100 U/ml penicillin, and 100 µg/ml streptomycin was added to the well, and the cells were incubated at 4° C. for 1 hour to reduce the internalization activity of the cells.

Subsequently, the culture medium in the well was removed, 500 µl of a 10 µg/ml solution of the primary antibodies (ice-cooled solution of the humanized anti-GPC1 antibody (clone T2) and the humanized GPC1-ADC (MMAE)) was added per well, and the cells were incubated at 4° C. for 15 minutes.

After 15 minutes, the antibody solution was aspirated, 1.0 ml of ice-cooled RPMI1640 supplemented with 10% FBS, 1% GlutaMAX (trademark) I, 100 U/ml penicillin, and 100 µg/ml streptomycin was added, and the cells were washed. The sample at this time point was collected as a 0-hour sample (0 h).

As for the sample to be internalized, the solution was aspirated, 1.0 ml of RPMI1640 supplemented with 10% FBS, 1% GlutaMAX (trademark) I, 100 U/ml penicillin, and 100 µg/ml streptomycin (warmed at 37° C.) was added, and the cells were cultured for 4 hours in an incubator at 37° C. and 5% $CO_2$. The sample at this time point was collected as a 4-hour sample (4 h).

As for the samples at the time points after 0 hour and 4 hours, the culture medium inside the well was removed, and the cells were washed using 1 ml of ice-cooled PBS.

Next, 1 ml of 100% (ice-cooled) methanol was added, the cells were incubated at −20° C. for 15 minutes and were thus fixed. After fixed, the cells were washed three times using 1 ml of PBS. Then, 1 ml of 1% BSA, 0.3% Triton X-100/ PBS(−) was added, and blocking treatment was performed at room temperature for 1 hour. After the blocking treatment, the solution was removed, 0.5 ml of solution of a primary antibody (anti-CD107a monoclonal antibody (CST, Catalog No. #9091, LAMP1(D2D11)XP (registered trademark) Rab-bit mAb)) diluted 100-fold using 1% BSA, 0.3% Triton X-100/PBS(−) was added per well, and then the reaction was allowed to progress at 4° C. overnight in a dark place.

After the primary antibody reaction was performed over-night, the cells were washed three times using 1 ml of PBS.

Then, 0.5 ml of a solution of a cross-adsorbed secondary antibody goat anti-human IgG(H+L)-Alexa Fluor 488 (Life Technology, A-11013, Lot. 2110842) diluted 200-fold using 0.3% Triton X-100/PBS(−) supplemented with 1% BSA and 0.5 ml of a solution of a donkey anti-rabbit IgG-Alexa 647 (Life Technology, A31573, Lot. 1626613) diluted 200-fold were added per well, and the reaction was allowed to progress at room temperature for 1 hour in a dark place.

After the secondary antibody reaction, the cells were washed three times using 1 ml of PBS, the cover glass to which the cells adhered was removed and was mounted in Vectashield (Vectashield H1200) on a glass slide. Then, the cells were observed under an all-in-one fluorescence micro-scope (KEYENCE, BZ-X800).

Results

Figure 8:
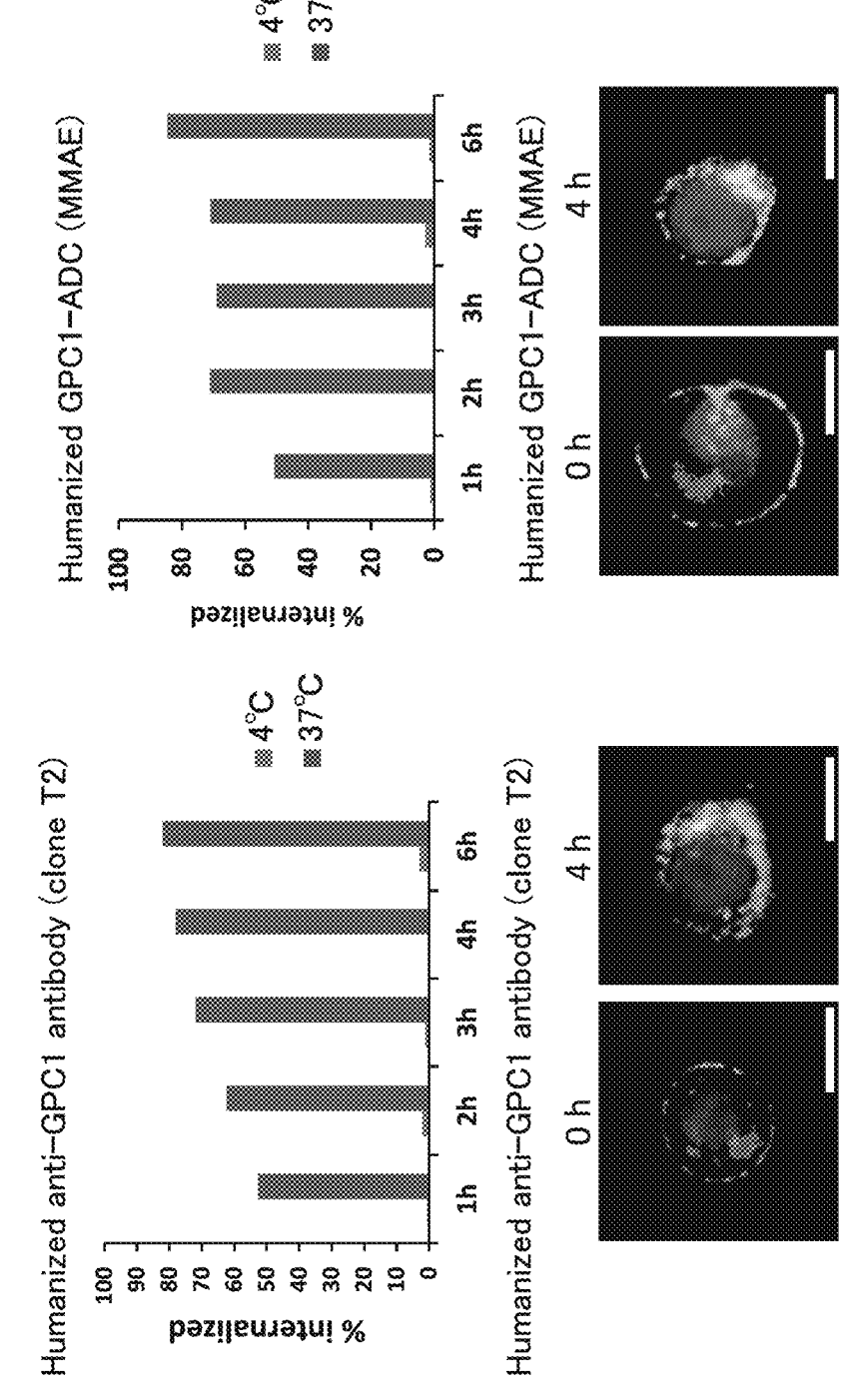
FIG. 8 shows the results of a cell-internalization assay of a humanized anti-GPC-1 antibody (clone T2) and a humanized GPC1-ADC (MMAE). Green indicates GPC1 staining, red indicates CD107a staining, and blue indicates DAPI staining. The scale bar indicates 10 μm. In each group shown in the graphs, the left bar indicates the result obtained at 4° C., and the right bar indicates the result obtained at 37° C.

The cell-internalization activity was evaluated. It was found from the results of the FACS analysis using the BxPC3 cells that, in both cases of adding the humanized anti-GPC1 antibody (T2) to the BxPC3 cells and adding the humanized anti-GPC1-ADC thereto, 60% to 70% or more of GPC1 was rapidly internalized into the cells within 2 hours after the addition thereof (FIG. 8). In order to cause this ADC to exhibit an anti-tumor effect, the linker moiety of the ADC need to be cleaved by the enzyme cathepsin B in the lysosome. Therefore, the intracellular localization was evaluated by determining the locations of a lysosome marker CD107a and the GPC1 through fluorescence double stain-ing. As a result, both the humanized anti-GPC1 antibody (T2) and the humanized anti-GPC1-ADC colocalized with the CD107a, and it was thus found that the humanized anti-GPC1 antibody (T2) and the humanized anti-GPC1-ADC bound to GPC1 and then moved to a lysosome (FIG. 8).

Example 7: In-Vitro ADC Assay Using Humanized GPC1-ADC (MMAE)

Materials and Methods

A GPC1 expression analysis was performed using a FACS.

To analyze GPC1 expression, a FACS analysis was per-formed on the following types of cells: cells of esophageal cancer cell lines (TE8, TE14); cells of pancreatic cancer cell lines (BxPC3, KP-2, PK-8); TE8-GPC1 KO, TE14-GPC1 KO cells, and BxPC3-GPC1 KO cells in which GPC1 was knocked out using a CRISPR-Cas9 technique; cells of a cervical cancer cell line (HeLa); cells of head and neck tumor cell lines (Detroit562, FaDu); and cells of oral squa-mous cell cancer cell lines (Ho-1-u-1, KOSC2 cl3-43, KON). The measurement was performed with FACS CantoII (BD) using the mouse anti-GPC1 antibody (clone 01a033) as a primary antibody and an FITC labeled goat anti-mouse-IgG (H+L chain specific) (Southern Biotech) as a secondary antibody, and the measurement data were analyzed using FlowJo (trademark) Software (Tree Star).

The in-vitro ADC assay using the humanized GPC1-ADC (MMAE) produced in Example 4 was performed as follows.

(1) The cells were seeded on a 96-well white plate (Catalog No. 136101) manufactured by Thermo Fisher Sci-entific (90 µL of a cell suspension). RPMI1640 supple-mented with 10% FBS, 100 U/ml penicillin, and 100 µg/ml streptomycin was used as the culture medium (RPMI1640 supplemented with 10% FBS, 1% GlutaMAX (trademark) I, 100 U/ml penicillin, and 100 µg/ml streptomycin was used for the BxPC-3 cells, DMEM supplemented with 10% FBS, 100 U/ml penicillin, and 100 µg/ml streptomycin was used for Detroit562, FaDu, and KON, and DMEM/F12 supple-mented with 10% FBS, 100 U/ml penicillin, and 100 µg/ml streptomycin was used for Ho-1-u-1). The cells were seeded in 60 wells in the middle of the plate, and 100 µL of the culture medium was added to 36 wells located along the outer periphery. The cells were cultured in an incubator at 37° C. and 5% $CO_2$.

(2) On the next day, 10 µL of the ADC solution was added to the cells (total amount: 100 µL).

(3) After the cells were cultured for 144 hours, 100 µL of CellTiter-Glo (registered trademark) Luminescence Cell Viability Assay Reagent (Promega) was added per well.

(4) The measurement was performed using a plate reader.

(5) The analysis was performed using GraphPad Prism 6. The IC50 value was calculated using the equation below (Hossain M M, Hosono-Fukao T, Tang R, Sugaya N, van Kuppevelt T H, Jenniskens G J, Kimata K, Rosen S D, Uchimura K (2010) Direct detection of HSulf-1 and HSulf-2 activities on extracellular heparan sulphate and their inhibition by PI-88, Glycobiology 20(2): 175-186).

$$IC50=10^{\wedge}(\text{Log}[A][B]\times(50C)/(DC)+\text{Log}[B])$$

Figure 9:
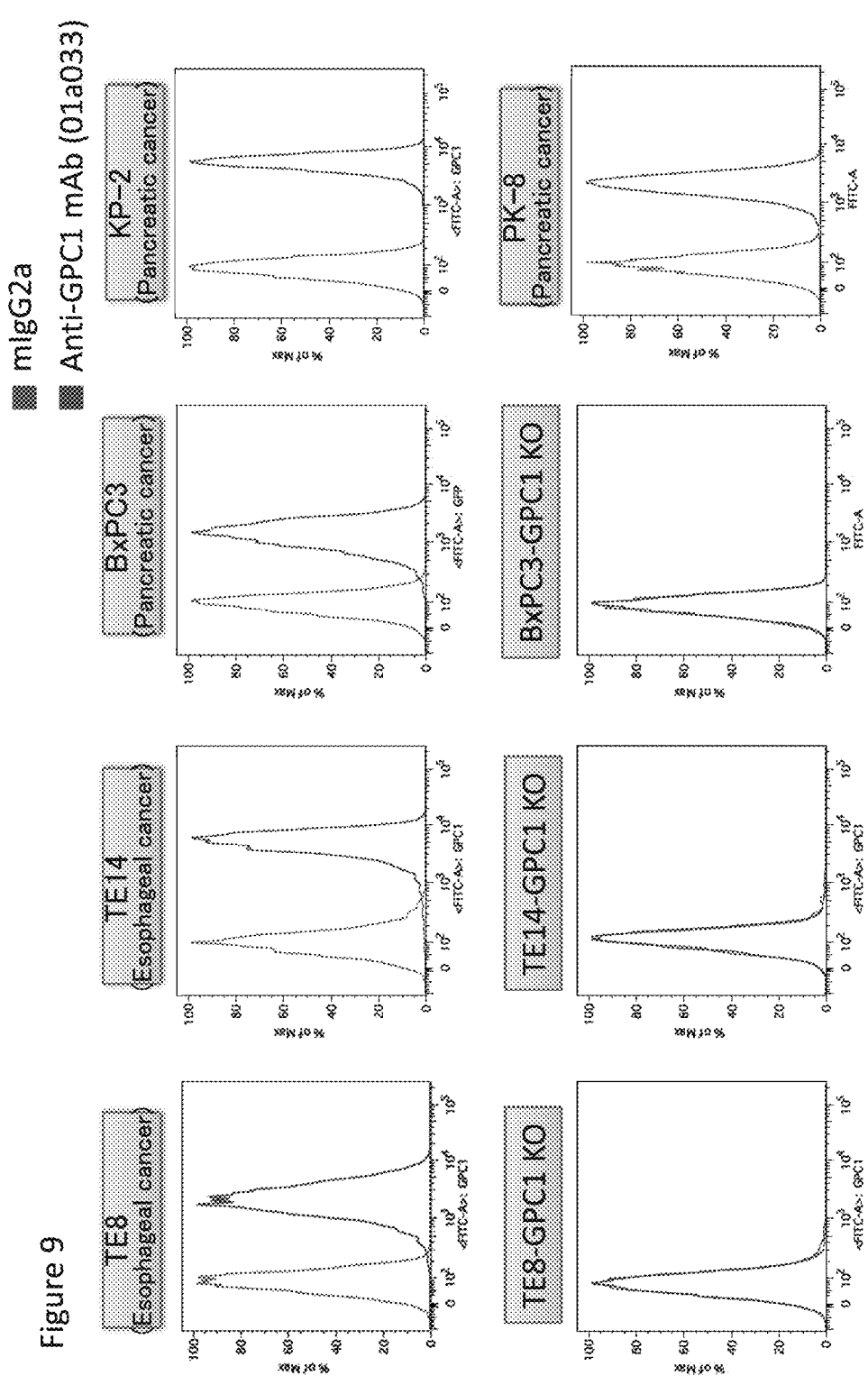
FIG. 9 shows the results of a GPC1-expression analysis of various cell lines measured using a FACS.
Figure 10:
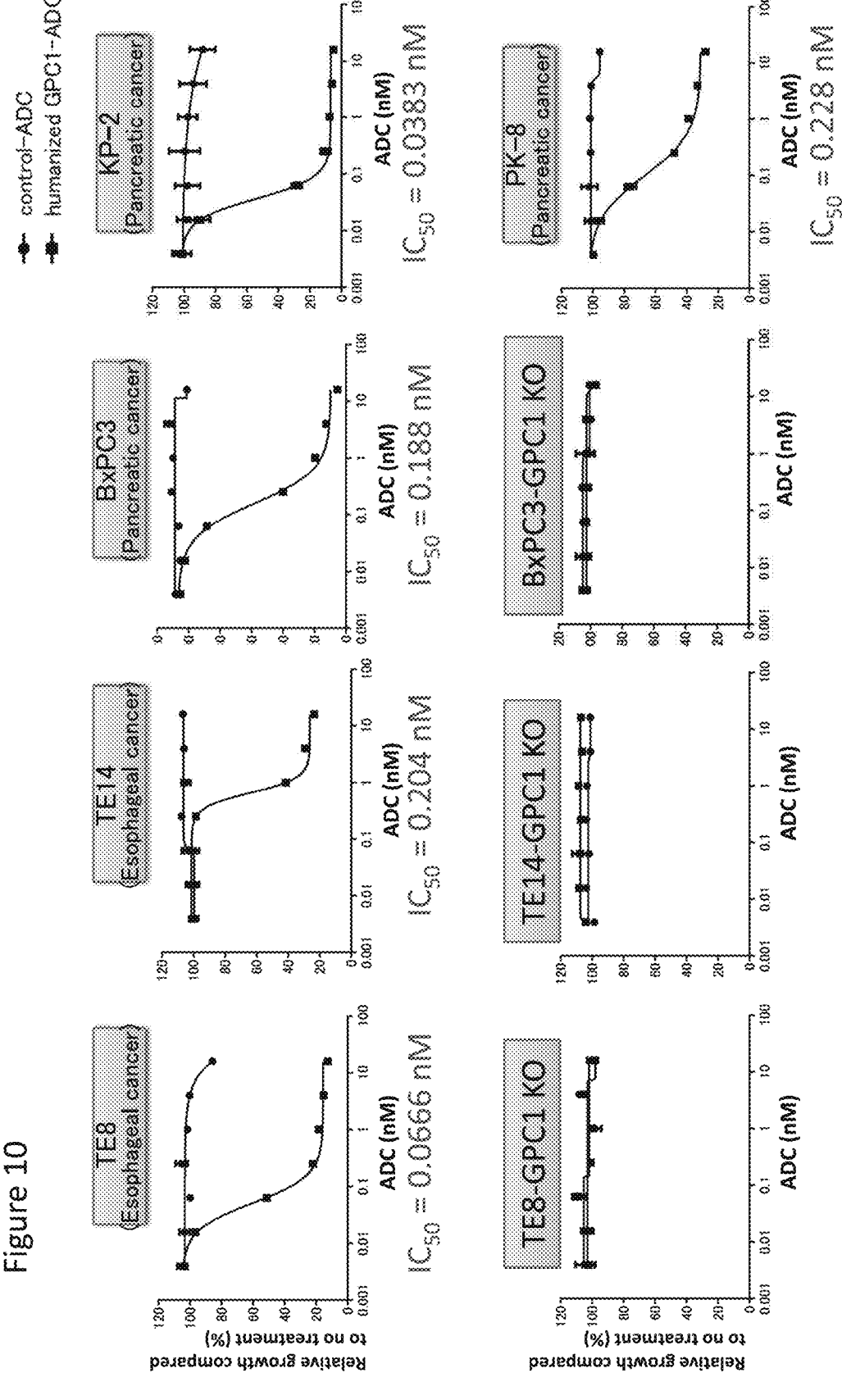
FIG. 10 shows the results of an in-vitro ADC assay using a humanized GPC1-ADC (MMAE).
Figure 11:
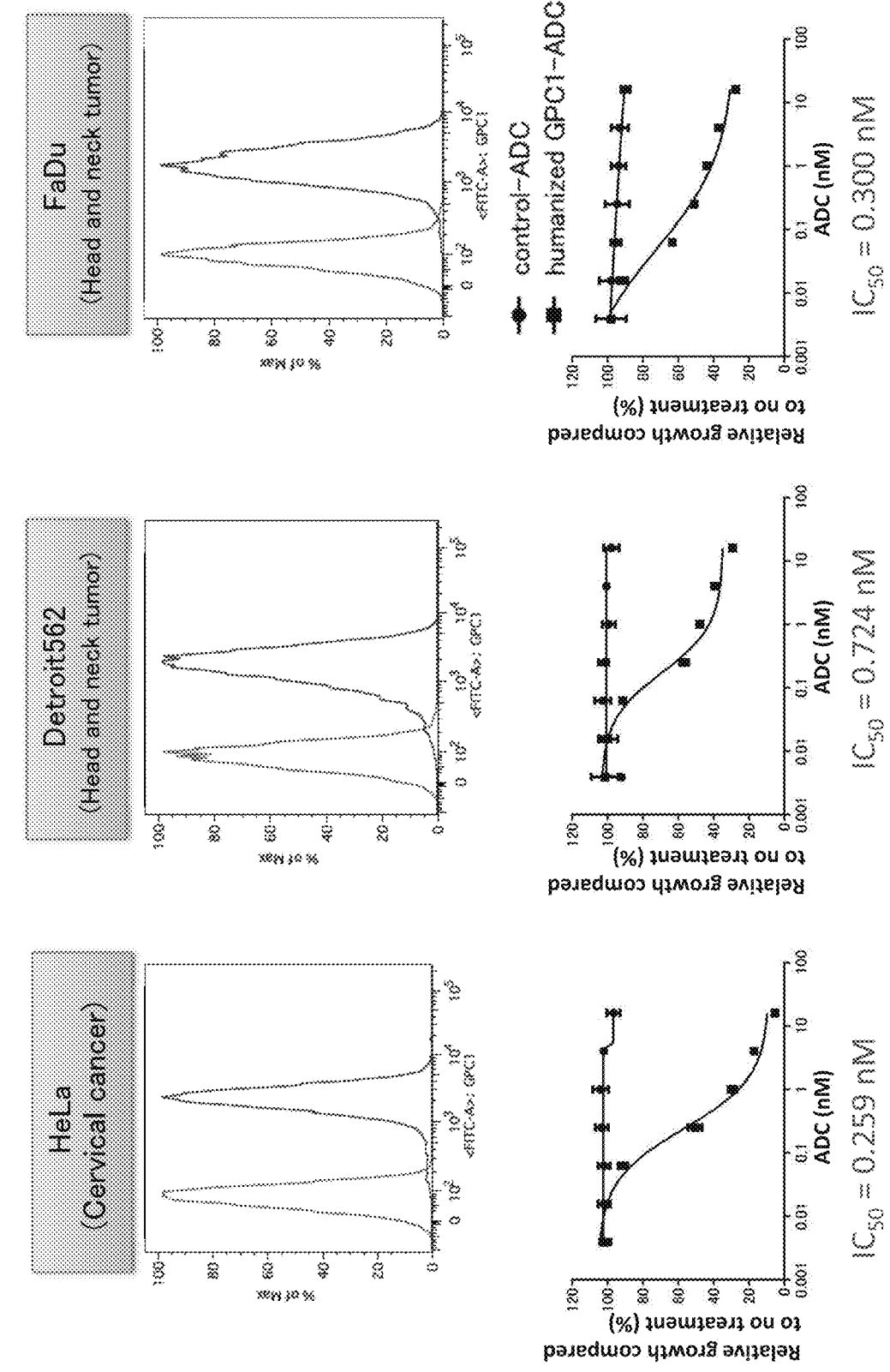
FIG. 11 shows the results of a GPC1 expression analysis and an ADC assay of a HeLa cell line, a Detroit562 cell line, and a FaDu cell line.
Figure 12:
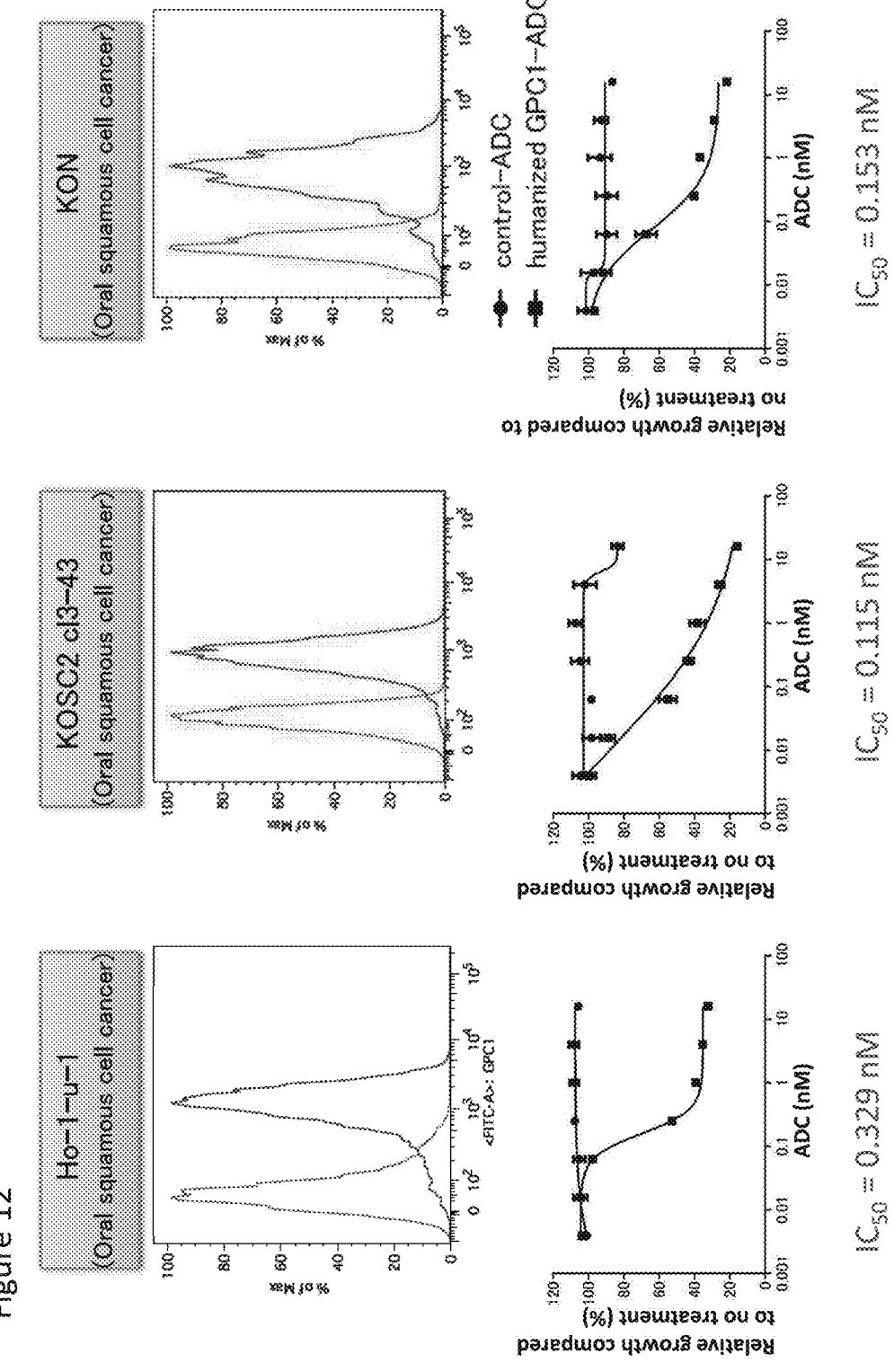
FIG. 12 shows the results of a GPC1 expression analysis and an ADC assay of a Ho-1-u-1 cell line, a KOSC2 cl3-43 cell line, and a KON cell line.

A: Concentration higher than 50%
B: Concentration lower than 50%
C: Inhibition rate at B
D: Inhibition rate at A Results In order to evaluate the efficacy of the produced humanized GPC1-ADC, a GPC1-expression-positive cell line and a GPC1-expression-negative cell line were prepared. The GPC1-positive esophageal cancer cell lines TE8 and TE14, and the GPC1-positive pancreatic cancer cell line BxPC3 were used to produce the TE8-GPC1-KO cells, the TE14-GPC1-KO cells, and the BxPC3-GPC1-KO cells in which GPC1 was knocked out using a CRISPR-Cas9 system, and the FACS analysis was performed to confirm if GPC1 was knocked out (FIG. 9). As a result of performing the in-vitro ADC assay, the humanized GPC1-ADC had efficacy in the GPC1-positive cancer cell lines, but did not have efficacy in the GPC1-negative cancer cell lines. Therefore, it was found that the humanized GPC1-ADC had efficacy in a GPC1-expression-dependent manner (FIG. 10). It was found that the humanized GPC1-ADC also had efficacy in the cervical cancer cell line, the head and neck tumor cell lines, and the oral squamous cell cancer cell lines in a GPC1-expression-dependent manner (FIGS. 11 and 12) in addition to the pancreatic cancer cell line and the esophageal cancer cell lines.

Example 9: In-Vivo Efficacy Test of Humanized GPC1-ADC (MMAE) Using Pancreatic Cancer PDX (PK565)

Materials and Methods

The GPC1 expression in pancreatic cancer PDX (PK565) was confirmed as follows.

Sections of a paraffin embedded tissue were subjected to deparaffinization, and were then dehydrated using alcohol. Immunohistochemical staining of GPC1 was performed using an anti-GPC-1 antibody (Genetex: GTX104557) and ChemMate Envision Kit HRP 500T (Dako: K5007). It was found that the PK565 was a heterogeneous tumor in which GPC1-expression positive pancreatic cancer cells and GPC1-expression negative pancreatic cancer cells coexisted.

The pancreatic cancer PDX was subcutaneously implanted into 6-week-old female NOG mice. When the size of the implanted tumor reached about 100 mm³, administration of PBS, a control ADC (10 mg/kg), and the humanized anti-GPC1-ADC (MMAE) produced in Example 4 (1 mg/kg, 3 mg/kg, 10 mg/kg) was started. The day on which the administration was started was taken as day 0, and intravenous administration was performed on day 0, day 7, day 14, and day 21. The tumor volume and the body weight were measured from day 0 to day 42 at a frequency of twice a week.

Results

As a result of intravenously administering the medicine weekly, four times in total, in the in-vivo efficacy test, the humanized GPC1-ADC also had a high anti-tumor effect on the GPC1-positive pancreatic cancer PDX mice (PK565) in a concentration-dependent manner (FIG. 13). At this time, a reduction in the body weight was not observed, which shows that the GPC1-ADC had no characteristic toxicity unlike the control ADC. Compared with the systemic administration of an anti-cancer agent, higher efficacy and lower toxicity are achieved by delivering an anti-cancer agent specifically to GPC1-positive cancer cells using the GPC1-ADC in vivo, which leads to development of a revolutionary therapeutic reagent for GPC1-positive cancer.

Example 10: In-Vivo Efficacy Test of Humanized GPC1-ADC (MMAE) Using Pancreatic Cancer PDX (PK175)

Materials and Methods

The GPC1 expression in pancreatic cancer PDX (PK175) was confirmed as follows.

Sections of a paraffin embedded tissue were subjected to deparaffinization, and was then dehydrated using alcohol. Immunohistochemical staining of GPC1 was performed using an anti-GPC-1 antibody (Genetex: GTX104557) and ChemMate Envision Kit HRP 500T (Dako: K5007). It was found that the PK175 was a tumor in which GPC1-expression was positive in both the pancreatic cancer cells and the cancer-associated fibroblasts (CAFs).

The pancreatic cancer PDX was subcutaneously implanted into 6-week-old female NOG mice. When the size of the implanted tumor reached about 100 mm³, administration of PBS and the humanized anti-GPCT-ADC (MMAE) (1 mg/kg, 3 mg/kg, 10 mg/kg) was started. The day on which the administration was started was taken as day 0, and intravenous administration was performed on day 0, day 7, day 14, and day 21. The tumor volume and the body weight were measured from day 0 to day 42 at a frequency of twice a week.

Results

As a result of intravenously administering the medicine weekly, four times in total, in the in-vivo efficacy test, the humanized GPC1-ADC also had a high anti-tumor effect on the GPC1-positive pancreatic cancer PDX mice (PK175) in a concentration-dependent manner (FIG. 14). At this time, a reduction in the body weight was not observed, which shows that the GPC1-ADC had no characteristic toxicity unlike the control ADC. Compared with the systemic administration of an anti-cancer agent, higher efficacy and lower toxicity are achieved by delivering an anti-cancer agent specifically to GPC1-positive cancer cells using the GPC1-ADC in vivo, which leads to development of an epoch-making therapeutic reagent for GPC1-positive cancer.

Example 11: In-Vivo Efficacy Test of GPC1-ADC Using Esophageal Cancer PDX (ESCC14)

Materials and Methods

The GPC1 expression in esophageal cancer PDX (ESCC14) was confirmed as follows.

Sections of a paraffin embedded tissue were subjected to deparaffinization, and was then dehydrated using alcohol. Immunohistochemical staining of GPC1 was performed using an anti-GPC-1 antibody (Genetex: GTX104557) and ChemMate Envision Kit HRP 500T (Dako: K5007). It was found that the ESCC14 was a homogeneous tumor in which GPC1 was highly expressed homogeneously in the esophageal cancer cells.

The esophageal cancer PDX was subcutaneously implanted into 6-week-old female NOG mice. When the size of the implanted tumor reached about 100 mm³, administration of PBS serving as a control and the humanized anti-GPC1-ADC (MMAE) produced in Example 4 (1 mg/kg, 3 mg/kg, 10 mg/kg) was started. The day on which the administration was started was taken as day 0, and intravenous administration was performed on day 0, day 7, day 14, and day 21. The tumor volume and the body weight were measured from day 0 to day 42 at a frequency of twice a week.

Results

Figure 15:
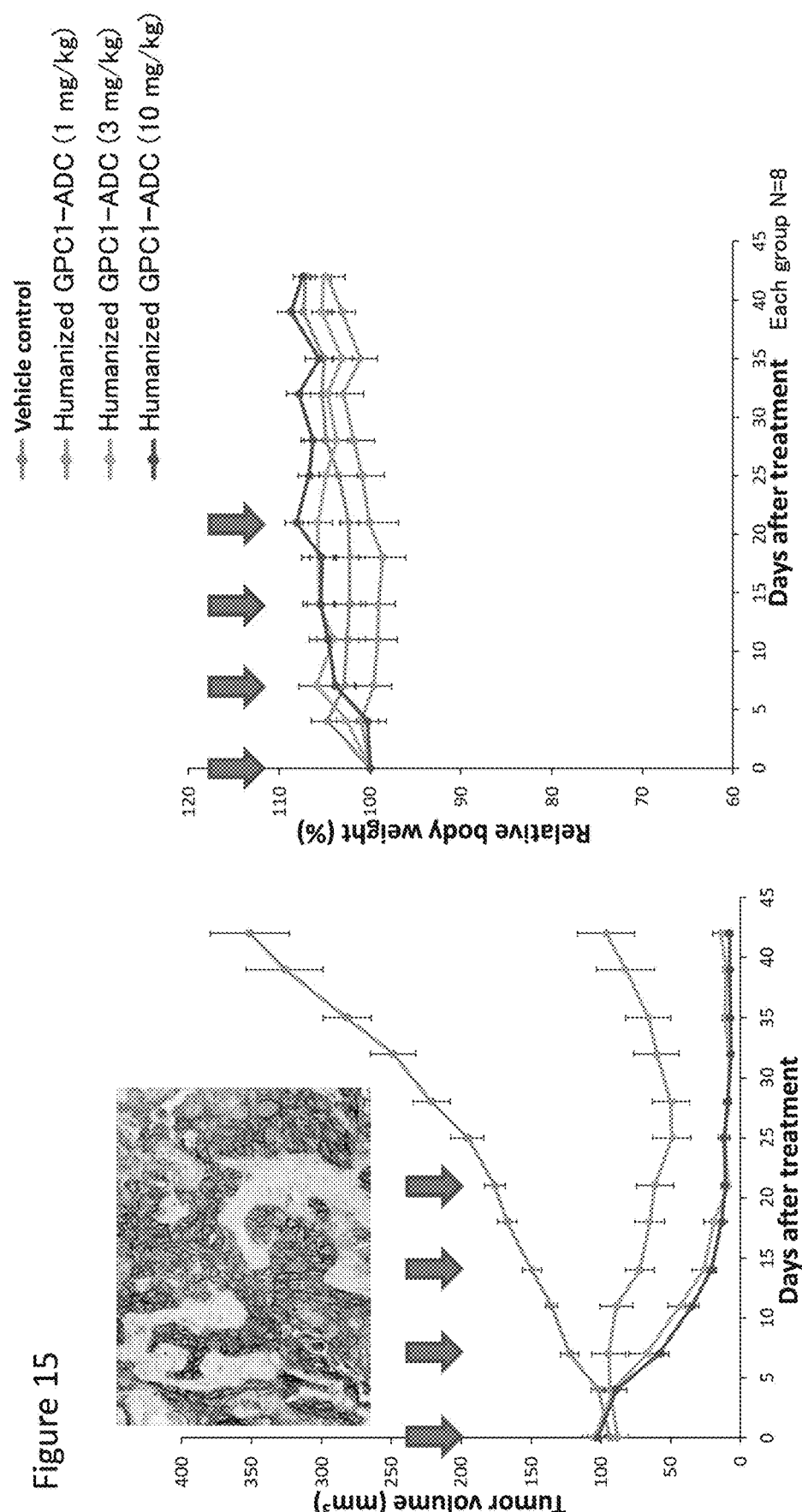
FIG. 15 shows the results of an in-vivo efficacy test of a humanized GPC1-ADC (MMAE) using an esophageal cancer PDX (ESCC14) in which GPC1 is highly expressed homogeneously. In all the groups, the body weights did not significantly change. The tumor volumes were equivalent to each other and the smallest in the cases of Humanized GPC1-ADC (10 mg/kg) and Humanized GPC1-ADC (3 mg/kg), the tumor volume was almost unchanged in the case of Humanized GPC-ADC (1 mg/kg), and the tumor volume gradually increased in the case of Vehicle control.

As a result of intravenously administering the medicine weekly, four times in total, in the in-vivo efficacy test, the humanized GPC1-ADC also had a high anti-tumor effect on the GPC1-positive esophageal cancer PDX mice (ESCC14) in a concentration-dependent manner (FIG. 15). At this time, a reduction in the body weight was not observed, which shows that the GPC1-ADC had no characteristic toxicity unlike the control ADC. Compared with the systemic administration of an anti-cancer agent, higher efficacy and lower toxicity are achieved by delivering an anti-cancer agent specifically to GPC1-positive cancer cells using the GPC1-ADC in vivo, which leads to development of an epoch-making therapeutic reagent for GPC1-positive cancer.

Example 12: GPC1 Expression Analysis Through FACS Analysis of Mouse Colorectal Cancer Cell Line Forced to Express mGPC1 (mGPC1-MC38)

Materials and Methods

The measurement of the mGPC1-MC38 cells was performed with FACS CantoII (BD) using the humanized anti-GPC1 antibody (clone T2) as a primary antibody and FITC labeled anti-human-IgG-FITC (Jackson Immuno Research, Catalog No. 109-095-098) as a secondary antibody, and the measurement data were analyzed using BD FACS Diva Software (BD).

Furthermore, the in-vitro ADC assay was performed on the mGPC1-MC38 cells in the same manner as in Example 8.

Results

It is known that some types of payloads such as MMAE used in an ADC induce cell death of cancer cells including immunogenic cell death (ICD). ICD-induced cancer cells release intranuclear proteins such as HMGB1 known as the damage-associated molecular patterns (DAMPs) to the outside, and thus maturation and activation of dendritic cells are promoted via TLR-4. Then, antigen-specific T cells invade a tumor and exhibits an anti-tumor effect. Accordingly, it is expected that using the humanized GPC1-ADC and an immune checkpoint inhibitor together provides a synergistic anti-tumor effect. Therefore, MC38-mGPC1, which is MC38 (mouse colorectal cancer cell line) that stably expresses mouse GPC1, was used to carry out an in-vitro experiment, and syngenic mice were used to carry out an in-vivo experiment. The humanized anti GPC1-ADC had a cell proliferation inhibiting activity against the MC38-mGPC1 in vitro (FIG. 16).

Example 13: Quantification of HMGB-1 in Culture Supernatant Using ELISA

Materials and Methods

A control-ADC, the humanized GPC1-ADC, and MMAE were added to the MC38-mGPC1 in vitro, and the culture supernatants were collected after 48 hours. The concentration of the HMGB-1 in the culture supernatant was measured using HMGB1 ELISA KIT II-HMGB1 Measurement Reagent (Shino-Test Corporation, Catalog No. SNO-326054329).

Results

Figure 17:
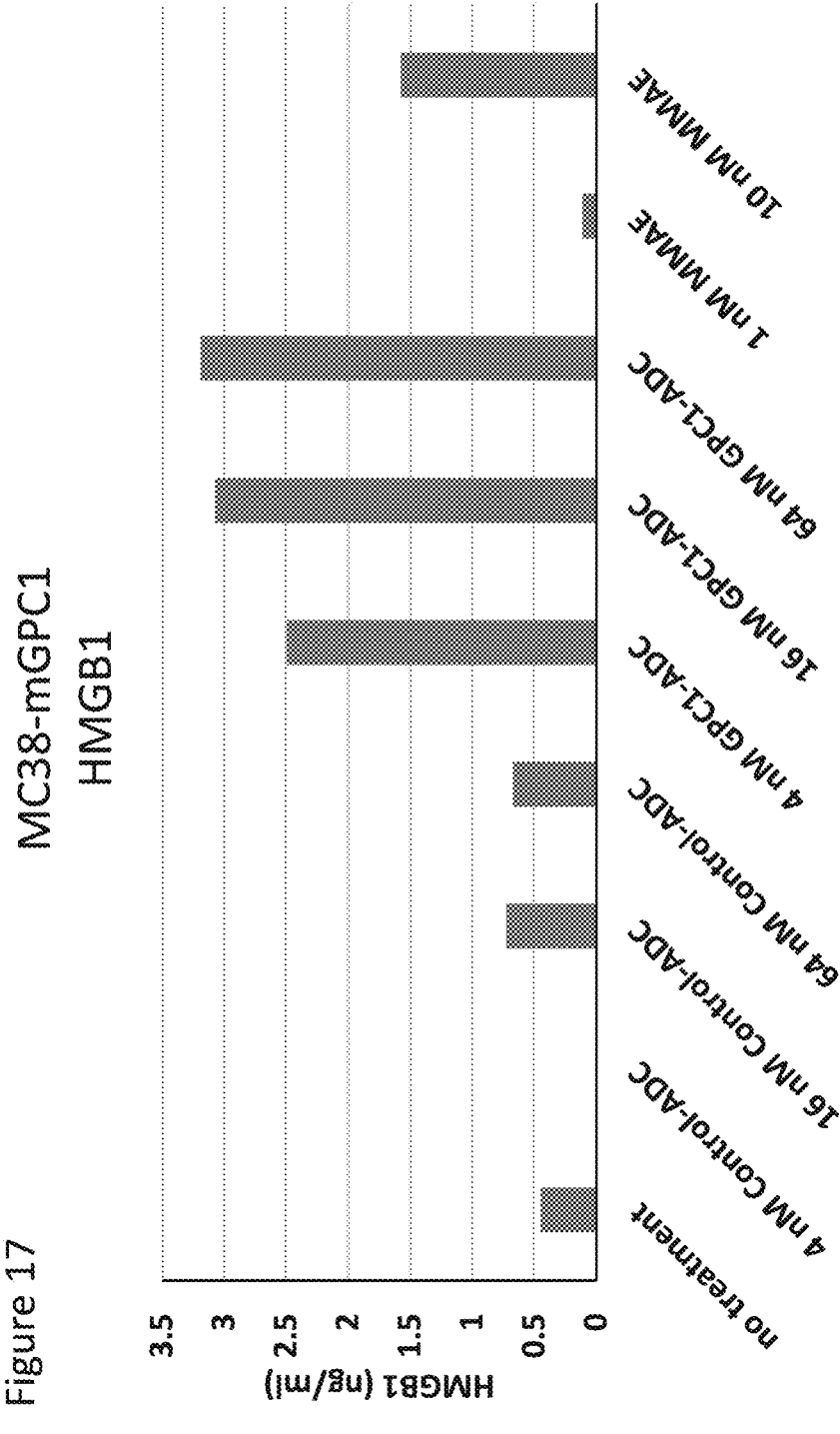
FIG. 17 shows the results of quantification of HMGB-1 in a culture supernatant, obtained through ELISA.

As a result of adding the humanized anti-GPC1-ADC produced in Example 4 to the MC38-mGPC1 and quantifying the HMGB1 in the culture supernatant through ELISA, it was found that extracellular release of the HMGB1 was induced (FIG. 17). The HMGB1 (high mobility group box-1) is an intranuclear protein known as one of the DAMPs (damage-associated molecular patterns). When some type of anti-cancer agent causes cell death of cancer cells, the HMGB1 is released to the outside of the cell and is thus known as an index of immunogenic cell death. The HMGB1 released to the outside of the cell binds to TLR4 on a dendritic cell to promote activation and maturation of the dendritic cell, and as a result, invasion of T cells into a tumor tissue and the like are promoted.

Example 14: Confirmation of Synergistic Effect Caused by Concurrent Use of Humanized GPC1-ADC (MMAE) and Anti-PD1 Antibody Using Colorectal Cancer Syngenic Model Mouse Materials and Methods The MC38-mGPC1 was subcutaneously implanted into 8-week-old female C57BL/6 mice. When the size of the implanted tumor reached about 75 mm$^3$, the mice were divided into four groups, and administration of PBS, the humanized anti-GPC1-ADC (MMAE) produced in Example 4 (10 mg/kg), the anti-mouse-PD1 antibody (clone RMP1-14) (3 mg/kg), and a combination of the humanized anti-GPC1-ADC (MMAE) (10 mg/kg) and the anti-mouse-PD1 antibody (clone RMP1-14) (3 mg/kg) was started. The day on which the administration was started was taken as day 0, and intravenous administration of the ADC and intraperitoneal administration of the anti-mouse-PD1 antibody were performed on day 0, day 3, day 7, and day 10. The tumor volume and the body weight were measured from day 0 to day 21 at a frequency of twice a week.

Results

Figure 18:
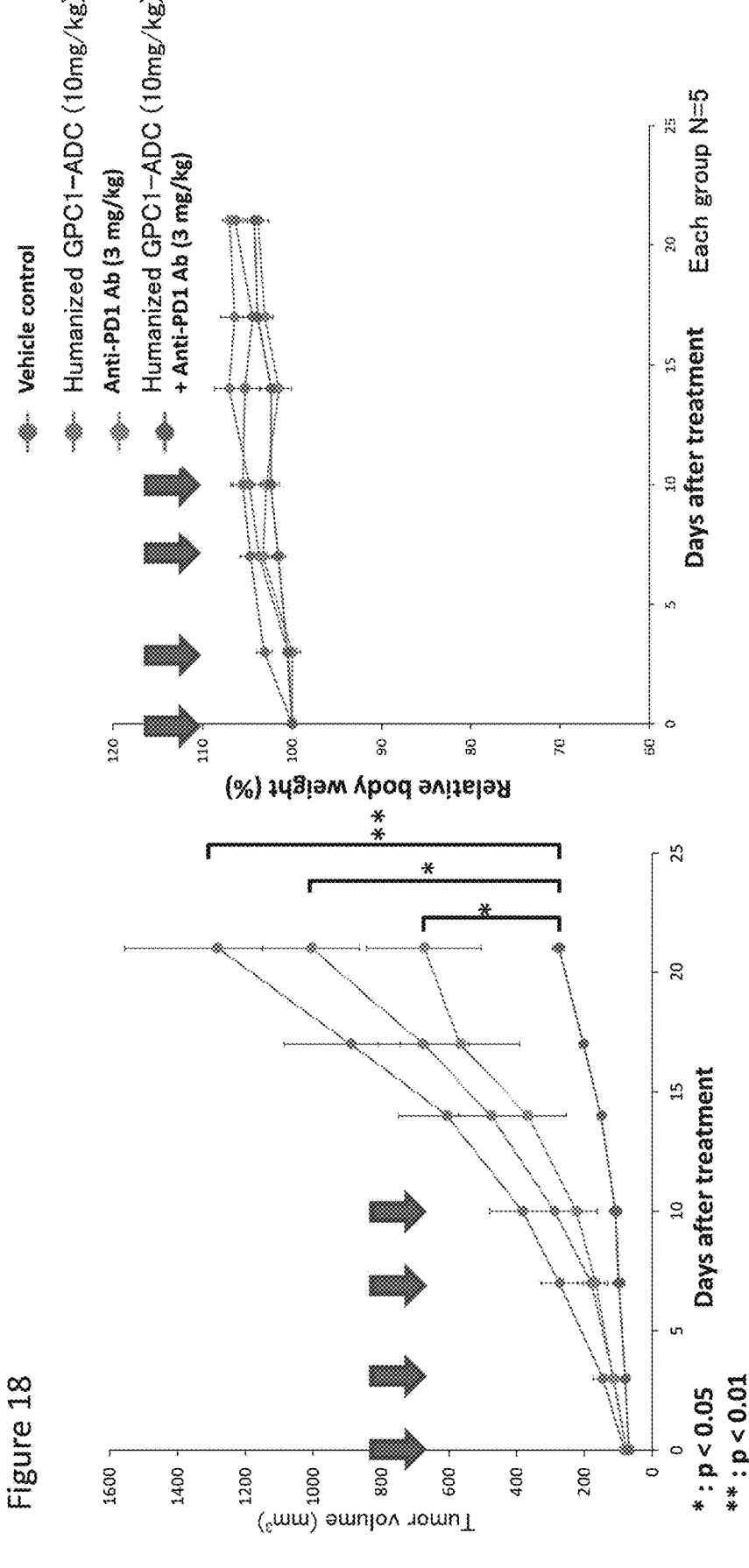
FIG. 18 shows the results of an anti-tumor effect analysis performed on syngenic colorectal cancer model mice using a humanized GPC1-ADC (MMAE) and an anti-PD1 antibody together. In all the groups, the body weights did not significantly change. The tumor volume was the smallest in the case of Humanized GPC1-ADC (10 mg/kg)+anti-PD1 Ab (3 mg/kg), and increased in the order of anti-PD1 Ab (3 mg/kg), Humanized GPC1-ADC (10 mg/kg), and Vehicle control.

C57BL/6 mice into which the MC38-mGPC1 was subcutaneously implanted were used as syngenic models and were divided into four groups, namely groups for the vehicle control, the humanized anti-GPC1-ADC, the anti-PD1 antibody, and the combination of the humanized anti-GPC1-ADC and the anti-PD1 antibody. The medicines were administered at a frequency of twice a week, four times in total, and the anti-tumor effect was evaluated. As a result, the humanized GPC1-ADC and the anti-PD1 antibody had a significant anti-tumor effect in the concurrent administration group, unlike the single administration groups. On the other hand, a reduction in body weight caused by the concurrent administration of the humanized GPC1-ADC and the anti-PD1 antibody was not observed (FIG. 18). It is expected from these results that using the humanized GPC1-ADC and a checkpoint inhibitor together provides a synergistic anti-tumor effect.

Example 15: In-Vivo Action Mechanism Analysis of Humanized GPC1-ADC (MMAE) Using Pancreatic Cancer PDX (PK565)

Materials and Methods

A pancreatic cancer PDX (PK565) was subcutaneously implanted into 6-week-old female NOG mice. When the size of the implanted tumor reached about 100 mm$^3$, administration of PBS, a control ADC (10 mg/kg), and the humanized anti-GPC1-ADC (MMAE) produced in Example 4 (1 mg/kg, 3 mg/kg, 10 mg/kg) was started. The tumor was removed 24 hours after the administration. After the removed tissue was fixed using 10% neutral hormalin buffer, a paraffin embedded tissue was produced, and sections were prepared. In order to evaluate cancer cells whose cell cycle stopped at the G2/M phase in each section, the expression of phospho-histone H3 (Ser10) was analyzed through immunohistochemical staining.

Results

Figure 19:
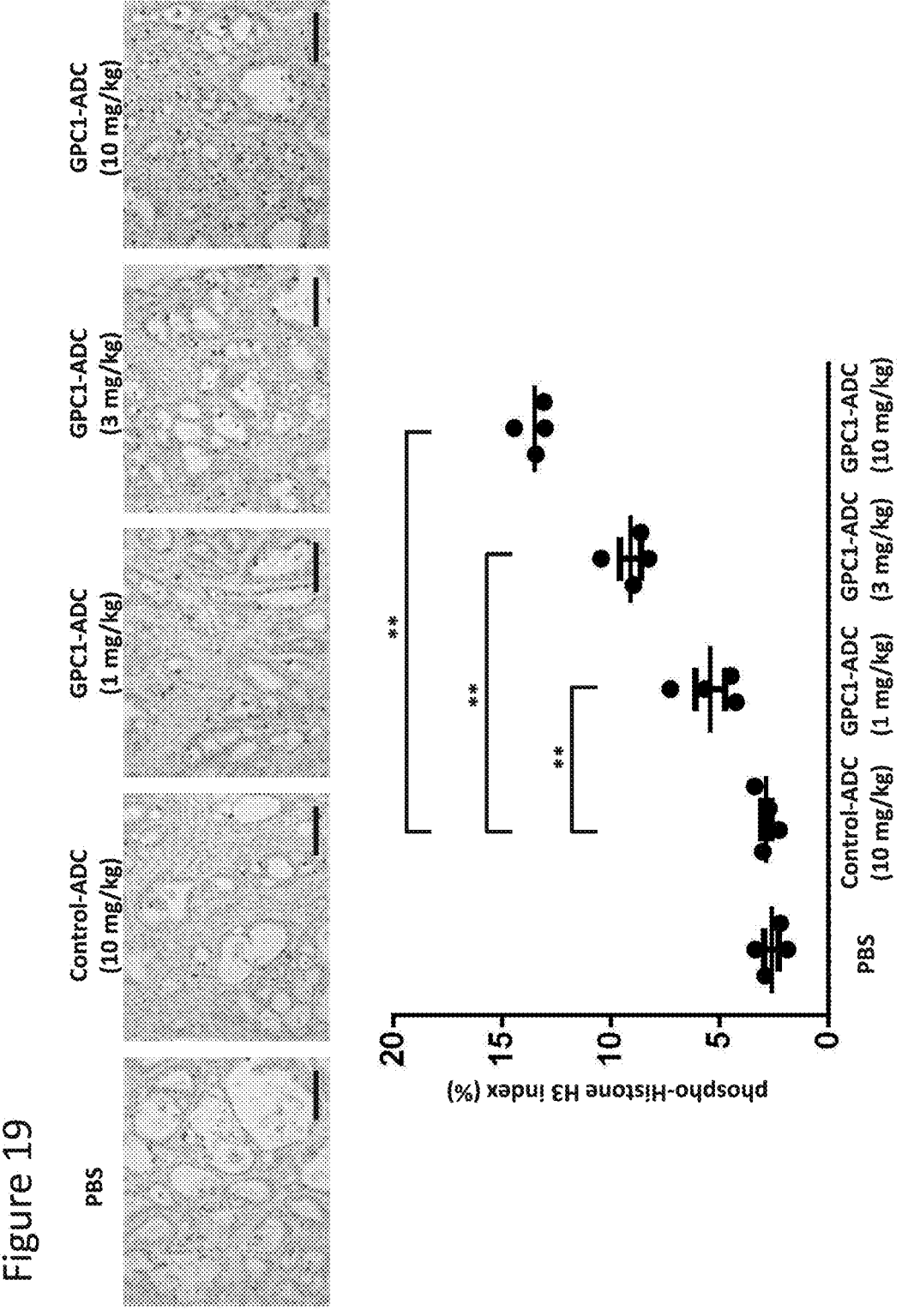
FIG. 19 shows the measurement results of a G2/M phase cell cycle marker (phospho-Histone H3 (Ser10)) in a pancreatic cancer PDX (PK565). The scale bar indicates 100 μm. "**" indicates P<0.01 in one-way ANOVA after the Dunnett's post hoc test.

It was found from the results that, compared with the PBS administration group and the control ADC (10 mg/kg) administration group, the ratio of cancer cells whose cell cycle stopped at the G2/M phase significantly increased in a concentration-dependent manner in the humanized anti-GPC1-ADC (MMAE) administration group (FIG. 19). When the payload of the ADC acts on cancer cells and stops the cell cycle at the G2/M phase, the proliferation of the cancer cells is stopped, thus contributing to the extension of the survival time of a cancer patient.

Figure 20:
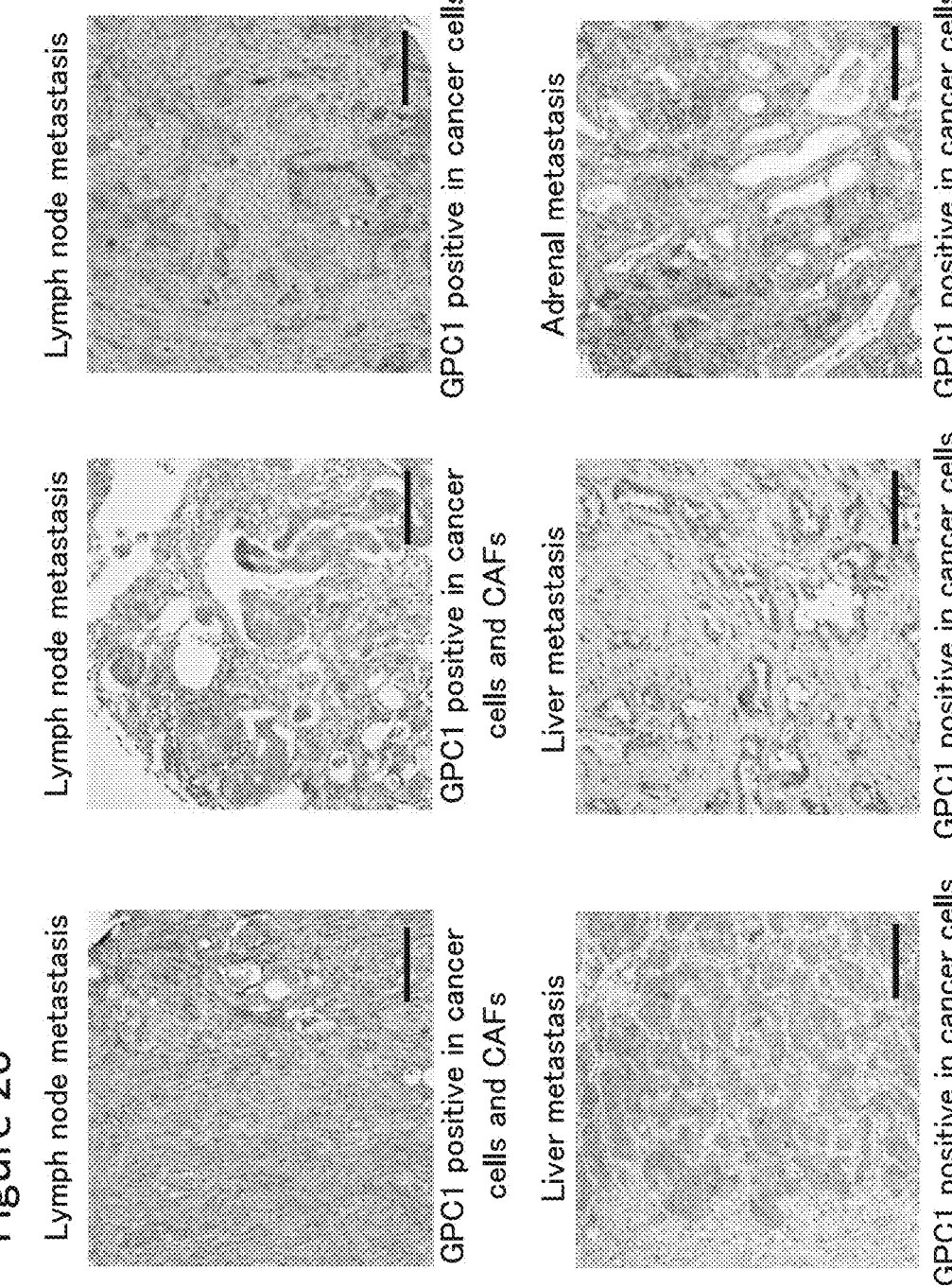
FIG. 20 shows the results of a GPC1-expression analysis of a distant pancreatic cancer metastatic tissue, obtained through immunohistochemical staining. The scale bar indicates 100 m.

Example 16: GPC1-Expression Analysis of Distant Pancreatic Cancer Metastatic Tissue Through Immunohistochemical Staining Distant metastases such as a lymph node metastasis and a liver metastasis are known as poor prognostic factors of pancreatic cancer. Therefore, if GPC1 is expressed in not only the primary lesion of pancreatic cancer but also distant metastatic lesions, it is conceivable that GPC1 is very useful as a treatment target. Accordingly, the GPC1 expression in pancreatic cancer metastatic tissues in the lymph node, the liver, and the adrenal was evaluated through immunohistochemical staining. As a result, it was found that the GPC1 expression was positive in all the pancreatic cancer metastatic tissues in the lymph node, the liver, and the adrenal (FIG. 20). Accordingly, this suggests that the humanized GPC1-ADC (MMAE) of the present invention is effective in treatment or prevention of metastatic cancer of GPC1-positive cancer.

Example 17: Production of Pancreatic Cancer Liver Metastasis Model and Efficacy Test of Humanized GPC1-ADC In order to confirm the metastatic cancer treatment effect or metastatic cancer prevention effect of the humanized GPC1-ADC (MMAE), which was suggested in Example 16, a pancreatic cancer liver metastasis model was produced.

Materials and Methods

BxPC3-Luc cells were administered to the spleen of an SCID mouse in accordance with the procedure shown in FIG. 21, and the spleen was removed 1 to 2 weeks after the administration. Thus, a pancreatic cancer liver metastasis model was produced. The proliferation of the BxPC3-Luc cells metastatic to the liver was monitored by measuring the luciferase activity using IVIS. The liver metastasis model mice were divided into two groups, namely a PBS administration group and a humanized anti-GPC1-ADC (MMAE) (produced in Example 4) (10 mg/kg) administration group, and the efficacy test was performed in the same procedure as in Example 16.

Results

Figure 22:
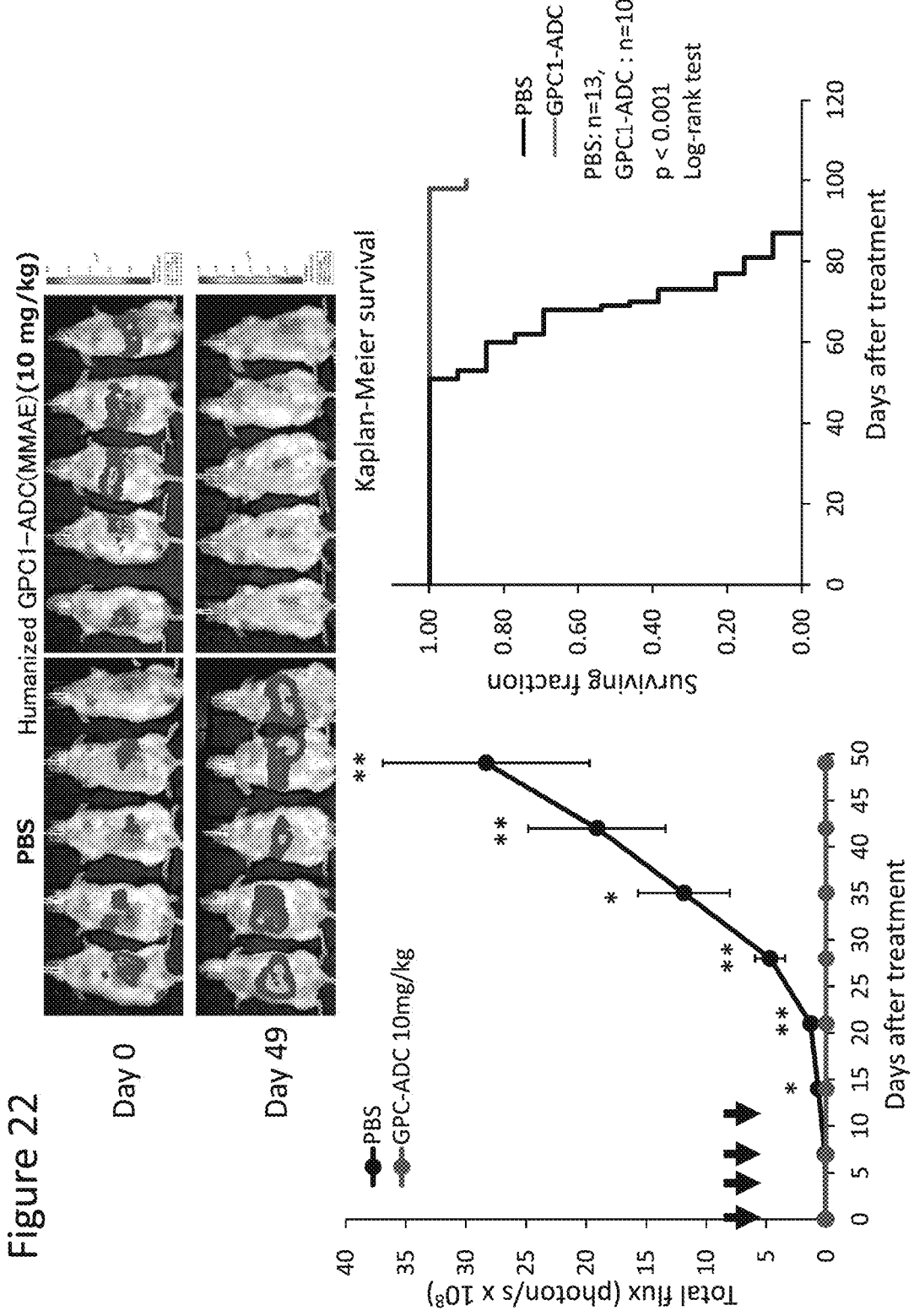
FIG. 22 shows the results of an efficacy test of a humanized GPC1-ADC using the pancreatic cancer liver metastasis model. PBS administration group: n=13, GPC1-ADC 10 mg/kg administration group: n=10, *: p<0.05, **: p<0.01.

As a result, as shown in the left diagram of FIG. 22, it was found from the values obtained through the measurements using IVIS that the emission of the humanized anti-GPC1-ADC (MMAE) (10 mg/kg) administration group was significantly inhibited compared with the PBS administration group. In addition, it was found from the results of a survival analysis that the humanized anti-GPC1-ADC (MMAE) (10 mg/kg) significantly extended the survival time of the pancreatic cancer liver metastasis model.

Example 18: Efficacy Test of Humanized GPC1-ADC Using Metastatic Cancer

Metastasis models of metastasis to the liver, the lung, the brain, the bone, the peritoneum, the adrenal, and the like are produced, and the efficacy of the humanized GPC1-ADC in the metastasis models is confirmed. It is expected that the humanized GPC1-ADC has efficacy in both the primary lesion and the metastatic lesions and exhibits an effect of extending the survival time.

Example 19: Formulation Example

The humanized anti-GPC1-ADC (MMAE) of the present invention may be provided as a formulation for intravenous injection having the following composition.

| | |
|---|---|
| Humanized anti-GPC1-ADC | 100 mg |
| Polysorbate 80 | 5 mg |
| Sodium chloride | 100 mg |
| Sodium citrate hydrate | 80 mg |
| pH adjuster | appropriate amount |
| Total amount | 10 mL |

As described above, the preferred embodiments of the present disclosure have been used as examples of the present disclosure, but it is understood that the scope of the present disclosure should be construed by only the claims. It is understood that the contents of the patents, patent applications, and literature cited herein should be incorporated herein by reference in their entireties as if specifically set forth herein. The present application claims the benefit of priority from Japanese Patent Application No. 2020-101856 filed on Jun. 11, 2020, the contents of which are incorporated herein by reference.

INDUSTRIAL APPLICABILITY

A pharmaceutical drug for treatment or prevention of cancer was provided. A technology capable of being used in the industries (e.g., pharmaceutical industry) based on such a technology is provided.

Free Text of Sequence Listing

SEQ ID NO: 1: Nucleic acid sequence of human Glypican-1

SEQ ID NO: 2: Amino acid sequence of human Glypican-1

SEQ ID NO: 3: Nucleic acid sequence of mouse Glypican-1

SEQ ID NO: 4: Amino acid sequence of Mouse Glypican-1

SEQ ID NO: 5: Amino acid sequence of heavy-chain variable region of 01a033

SEQ ID NO: 6: Amino acid sequence of light-chain variable region of 01a033

SEQ ID NO: 7: Amino acid sequence of humanized heavy-chain variable region

SEQ ID NO: 8: Amino acid sequence of humanized light-chain variable region of clone T2

SEQ ID NO: 9: Amino acid sequence of humanized light-chain variable region of clone T7

SEQ ID NO: 10: Amino acid sequence of humanized light-chain variable region of clone T8

SEQ ID NO: 11: Amino acid sequence of humanized light-chain variable region of clone T1

SEQ ID NO: 12: Amino acid sequence of humanized light-chain variable region of clone T36

SEQ ID NO: 13: Amino acid sequence of humanized light-chain variable region of clone T57

SEQ ID NO: 14: Amino acid sequence of humanized light-chain variable region of clone T10

SEQ ID NO: 15: Amino acid sequence of humanized light-chain variable region of clone T34

SEQ ID NO: 16: Amino acid sequence of humanized light-chain variable region of clone T56

SEQ ID NO: 17: Amino acid sequence of humanized light-chain variable region of clone T3

SEQ ID NO: 18: Amino acid sequence of humanized light-chain variable region of clone T11

SEQ ID NO: 19: Amino acid sequence of humanized light-chain variable region of clone T28

SEQ ID NO: 20: Amino acid sequence of humanized light-chain variable region of clone T43

SEQ ID NO: 21: Amino acid sequence of humanized light-chain variable region of clone T59

SEQ ID NO: 22: Amino acid sequence of humanized light-chain variable region of clone T31

SEQ ID NO: 23: Amino acid sequence of humanized light-chain variable region of clone T22

SEQ ID NO: 24: Amino acid sequence of humanized light-chain variable region of clone T26

SEQ ID NO: 25: Amino acid sequence of humanized light-chain variable region of clone T32

SEQ ID NO: 26: Amino acid sequence of humanized light-chain variable region of clone T33

SEQ ID NO: 27: Amino acid sequence of humanized light-chain variable region of clone T29

SEQ ID NO: 28: Amino acids of heavy-chain CDR1 of humanized heavy chain

SEQ ID NO: 29: Amino acids of heavy-chain CDR2 of humanized heavy chain

SEQ ID NO: 30: Amino acids of heavy-chain CDR3 of humanized heavy chain

SEQ ID NO: 31: Amino acid sequence of light-chain CDR1 of clone T2

SEQ ID NO: 32: Amino acid sequence of light-chain CDR2 of clone T2

SEQ ID NO: 33: Amino acid sequence of light-chain CDR3 of clone T2

SEQ ID NO: 34: Amino acid sequence of light-chain CDR1 of clone T7

SEQ ID NO: 35: Amino acid sequence of light-chain CDR2 of clone T7

SEQ ID NO: 36: Amino acid sequence of light-chain CDR3 of clone T7

SEQ ID NO: 37: Amino acid sequence of light-chain CDR1 of clone T8

SEQ ID NO: 38: Amino acid sequence of light-chain CDR2 of clone T8

SEQ ID NO: 39: Amino acid sequence of light-chain CDR3 of clone T8

SEQ ID NO: 40: Amino acid sequence of light-chain CDR1 of clone T1

SEQ ID NO: 41: Amino acid sequence of light-chain CDR2 of clone T1

SEQ ID NO: 42: Amino acid sequence of light-chain CDR3 of clone T1

SEQ ID NO: 43: Amino acid sequence of light-chain CDR1 of clone T36

SEQ ID NO: 44: Amino acid sequence of light-chain CDR2 of clone T36

SEQ ID NO: 45: Amino acid sequence of light-chain CDR3 of clone T36

SEQ ID NO: 46: Amino acid sequence of light-chain CDR1 of clone T57

SEQ ID NO: 47: Amino acid sequence of light-chain CDR2 of clone T57

SEQ ID NO: 48: Amino acid sequence of light-chain CDR3 of clone T57

SEQ ID NO: 49: Amino acid sequence of light-chain CDR1 of clone T10

SEQ ID NO: 50: Amino acid sequence of light-chain CDR2 of clone T10

SEQ ID NO: 51: Amino acid sequence of light-chain CDR3 of clone T10

SEQ ID NO: 52: Amino acid sequence of light-chain CDR1 of clone T34

SEQ ID NO: 53: Amino acid sequence of light-chain CDR2 of clone T34

SEQ ID NO: 54: Amino acid sequence of light-chain CDR3 of clone T34

SEQ ID NO: 55: Amino acid sequence of light-chain CDR1 of clone T56

SEQ ID NO: 56: Amino acid sequence of light-chain CDR2 of clone T56

SEQ ID NO: 57: Amino acid sequence of light-chain CDR3 of clone T56

SEQ ID NO: 58: Amino acid sequence of light-chain CDR1 of clone T3

SEQ ID NO: 59: Amino acid sequence of light-chain CDR2 of clone T3

SEQ ID NO: 60: Amino acid sequence of light-chain CDR3 of clone T3

SEQ ID NO: 61: Amino acid sequence of light-chain CDR1 of clone T11

SEQ ID NO: 62: Amino acid sequence of light-chain CDR2 of clone T11

SEQ ID NO: 63: Amino acid sequence of light-chain CDR3 of clone T11

SEQ ID NO: 64: Amino acid sequence of light-chain CDR1 of clone T28

SEQ ID NO: 65: Amino acid sequence of light-chain CDR2 of clone T28

SEQ ID NO: 66: Amino acid sequence of light-chain CDR3 of clone T28

SEQ ID NO: 67: Amino acid sequence of light-chain CDR1 of clone T43

SEQ ID NO: 68: Amino acid sequence of light-chain CDR2 of clone T43

SEQ ID NO: 69: Amino acid sequence of light-chain CDR3 of clone T43

SEQ ID NO: 70: Amino acid sequence of light-chain CDR1 of clone T59

SEQ ID NO: 71: Amino acid sequence of light-chain CDR2 of clone T59

SEQ ID NO: 72: Amino acid sequence of light-chain CDR3 of clone T59

SEQ ID NO: 73: Amino acid sequence of light-chain CDR1 of clone T31

SEQ ID NO: 74: Amino acid sequence of light-chain CDR2 of clone T31

SEQ ID NO: 75: Amino acid sequence of light-chain CDR3 of clone T31

SEQ ID NO: 76: Amino acid sequence of light-chain CDR1 of clone T22

SEQ ID NO: 77: Amino acid sequence of light-chain CDR2 of clone T22

SEQ ID NO: 78: Amino acid sequence of light-chain CDR3 of clone T22

SEQ ID NO: 79: Amino acid sequence of light-chain CDR1 of clone T26

SEQ ID NO: 80: Amino acid sequence of light-chain CDR2 of clone T26

SEQ ID NO: 81: Amino acid sequence of light-chain CDR3 of clone T26

SEQ ID NO: 82: Amino acid sequence of light-chain CDR1 of clone T32

SEQ ID NO: 83: Amino acid sequence of light-chain CDR2 of clone T32

SEQ ID NO: 84: Amino acid sequence of light-chain CDR3 of clone T32

SEQ ID NO: 85: Amino acid sequence of light-chain CDR1 of clone T33

SEQ ID NO: 86: Amino acid sequence of light-chain CDR2 of clone T33

SEQ ID NO: 87: Amino acid sequence of light-chain CDR3 of clone T33

SEQ ID NO: 88: Amino acid sequence of light-chain CDR1 of clone T29

SEQ ID NO: 89: Amino acid sequence of light-chain CDR2 of clone T29

SEQ ID NO: 90: Amino acid sequence of light-chain CDR3 of clone T29

SEQ ID NO: 91: Amino acid sequence of heavy-chain constant region of chimeric antibody and humanized antibody SEQ ID NO: 92: Amino acid sequence of light-chain constant region of chimeric antibody and humanized antibody

The invention claimed is:

1. A humanized anti-GPC-1 antibody or an antigen-binding fragment thereof, comprising:
   heavy-chain CDRs 1 to 3 having amino acid sequences set forth in SEQ ID NOs: 28 to 30, respectively, and
   (a) light-chain CDRs 1 to 3 having amino acid sequences set forth in SEQ ID NOs: 31 to 33, respectively, or
   (b) light-chain CDRs 1 to 3 having amino acid sequences set forth in SEQ ID NOs: 37 to 39, respectively, or
   (c) light-chain CDRs 1 to 3 having amino acid sequences set forth in SEQ ID NOs: 40 to 42, respectively, or
   (d) light-chain CDRs 1 to 3 having amino acid sequences set forth in SEQ ID NOs: 43 to 45, respectively, or
   (e) light-chain CDRs 1 to 3 having amino acid sequences set forth in SEQ ID NOs: 49 to 51, respectively, or
   (f) light-chain CDRs 1 to 3 having amino acid sequences set forth in SEQ ID NOs: 55 to 57, respectively, or
   (g) light-chain CDRs 1 to 3 having amino acid sequences set forth in SEQ ID NOs: 58 to 60, respectively.

2. The humanized antibody or the antigen-binding fragment thereof according to claim 1, comprising:
   a heavy-chain variable region having an amino acid sequence with at least 90% identity to an amino acid sequence set forth in SEQ ID NO: 7; and/or
   a light-chain variable region having an amino acid sequence with at least 90% identity to an amino acid sequence selected from the group consisting of amino acid sequences set forth in SEQ ID NOs: 8, 10, 11, 12, 14, 16 and 17; or
   a light-chain variable region having an amino acid sequence selected from the group consisting of amino acid sequences set forth in SEQ ID NOs: 8, 10, 11, 12, 14, 16 and 17.

3. The humanized antibody or the antigen-binding fragment thereof according to claim 1, wherein an epitope of the antibody includes positions 339 to 358 and/or 388 to 421 of SEQ ID NO: 2.

4. The humanized antibody or the antigen-binding fragment thereof according to claim 1, wherein
   the antibody binds to GPC-1 with a $K_D$ of $1.02E^{-8}$ or less, the $K_D$ being based on analysis using a surface plasmon resonance technique.

5. A complex of the humanized antibody or the antigen-binding fragment thereof according to claim 1, and a medicine having cytotoxic activity.

6. The complex according to claim 5, wherein
   the humanized antibody or the antigen-binding fragment thereof is operably linked to the medicine having cytotoxic activity via a linker.

7. The complex according to claim 5, wherein
the medicine having cytotoxic activity is selected from the
group consisting of monomethyl auristatin E (MMAE),
monomethyl auristatin F (MMAF), DM1, DM4, cali-
cheamicin, duocarmycin, pyrrolobenzodiazepine
(PBD), and topoisomerase inhibitors.

8. The complex according to claim 6,
wherein the medicine having cytotoxic activity has cell
membrane permeability.

9. The complex according to claim 6, wherein
the medicine having cytotoxic activity is selected from
MMAE, PBD, Eribulin, SN-38, Dxd, and DM4.

10. The complex according to claim 6, wherein
the linker is selected from the group consisting of an
enzyme cleavable linker, an acid labile linker, and a
disulfide linker.

11. The complex according to claim 6, wherein
the linker is a cleavable linker capable of being cleaved by
cathepsin B.

12. The complex according to claim 5, wherein
the complex has an $IC_{50}$ of about 0.1 nM or less in a
GPC-1-positive cell.

13. A method for preventing or treating GPC-1-positive
cancer in a subject, the method comprising:
administering the complex according to claim 12 to the
subject.

14. The method according to claim 13, wherein
the GPC-1-positive cancer is selected from esophageal
cancer, pancreatic cancer, bile duct cancer, cervical
cancer, lung cancer, head and neck cancer, breast
cancer, uterine leiomyosarcoma, prostate cancer, oral
squamous cell cancer, and any combinations thereof.

15. The method according to claim 13, wherein
wherein the GPC-1-positive cancer is esophageal cancer
or pancreatic cancer.

16. The method according to claim 13, wherein
the GPC-1-positive cancer has cancer-associated fibro-
blasts (CAFs).

17. The method according to claim 13, the method, further
comprising:
administering an immune checkpoint inhibitor.

18. The method according to claim 17, wherein
the immune checkpoint inhibitor is an anti-PD-1 antibody.

* * * * *